United States Patent
Tamarkin et al.

(10) Patent No.: US 10,588,858 B2
(45) Date of Patent: *Mar. 17, 2020

(54) FOAMABLE VEHICLES AND PHARMACEUTICAL COMPOSITIONS COMPRISING APROTIC POLAR SOLVENTS AND USES THEREOF

(71) Applicant: Foamix Pharmaceuticals Ltd., Rehovot (IL)

(72) Inventors: Dov Tamarkin, Ness Ziona (IL); David Schuz, Gimzu (IL); Tal Berman, Rishon le Ziyyon (IL); Yohan Hazot, Rehovot (IL)

(73) Assignee: FOAMIX PHARMACEUTICALS LTD., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/443,649

(22) Filed: Jun. 17, 2019

(65) Prior Publication Data

US 2020/0016077 A1   Jan. 16, 2020

Related U.S. Application Data

(60) Continuation of application No. 16/236,704, filed on Dec. 31, 2018, now Pat. No. 10,363,216, which is a
(Continued)

(51) Int. Cl.
*A61K 9/12* (2006.01)
*A61K 8/46* (2006.01)
(Continued)

(52) U.S. Cl.
CPC .............. *A61K 9/122* (2013.01); *A61K 8/046* (2013.01); *A61K 8/46* (2013.01); *A61K 9/0014* (2013.01);
(Continued)

(58) Field of Classification Search
CPC .......... A61K 9/122; A61K 8/46; A61K 47/38; A61K 47/20; A61K 47/14; A61K 47/26;
(Continued)

(56) References Cited

U.S. PATENT DOCUMENTS

| | | |
|---|---|---|
| 1,159,250 A | 11/1915 | Moulton |
| 1,666,684 A | 4/1928 | Carstens |

(Continued)

FOREIGN PATENT DOCUMENTS

| | | |
|---|---|---|
| AU | 198780257 A | 9/1986 |
| AU | 782515 B2 | 12/2005 |

(Continued)

OTHER PUBLICATIONS

"Everything but the Olive." The Olive Oil Source 1998-2016 [online]. Retrieved from the Internet: http://www.oliveoilsource.com/pageA chemical-characteristics.
(Continued)

*Primary Examiner* — Trevor Love
(74) *Attorney, Agent, or Firm* — Finnegan, Henderson, Farabow, Garrett & Dunner, LLP

(57) ABSTRACT

The present invention teaches a foamable pharmaceutical and cosmetic compositions comprising an aprotic polar solvent; foam compositions and uses thereof.

9 Claims, 5 Drawing Sheets

| | Control | Classic Emollient | D52 (containing petrolatum) | D50 (containing urea) | D51 (containing water) |
|---|---|---|---|---|---|
| Increase in skin hydration 4 hours after application | 19.5 | 30.2 | 42.0 | 42.8 | 41.1 |

Related U.S. Application Data continuation of application No. 15/883,134, filed on Jan. 30, 2018, now Pat. No. 10,213,384, which is a continuation of application No. 15/639,114, filed on Jun. 30, 2017, now Pat. No. 9,884,017, which is a division of application No. 13/263,201, filed as application No. PCT/IB2010/001126 on Apr. 28, 2010, now abandoned.

(60) Provisional application No. 61/173,378, filed on Apr. 28, 2009.

(51) Int. Cl.
　　*A61K 47/38*　　(2006.01)
　　*A61K 47/20*　　(2006.01)
　　*A61Q 19/00*　　(2006.01)
　　*A61K 47/14*　　(2017.01)
　　*A61K 47/26*　　(2006.01)
　　*A61K 9/00*　　(2006.01)
　　*A61K 8/04*　　(2006.01)

(52) U.S. Cl.
　　CPC .............. *A61K 47/14* (2013.01); *A61K 47/20* (2013.01); *A61K 47/26* (2013.01); *A61K 47/38* (2013.01); *A61Q 19/00* (2013.01); *A61K 2800/31* (2013.01)

(58) Field of Classification Search
　　CPC .. A61K 9/0014; A61K 8/046; A61K 2800/31; A61Q 19/00
　　See application file for complete search history.

(56) References Cited

U.S. PATENT DOCUMENTS

| | | |
|---|---|---|
| 1,924,972 A | 8/1933 | Beckert |
| 2,085,733 A | 7/1937 | Bird |
| 2,390,921 A | 12/1945 | Clark |
| 2,524,590 A | 10/1950 | Boe |
| 2,586,287 A | 2/1952 | Apperson |
| 2,617,754 A | 11/1952 | Neely |
| 2,767,712 A | 10/1956 | Waterman |
| 2,968,628 A | 1/1961 | Reed |
| 3,004,894 A | 10/1961 | Johnson et al. |
| 3,062,715 A | 11/1962 | Reese et al. |
| 3,067,784 A | 12/1962 | Gorman |
| 3,092,255 A | 6/1963 | Hohman |
| 3,092,555 A | 6/1963 | Horn |
| 3,141,821 A | 7/1964 | Compeau |
| 3,142,420 A | 7/1964 | Gawthrop |
| 3,144,386 A | 8/1964 | Brightenback |
| 3,149,543 A | 9/1964 | Naab |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienkiewicz |
| 3,263,867 A | 8/1966 | Lehmann |
| 3,263,869 A | 8/1966 | Corsette |
| 3,298,919 A | 1/1967 | Bishop et al. |
| 3,301,444 A | 1/1967 | Wittke |
| 3,303,970 A | 2/1967 | Breslau et al. |
| 3,330,730 A | 7/1967 | Hernandez |
| 3,333,333 A | 8/1967 | Noack |
| 3,334,147 A | 8/1967 | Brunelle et al. |
| 3,342,845 A | 9/1967 | Sayigh et al. |
| 3,346,451 A | 10/1967 | Collins et al. |
| 3,366,494 A | 1/1968 | Bower et al. |
| 3,369,034 A | 2/1968 | Chalmers |
| 3,377,004 A | 4/1968 | Wittke |
| 3,383,280 A | 5/1968 | Kuehns |
| 3,384,541 A | 5/1968 | Clark et al. |
| 3,395,214 A | 7/1968 | Mummert |
| 3,395,215 A | 7/1968 | Schubert |
| 3,401,849 A | 9/1968 | Weber, III |
| 3,419,658 A | 12/1968 | Sanders |
| 3,456,052 A | 7/1969 | Gordon |
| 3,527,559 A | 9/1970 | Sliwinski |
| 3,540,448 A | 11/1970 | Sunnen |
| 3,559,890 A | 2/1971 | Brooks et al. |
| 3,561,262 A | 2/1971 | Borucki |
| 3,563,098 A | 2/1971 | Weber, III |
| 3,574,821 A | 4/1971 | Pfirrmann |
| 3,577,518 A | 5/1971 | Shepherd |
| 3,667,461 A | 6/1972 | Zamarra |
| 3,751,562 A | 8/1973 | Nichols |
| 3,770,648 A | 11/1973 | Mackles |
| 3,787,566 A | 1/1974 | Gauvreau |
| 3,819,524 A | 6/1974 | Schubert et al. |
| 3,824,303 A | 7/1974 | Lanzet et al. |
| 3,841,525 A | 10/1974 | Siegel |
| 3,849,569 A | 11/1974 | Mead |
| 3,849,580 A | 11/1974 | Weinstein et al. |
| 3,865,275 A | 2/1975 | De Nunzio |
| 3,866,800 A | 2/1975 | Schmitt |
| 3,878,118 A | 4/1975 | Watson |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,912,667 A | 10/1975 | Spitzer et al. |
| 3,923,970 A | 12/1975 | Breuer |
| 3,929,985 A | 12/1975 | Webb, Jr. |
| 3,952,916 A | 4/1976 | Phillips |
| 3,953,591 A | 4/1976 | Snyder |
| 3,959,160 A | 5/1976 | Horsler et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom |
| 4,001,391 A | 1/1977 | Feinstone et al. |
| 4,001,442 A | 1/1977 | Stahlberger et al. |
| 4,018,396 A | 4/1977 | Showmaker et al. |
| 4,019,657 A | 4/1977 | Spitzer et al. |
| 4,052,513 A | 10/1977 | Kaplan |
| 4,083,974 A | 4/1978 | Turi |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,178,373 A | 12/1979 | Klein et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,278,206 A | 7/1981 | Prussin |
| 4,292,250 A | 9/1981 | DeLuca et al. |
| 4,292,326 A | 9/1981 | Nazzaro-Porro et al. |
| 4,299,826 A | 11/1981 | Luedders |
| 4,305,936 A | 12/1981 | Klein |
| 4,309,995 A | 1/1982 | Sacco |
| 4,310,510 A | 1/1982 | Sherman et al. |
| 4,323,582 A | 4/1982 | Siegel et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,338,211 A | 7/1982 | Stiros |
| 4,352,808 A | 10/1982 | Rane et al. |

(56) References Cited

U.S. PATENT DOCUMENTS

| | | |
|---|---|---|
| 4,363,806 A | 12/1982 | Bergström et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,427,670 A | 1/1984 | Ofuchi et al. |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,595,526 A | 6/1986 | Lai |
| 4,603,812 A | 8/1986 | Stoesser et al. |
| 4,607,101 A | 8/1986 | Bernstein |
| 4,612,193 A | 9/1986 | Gordon et al. |
| 4,627,973 A | 12/1986 | Moran et al. |
| 4,628,063 A | 12/1986 | Haines et al. |
| 4,661,340 A | 4/1987 | Nagy née Kricsfalussy et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,772,427 A | 9/1988 | Dawson |
| 4,780,309 A | 10/1988 | Geria et al. |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,849,211 A | 7/1989 | Schrauzer |
| 4,851,154 A | 7/1989 | Grollier et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,876,083 A | 10/1989 | Grollier et al. |
| 4,877,805 A | 10/1989 | Kligman |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,933,330 A | 6/1990 | Jorgensen et al. |
| 4,950,420 A | 8/1990 | Svarz |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,965,063 A | 10/1990 | Casey et al. |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A | 1/1991 | Thau |
| 4,981,679 A | 1/1991 | Briggs et al. |
| 4,981,845 A | 1/1991 | Pereira et al. |
| 4,985,459 A | 1/1991 | Sunshine et al. |
| 4,992,478 A | 2/1991 | Geria |
| 4,993,496 A | 2/1991 | Riedle et al. |
| 4,996,193 A | 2/1991 | Hewitt et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,160,665 A | 11/1992 | Owada et al. |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,090 A | 4/1993 | Han |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,530 A | 6/1993 | Janchitraponvej et al. |
| 5,221,534 A | 6/1993 | DesLauriers et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,266,592 A | 11/1993 | Grub et al. |
| 5,279,819 A | 1/1994 | Hayes |
| 5,286,475 A | 2/1994 | Louvet et al. |
| 5,294,365 A | 3/1994 | Welch et al. |
| 5,300,286 A | 4/1994 | Gee |
| 5,301,841 A | 4/1994 | Fuchs |
| 5,308,643 A | 5/1994 | Osipow et al. |
| 5,314,904 A | 5/1994 | Egidio et al. |
| 5,318,774 A | 6/1994 | Alban et al. |
| 5,322,683 A | 6/1994 | Mackles et al. |
| 5,326,557 A | 7/1994 | Glover et al. |
| 5,344,051 A | 9/1994 | Brown |
| 5,346,135 A | 9/1994 | Vincent |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo Anna Z. et al. |
| 5,384,308 A | 1/1995 | Henkin |
| 5,385,943 A | 1/1995 | Nazzaro-Porro |
| 5,389,305 A | 2/1995 | Repinec et al. |

(56) References Cited

U.S. PATENT DOCUMENTS

| | | |
|---|---|---|
| 5,389,676 A | 2/1995 | Michaels |
| 5,397,312 A | 3/1995 | Rademaker et al. |
| 5,398,846 A | 3/1995 | Corba et al. |
| 5,399,205 A | 3/1995 | Shinohara et al. |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,439,670 A | 8/1995 | Purewal et al. |
| 5,439,682 A | 8/1995 | Wivell et al. |
| 5,447,725 A | 9/1995 | Damani et al. |
| 5,449,520 A | 9/1995 | Frigerio et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A | 4/1996 | Briand et al. |
| 5,512,555 A | 4/1996 | Waldstreicher |
| 5,514,367 A | 5/1996 | Lentini et al. |
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |
| 5,547,989 A | 8/1996 | Chamness |
| 5,558,872 A | 9/1996 | Jones et al. |
| 5,560,859 A | 10/1996 | Hartmann et al. |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |
| 5,589,157 A | 12/1996 | Hatfield |
| 5,589,515 A | 12/1996 | Suzuki et al. |
| 5,597,560 A | 1/1997 | Bergamini et al. |
| 5,603,940 A | 2/1997 | Candau et al. |
| 5,605,679 A | 2/1997 | Hansenne et al. |
| 5,608,119 A | 3/1997 | Amano et al. |
| 5,611,463 A | 3/1997 | Favre |
| 5,612,056 A | 3/1997 | Jenner et al. |
| 5,613,583 A | 3/1997 | Kono et al. |
| 5,613,623 A | 3/1997 | Hildebrandt |
| 5,614,171 A | 3/1997 | Clavenna et al. |
| 5,614,178 A | 3/1997 | Bloom et al. |
| 5,618,516 A | 4/1997 | Clavenna et al. |
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,648,380 A | 7/1997 | Martin |
| 5,650,554 A | 7/1997 | Moloney |
| 5,658,575 A | 8/1997 | Ribier et al. |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,686,088 A | 11/1997 | Mitra et al. |
| 5,693,258 A | 12/1997 | Tonomura et al. |
| 5,695,551 A | 12/1997 | Buckingham et al. |
| 5,695,747 A | 12/1997 | Forestier et al. |
| 5,700,396 A | 12/1997 | Suzuki et al. |
| 5,705,472 A | 1/1998 | Hayes et al. |
| 5,716,611 A | 2/1998 | Oshlack et al. |
| 5,716,621 A | 2/1998 | Bello |
| 5,719,122 A | 2/1998 | Chiodini et al. |
| 5,719,197 A | 2/1998 | Kanios et al. |
| 5,725,872 A | 3/1998 | Stamm et al. |
| 5,725,874 A | 3/1998 | Oda |
| 5,730,964 A | 3/1998 | Waldstreicher |
| 5,733,558 A | 3/1998 | Breton et al. |
| 5,733,572 A | 3/1998 | Unger et al. |
| 5,747,049 A | 5/1998 | Tominaga |
| 5,753,241 A | 5/1998 | Ribier et al. |
| 5,753,245 A | 5/1998 | Fowler et al. |
| 5,753,270 A | 5/1998 | Beauchamp et al. |
| 5,759,520 A | 6/1998 | Sachetto |
| 5,759,579 A | 6/1998 | Singh et al. |
| 5,767,104 A | 6/1998 | Bar-Shalom et al. |
| 5,773,410 A | 6/1998 | Yamamoto |
| 5,783,202 A | 7/1998 | Tomlinson et al. |
| 5,788,664 A | 8/1998 | Scalise |
| 5,792,448 A | 8/1998 | Dubief et al. |
| 5,792,922 A | 8/1998 | Moloney et al. |
| 5,797,955 A | 8/1998 | Walters |
| 5,804,546 A | 9/1998 | Hall et al. |
| 5,807,571 A | 9/1998 | List |
| 5,817,322 A | 10/1998 | Xu et al. |
| 5,824,650 A | 10/1998 | De Lacharriere et al. |
| 5,833,960 A | 11/1998 | Gers-Barlag et al. |
| 5,833,961 A | 11/1998 | Siegfried et al. |
| 5,837,270 A | 11/1998 | Burgess |
| 5,840,744 A | 11/1998 | Borgman |
| 5,840,771 A | 11/1998 | Oldham et al. |
| 5,843,411 A | 12/1998 | Hernandez et al. |
| 5,846,983 A | 12/1998 | Sandborn et al. |
| 5,849,042 A | 12/1998 | Lim et al. |
| 5,854,246 A | 12/1998 | Francois et al. |
| 5,856,452 A | 1/1999 | Moloney et al. |
| 5,858,371 A | 1/1999 | Singh et al. |
| 5,865,347 A | 2/1999 | Welschoff |
| 5,866,040 A | 2/1999 | Nakama et al. |
| 5,869,529 A | 2/1999 | Sintov et al. |
| 5,871,720 A | 2/1999 | Gutierrez et al. |
| 5,877,216 A | 3/1999 | Place et al. |
| 5,879,469 A | 3/1999 | Avram et al. |
| 5,881,493 A | 3/1999 | Restive |
| 5,885,581 A | 3/1999 | Massand |
| 5,889,028 A | 3/1999 | Sandborn et al. |
| 5,889,054 A | 3/1999 | Yu et al. |
| 5,891,458 A | 4/1999 | Britton et al. |
| 5,902,574 A | 5/1999 | Stoner et al. |
| 5,902,789 A | 5/1999 | Stoltz |
| 5,905,092 A | 5/1999 | Osborne et al. |
| 5,910,382 A | 6/1999 | Goodenough et al. |
| 5,911,981 A | 6/1999 | Dahms et al. |
| 5,912,007 A | 6/1999 | Pan et al. |
| 5,914,122 A | 6/1999 | Otterbeck et al. |
| 5,914,310 A | 6/1999 | Li et al. |
| 5,919,830 A | 7/1999 | Gopalkrishnan et al. |
| 5,922,331 A | 7/1999 | Mausner |
| 5,925,669 A | 7/1999 | Katz et al. |
| 5,939,376 A | 8/1999 | Durbut et al. |
| 5,948,682 A | 9/1999 | Moloney |
| 5,951,544 A | 9/1999 | Konwitz |
| 5,951,989 A | 9/1999 | Heymann |
| 5,951,993 A | 9/1999 | Scholz et al. |
| 5,952,373 A | 9/1999 | Lanzendorfer et al. |
| 5,952,392 A | 9/1999 | Katz et al. |
| 5,955,414 A | 9/1999 | Brown et al. |
| 5,959,161 A | 9/1999 | Kenmochi et al. |
| 5,961,957 A | 10/1999 | McAnalley |
| 5,961,998 A | 10/1999 | Arnaud et al. |
| 5,972,310 A | 10/1999 | Sachetto |
| 5,976,555 A | 11/1999 | Liu et al. |
| 5,980,904 A | 11/1999 | Leverett et al. |
| 5,990,100 A | 11/1999 | Rosenberg et al. |
| 5,993,846 A | 11/1999 | Friedman et al. |
| 6,001,341 A | 12/1999 | Genova et al. |
| 6,006,948 A | 12/1999 | Auer |
| 6,017,912 A | 1/2000 | Bussell |
| 6,019,967 A | 2/2000 | Breton et al. |
| 6,024,942 A | 2/2000 | Tanner et al. |
| 6,030,630 A | 2/2000 | Fleury et al. |
| 6,033,647 A | 3/2000 | Touzan et al. |
| 6,039,936 A | 3/2000 | Restle et al. |
| 6,042,848 A | 3/2000 | Lawyer et al. |
| 6,045,779 A | 4/2000 | Mueller et al. |

(56) References Cited

U.S. PATENT DOCUMENTS

| | | |
|---|---|---|
| 6,060,041 A | 5/2000 | Candau et al. |
| 6,071,536 A | 6/2000 | Suzuki et al. |
| 6,071,541 A | 6/2000 | Murad |
| 6,075,056 A | 6/2000 | Quigley, Jr. et al. |
| 6,080,394 A | 6/2000 | Lin et al. |
| 6,087,310 A | 7/2000 | Heinkel |
| 6,087,317 A | 7/2000 | Gee |
| 6,090,772 A | 7/2000 | Kaiser et al. |
| 6,093,408 A | 7/2000 | Hasenoehrl et al. |
| 6,096,756 A | 8/2000 | Crain et al. |
| 6,110,477 A | 8/2000 | Hernandez et al. |
| 6,110,966 A | 8/2000 | Pollock |
| 6,113,888 A | 9/2000 | Castro et al. |
| 6,116,466 A | 9/2000 | Gueret |
| 6,121,210 A | 9/2000 | Taylor |
| 6,126,920 A | 10/2000 | Jones et al. |
| 6,133,327 A | 10/2000 | Kimura et al. |
| 6,140,355 A | 10/2000 | Egidio et al. |
| 6,146,645 A | 11/2000 | Deckers et al. |
| 6,146,664 A | 11/2000 | Siddiqui |
| 6,162,834 A | 12/2000 | Sebillotte-Arnaud et al. |
| 6,165,455 A | 12/2000 | Torgerson et al. |
| 6,168,576 B1 | 1/2001 | Reynolds |
| 6,171,347 B1 | 1/2001 | Kunz et al. |
| 6,180,662 B1 | 1/2001 | Lanzendörfer et al. |
| 6,180,669 B1 | 1/2001 | Tamarkin |
| 6,183,762 B1 | 2/2001 | Deckers et al. |
| 6,186,367 B1 | 2/2001 | Harrold |
| 6,187,290 B1 | 2/2001 | Gilchrist et al. |
| 6,189,810 B1 | 2/2001 | Nerushai et al. |
| 6,190,365 B1 | 2/2001 | Abbott et al. |
| 6,204,285 B1 | 3/2001 | Fabiano et al. |
| 6,210,656 B1 | 4/2001 | Touzan et al. |
| 6,210,742 B1 | 4/2001 | Deckers et al. |
| 6,214,318 B1 | 4/2001 | Osipow et al. |
| 6,214,788 B1 | 4/2001 | Velazco et al. |
| 6,217,887 B1 | 4/2001 | Beerse et al. |
| 6,221,381 B1 | 4/2001 | Shelford et al. |
| 6,221,823 B1 | 4/2001 | Crisanti et al. |
| 6,224,888 B1 | 5/2001 | Vatter et al. |
| 6,231,837 B1 | 5/2001 | Stroud et al. |
| 6,232,315 B1 | 5/2001 | Shafer et al. |
| 6,241,971 B1 | 6/2001 | Fox et al. |
| 6,251,369 B1 | 6/2001 | Stoltz |
| 6,258,374 B1 | 7/2001 | Friess et al. |
| 6,261,544 B1 | 7/2001 | Coury et al. |
| 6,264,964 B1 | 7/2001 | Mohammadi |
| 6,270,781 B1 | 8/2001 | Gehlsen |
| 6,271,295 B1 | 8/2001 | Powell et al. |
| 6,274,150 B1 | 8/2001 | Simonnet et al. |
| 6,283,336 B1 | 9/2001 | Dwyer et al. |
| 6,284,802 B1 | 9/2001 | Bissett et al. |
| 6,287,546 B1 | 9/2001 | Reich et al. |
| 6,294,550 B1 | 9/2001 | Place et al. |
| 6,299,023 B1 | 10/2001 | Arnone |
| 6,299,032 B1 | 10/2001 | Hamilton |
| 6,299,900 B1 | 10/2001 | Reed et al. |
| 6,305,578 B1 | 10/2001 | Hildebrandt et al. |
| 6,306,841 B1 | 10/2001 | Place et al. |
| 6,308,863 B1 | 10/2001 | Harman |
| 6,319,913 B1 | 11/2001 | Mak et al. |
| 6,328,950 B1 | 12/2001 | Franzke et al. |
| 6,328,982 B1 | 12/2001 | Shiroyama et al. |
| 6,333,362 B1 | 12/2001 | Lorant |
| 6,335,022 B1 | 1/2002 | Simonnet et al. |
| 6,341,717 B2 | 1/2002 | Auer |
| 6,344,218 B1 | 2/2002 | Dodd et al. |
| 6,348,229 B1 | 2/2002 | Eini et al. |
| 6,352,727 B1 | 3/2002 | Takahashi |
| 6,355,230 B2 | 3/2002 | Gers-Barlag et al. |
| 6,358,541 B1 | 3/2002 | Goodman |
| 6,358,924 B1 | 3/2002 | Hoffmann |
| 6,364,854 B1 | 4/2002 | Ferrer et al. |
| 6,372,234 B1 | 4/2002 | Deckers et al. |
| 6,375,936 B1 | 4/2002 | Allard et al. |
| 6,375,960 B1 | 4/2002 | Simonnet et al. |
| 6,383,471 B1 | 5/2002 | Chen et al. |
| 6,395,258 B1 | 5/2002 | Steer |
| 6,395,300 B1 | 5/2002 | Straub et al. |
| 6,403,061 B1 | 6/2002 | Candau et al. |
| 6,403,069 B1 | 6/2002 | Chopra et al. |
| 6,410,036 B1 | 6/2002 | De Rosa et al. |
| 6,423,323 B2 | 7/2002 | Neubourg |
| 6,423,329 B1 | 7/2002 | Sine et al. |
| 6,428,772 B1 | 8/2002 | Singh et al. |
| 6,433,003 B1 | 8/2002 | Bobrove et al. |
| 6,433,024 B1 | 8/2002 | Popp et al. |
| 6,433,033 B1 | 8/2002 | Isobe et al. |
| 6,433,068 B1 | 8/2002 | Morrison et al. |
| 6,437,006 B1 | 8/2002 | Yoon et al. |
| 6,440,429 B1 | 8/2002 | Torizuka et al. |
| 6,447,801 B1 | 9/2002 | Salafsky et al. |
| 6,451,777 B1 | 9/2002 | Bradbury et al. |
| 6,455,076 B1 | 9/2002 | Hahn et al. |
| 6,468,989 B1 | 10/2002 | Chang et al. |
| 6,479,058 B1 | 11/2002 | McCadden |
| 6,479,060 B1 | 11/2002 | Jones et al. |
| 6,479,532 B1 | 11/2002 | Kamimura et al. |
| 6,482,810 B1 | 11/2002 | Brem et al. |
| 6,486,168 B1 | 11/2002 | Skwierczynski et al. |
| 6,488,947 B1 | 12/2002 | Bekele |
| 6,511,655 B1 | 1/2003 | Muller et al. |
| 6,514,487 B1 | 2/2003 | Barr |
| 6,524,594 B1 | 2/2003 | Santora et al. |
| 6,531,118 B1 | 3/2003 | Gonzalez et al. |
| 6,534,455 B1 | 3/2003 | Maurin et al. |
| 6,536,629 B2 | 3/2003 | van der Heijden |
| 6,544,530 B1 | 4/2003 | Friedman |
| 6,544,562 B2 | 4/2003 | Singh et al. |
| 6,547,063 B1 | 4/2003 | Zaveri et al. |
| 6,548,074 B1 | 4/2003 | Mohammadi |
| 6,551,604 B1 | 4/2003 | Beck et al. |
| 6,562,355 B1 | 5/2003 | Renault |
| 6,566,350 B2 | 5/2003 | Ono et al. |
| 6,582,679 B2 | 6/2003 | Stein et al. |
| 6,582,710 B2 | 6/2003 | Deckers et al. |
| 6,589,509 B2 | 7/2003 | Keller et al. |
| 6,596,287 B2 | 7/2003 | Deckers et al. |
| 6,599,513 B2 | 7/2003 | Deckers et al. |
| 6,607,716 B1 | 8/2003 | Smith et al. |
| 6,610,315 B2 | 8/2003 | Scholz et al. |
| 6,620,773 B1 | 9/2003 | Stork et al. |
| 6,638,981 B2 | 10/2003 | Williams et al. |
| 6,649,571 B1 | 11/2003 | Morgan |
| 6,649,574 B2 | 11/2003 | Cardis et al. |
| 6,672,483 B1 | 1/2004 | Roy |
| 6,682,726 B2 | 1/2004 | Marchesi et al. |
| 6,682,750 B2 | 1/2004 | Loeffler et al. |
| 6,691,898 B2 | 2/2004 | Hurray et al. |
| 6,706,290 B1 | 3/2004 | Kajander et al. |
| 6,709,663 B2 | 3/2004 | Espinoza |
| 6,723,309 B2 | 4/2004 | Deane |
| 6,730,288 B1 | 5/2004 | Abram |
| 6,736,860 B2 | 5/2004 | Patel et al. |
| 6,753,000 B2 | 6/2004 | Breton et al. |
| 6,753,013 B1 | 6/2004 | Didriksen et al. |
| 6,753,167 B2 | 6/2004 | Moloney et al. |
| 6,762,158 B2 | 7/2004 | Lukenbach et al. |
| 6,765,001 B2 | 7/2004 | Gans et al. |
| 6,774,114 B2 | 8/2004 | Castiel et al. |
| 6,777,591 B1 | 8/2004 | Chaudhary et al. |
| 6,790,435 B1 | 9/2004 | Ma et al. |
| 6,796,973 B1 | 9/2004 | Contente et al. |
| RE38,623 E | 10/2004 | Hernandez et al. |
| 6,811,767 B1 | 11/2004 | Bosch et al. |
| 6,834,778 B2 | 12/2004 | Jinbo et al. |
| 6,841,547 B2 | 1/2005 | Brown et al. |
| 6,843,390 B1 | 1/2005 | Bristor |
| 6,875,438 B2 | 4/2005 | Kraemer et al. |
| 6,881,271 B2 | 4/2005 | Ochiai |
| 6,890,567 B2 | 5/2005 | Nakatsu et al. |
| 6,897,195 B2 | 5/2005 | Su et al. |
| 6,902,737 B2 | 6/2005 | Quemin et al. |
| 6,911,211 B2 | 6/2005 | Eini et al. |

(56) References Cited

U.S. PATENT DOCUMENTS

| | | |
|---|---|---|
| 6,914,057 B1 | 7/2005 | Ryan et al. |
| 6,946,120 B2 | 9/2005 | Wai-Chiu So et al. |
| 6,946,139 B2 | 9/2005 | Henning |
| 6,951,654 B2 | 10/2005 | Malcolm et al. |
| 6,955,816 B2 | 10/2005 | Klysz |
| 6,956,062 B2 | 10/2005 | Beilfuss et al. |
| 6,958,154 B2 | 10/2005 | Andolino Brandt et al. |
| 6,967,023 B1 | 11/2005 | Eini et al. |
| 6,968,982 B1 | 11/2005 | Burns |
| 6,969,521 B1 | 11/2005 | Gonzalez et al. |
| RE38,964 E | 1/2006 | Shillington |
| 6,986,883 B2 | 1/2006 | Pellico |
| 6,994,863 B2 | 2/2006 | Eini et al. |
| 7,002,486 B2 | 2/2006 | Lawrence |
| 7,014,844 B2 | 3/2006 | Mahalingam et al. |
| 7,021,499 B2 | 4/2006 | Hansen et al. |
| 7,029,659 B2 | 4/2006 | Abram |
| 7,060,253 B1 | 6/2006 | Mundschenk |
| 7,078,058 B2 | 7/2006 | Jones et al. |
| 7,083,799 B1 | 8/2006 | Giacomoni |
| 7,137,536 B2 | 11/2006 | Walters et al. |
| 7,195,135 B1 | 3/2007 | Garcia |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |
| 7,252,816 B1 | 8/2007 | Angel et al. |
| 7,270,828 B2 | 9/2007 | Masuda et al. |
| 7,455,195 B2 | 11/2008 | Meketa |
| 7,497,354 B2 | 3/2009 | Decottignies et al. |
| 7,575,739 B2 | 8/2009 | Tamarkin et al. |
| 7,645,803 B2 | 1/2010 | Tamarkin et al. |
| 7,654,415 B2 | 2/2010 | van der Heijden |
| 7,682,623 B2 | 3/2010 | Eini et al. |
| 7,700,076 B2 | 4/2010 | Tamarkin et al. |
| 7,704,518 B2 | 4/2010 | Tamarkin et al. |
| 7,758,888 B2 | 7/2010 | Lapidot et al. |
| 7,793,807 B2 | 9/2010 | Goujon et al. |
| 7,820,145 B2 | 10/2010 | Tamarkin et al. |
| 7,842,791 B2 | 11/2010 | Britten et al. |
| 7,960,416 B2 | 6/2011 | Sato et al. |
| 8,114,385 B2 | 2/2012 | Tamarkin et al. |
| 8,119,106 B2 | 2/2012 | Tamarkin et al. |
| 8,119,109 B2 | 2/2012 | Tamarkin et al. |
| 8,119,150 B2 | 2/2012 | Tamarkin et al. |
| 8,158,109 B2 | 4/2012 | Abram et al. |
| 8,192,749 B2 | 6/2012 | Ashley |
| 8,211,874 B2 | 7/2012 | Theobald et al. |
| 8,343,945 B2 | 1/2013 | Tamarkin et al. |
| 8,362,091 B2 | 1/2013 | Tamarkin et al. |
| 8,435,498 B2 | 5/2013 | Tamarkin et al. |
| 8,486,374 B2 | 7/2013 | Tamarkin et al. |
| 8,486,375 B2 | 7/2013 | Tamarkin et al. |
| 8,486,376 B2 | 7/2013 | Friedman et al. |
| 8,512,718 B2 | 8/2013 | Eini et al. |
| 8,518,376 B2 | 8/2013 | Tamarkin et al. |
| 8,518,378 B2 | 8/2013 | Tamarkin et al. |
| 8,592,380 B2 | 11/2013 | Trumbore et al. |
| 8,617,100 B2 | 12/2013 | Eini et al. |
| 8,618,081 B2 | 12/2013 | Tamarkin et al. |
| 8,623,330 B2 | 1/2014 | Gurge et al. |
| 8,636,982 B2 | 1/2014 | Tamarkin et al. |
| 8,652,443 B2 | 2/2014 | Varanasi et al. |
| 8,703,105 B2 | 4/2014 | Tamarkin et al. |
| 8,709,385 B2 | 4/2014 | Tamarkin et al. |
| 8,722,021 B2 | 5/2014 | Friedman et al. |
| 8,735,377 B1 | 5/2014 | Sipos |
| 8,741,265 B2 | 6/2014 | Tamarkin et al. |
| 8,778,365 B1 | 7/2014 | Hardas et al. |
| 8,784,780 B2 | 7/2014 | Gurge et al. |
| 8,795,635 B2 | 8/2014 | Tamarkin et al. |
| 8,795,693 B2 | 8/2014 | Tamarkin et al. |
| 8,840,869 B2 | 9/2014 | Friedman et al. |
| 8,846,039 B2 | 9/2014 | Chung et al. |
| 8,865,139 B1 | 10/2014 | Tamarkin et al. |
| 8,871,184 B2 | 10/2014 | Tamarkin et al. |
| 8,895,536 B2 | 11/2014 | Bannister et al. |
| 8,900,553 B2 | 12/2014 | Tamarkin et al. |
| 8,900,554 B2 | 12/2014 | Tamarkin et al. |
| 8,945,516 B2 | 2/2015 | Tamarkin et al. |
| 8,992,896 B2 | 3/2015 | Tamarkin et al. |
| 9,050,253 B2 | 6/2015 | Tamarkin et al. |
| 9,072,667 B2 | 7/2015 | Tamarkin et al. |
| 9,101,662 B2 | 8/2015 | Tamarkin et al. |
| 9,161,916 B2 | 10/2015 | Tamarkin et al. |
| 9,167,813 B2 | 10/2015 | Tamarkin et al. |
| 9,192,558 B2 | 11/2015 | Chen et al. |
| 9,211,259 B2 | 12/2015 | Friedman et al. |
| 9,265,725 B2 | 2/2016 | Tamarkin et al. |
| 9,265,740 B2 | 2/2016 | Johnston et al. |
| 9,271,930 B2 | 3/2016 | At |
| 9,320,705 B2 | 4/2016 | Tamarkin et al. |
| 9,439,857 B2 | 9/2016 | Tamarkin et al. |
| 9,474,720 B2 | 10/2016 | Yamamoto |
| 9,492,412 B2 | 11/2016 | Tamarkin et al. |
| 9,539,208 B2 | 1/2017 | Tamarkin et al. |
| 9,539,266 B2 | 1/2017 | Mansouri |
| 9,549,898 B2 | 1/2017 | Tamarkin et al. |
| 9,572,775 B2 | 2/2017 | Tamarkin et al. |
| 9,592,246 B2 | 3/2017 | Salman et al. |
| 9,622,947 B2 | 4/2017 | Tamarkin et al. |
| 9,636,405 B2 | 5/2017 | Tamarkin et al. |
| 9,662,298 B2 | 5/2017 | Tamarkin et al. |
| 9,668,972 B2 | 6/2017 | Tamarkin et al. |
| 9,675,700 B2 | 6/2017 | Tamarkin et al. |
| 9,682,021 B2 | 6/2017 | Tamarkin et al. |
| 9,713,643 B2 | 7/2017 | Friedman et al. |
| 9,795,564 B2 | 10/2017 | Tamarkin et al. |
| 9,849,142 B2 | 12/2017 | Tamarkin et al. |
| 9,884,017 B2 | 2/2018 | Tamarkin et al. |
| 9,931,328 B2 | 4/2018 | Kandavilli et al. |
| 10,029,013 B2 | 7/2018 | Tamarkin et al. |
| 10,086,080 B2 | 10/2018 | Tamarkin et al. |
| 10,137,200 B2 | 11/2018 | Tamarkin et al. |
| 2001/0006654 A1 | 7/2001 | Cannell et al. |
| 2001/0027218 A1 | 10/2001 | Stern et al. |
| 2001/0027981 A1 | 10/2001 | Yquel |
| 2001/0033838 A1 | 10/2001 | Farmer |
| 2001/0036450 A1 | 11/2001 | Verite et al. |
| 2001/0054574 A1 | 12/2001 | Navarro |
| 2002/0004063 A1 | 1/2002 | Zhang |
| 2002/0013481 A1 | 1/2002 | Schonrock et al. |
| 2002/0015721 A1 | 2/2002 | Simonnet et al. |
| 2002/0031478 A1 | 3/2002 | Keller et al. |
| 2002/0032171 A1 | 3/2002 | Chen et al. |
| 2002/0035046 A1 | 3/2002 | Lukenbach et al. |
| 2002/0035070 A1 | 3/2002 | Gardlik et al. |
| 2002/0035087 A1 | 3/2002 | Barclay |
| 2002/0035182 A1 | 3/2002 | L'Alloret et al. |
| 2002/0039591 A1 | 4/2002 | Dahle |
| 2002/0044659 A1 | 4/2002 | Ohta |
| 2002/0045659 A1 | 4/2002 | Michelet et al. |
| 2002/0048798 A1 | 4/2002 | Avery et al. |
| 2002/0058010 A1 | 5/2002 | Picard-Lesboueyries et al. |
| 2002/0072544 A1 | 6/2002 | Miller et al. |
| 2002/0090386 A1 | 7/2002 | Halswanter et al. |
| 2002/0098215 A1 | 7/2002 | Douin et al. |
| 2002/0111281 A1 | 8/2002 | Vishnupad |
| 2002/0117516 A1 | 8/2002 | Lasserre et al. |
| 2002/0134376 A1 | 9/2002 | Castro et al. |
| 2002/0136755 A1 | 9/2002 | Tyrrell et al. |
| 2002/0143188 A1 | 10/2002 | Garvey et al. |
| 2002/0153390 A1 | 10/2002 | Vlodek |
| 2002/0165170 A1 | 11/2002 | Wilson et al. |
| 2002/0182162 A1 | 12/2002 | Shahinpoor et al. |
| 2002/0182234 A1 | 12/2002 | Riedel et al. |
| 2002/0187181 A1 | 12/2002 | Godbey et al. |
| 2002/0198136 A1 | 12/2002 | Mak et al. |
| 2003/0006193 A1 | 1/2003 | Ikeda et al. |
| 2003/0013692 A1 | 1/2003 | Gullans et al. |
| 2003/0017181 A1 | 1/2003 | Rood et al. |
| 2003/0031693 A1 | 2/2003 | Breton et al. |
| 2003/0053961 A1 | 3/2003 | Eccard |
| 2003/0077297 A1 | 4/2003 | Chen et al. |

(56) References Cited

U.S. PATENT DOCUMENTS

| | | |
|---|---|---|
| 2003/0077301 A1 | 4/2003 | Maibach et al. |
| 2003/0078172 A1 | 4/2003 | Guiramand et al. |
| 2003/0082120 A1 | 5/2003 | Milstein |
| 2003/0108502 A1 | 6/2003 | Uchida et al. |
| 2003/0114520 A1 | 6/2003 | Pereira et al. |
| 2003/0118515 A1 | 6/2003 | Jew et al. |
| 2003/0118527 A1 | 6/2003 | Jager et al. |
| 2003/0129259 A1 | 7/2003 | Mahalingam et al. |
| 2003/0130247 A1 | 7/2003 | Gans et al. |
| 2003/0148949 A1 | 8/2003 | Podolsky |
| 2003/0175232 A1 | 9/2003 | Elliott et al. |
| 2003/0175315 A1 | 9/2003 | Yoo et al. |
| 2003/0180347 A1 | 9/2003 | Young et al. |
| 2003/0185839 A1 | 10/2003 | Podolsky |
| 2003/0185861 A1 | 10/2003 | Hori et al. |
| 2003/0194379 A1 | 10/2003 | Brugger et al. |
| 2003/0195128 A1 | 10/2003 | Deckman et al. |
| 2003/0206955 A1 | 11/2003 | Sonneville-Aubrun et al. |
| 2003/0215418 A1 | 11/2003 | Asmus et al. |
| 2003/0215472 A1 | 11/2003 | Bonda et al. |
| 2003/0235597 A1 | 12/2003 | Withiam et al. |
| 2004/0002550 A1 | 1/2004 | Mecurio |
| 2004/0018228 A1 | 1/2004 | Fischell et al. |
| 2004/0028752 A1 | 2/2004 | Kamm et al. |
| 2004/0038912 A1 | 2/2004 | Michelet et al. |
| 2004/0053797 A1 | 3/2004 | Chen et al. |
| 2004/0058878 A1 | 3/2004 | Walker |
| 2004/0063787 A1 | 4/2004 | Villanueva |
| 2004/0067970 A1 | 4/2004 | Foster et al. |
| 2004/0072638 A1 | 4/2004 | Enos et al. |
| 2004/0076651 A1 | 4/2004 | Brocks et al. |
| 2004/0078896 A1 | 4/2004 | Hellyer et al. |
| 2004/0079361 A1 | 4/2004 | Clayton et al. |
| 2004/0105825 A1 | 6/2004 | Henning |
| 2004/0106688 A1 | 6/2004 | Koike et al. |
| 2004/0120917 A1 | 6/2004 | Perrier et al. |
| 2004/0127554 A1 | 7/2004 | Ghisalberti |
| 2004/0138179 A1 | 7/2004 | Goldstein et al. |
| 2004/0151671 A1 | 8/2004 | Abram et al. |
| 2004/0151756 A1 | 8/2004 | Richards et al. |
| 2004/0161447 A1 | 8/2004 | Paul |
| 2004/0184992 A1 | 9/2004 | Abram |
| 2004/0185123 A1 | 9/2004 | Mazzio et al. |
| 2004/0191196 A1 | 9/2004 | Tamarkin |
| 2004/0192754 A1 | 9/2004 | Shapira et al. |
| 2004/0195276 A1 | 10/2004 | Fuchs |
| 2004/0197276 A1 | 10/2004 | Takase et al. |
| 2004/0197295 A1 | 10/2004 | Riedel et al. |
| 2004/0198706 A1 | 10/2004 | Carrara |
| 2004/0219176 A1 | 11/2004 | Dominguez |
| 2004/0220187 A1 | 11/2004 | Stephenson et al. |
| 2004/0229813 A1 | 11/2004 | DiPiano et al. |
| 2004/0234475 A1 | 11/2004 | Lannibois-Drean et al. |
| 2004/0241099 A1 | 12/2004 | Popp et al. |
| 2004/0247531 A1 | 12/2004 | Riedel et al. |
| 2004/0258627 A1 | 12/2004 | Riedel et al. |
| 2004/0258628 A1 | 12/2004 | Riedel et al. |
| 2004/0258643 A1 | 12/2004 | Yaqub et al. |
| 2005/0002976 A1 | 1/2005 | Wu |
| 2005/0013853 A1 | 1/2005 | Gil-Ad et al. |
| 2005/0042182 A1 | 2/2005 | Arkin et al. |
| 2005/0054991 A1 | 3/2005 | Tobyn et al. |
| 2005/0069566 A1 | 3/2005 | Tamarkin et al. |
| 2005/0075407 A1 | 4/2005 | Tamarkin et al. |
| 2005/0079139 A1 | 4/2005 | Jacques et al. |
| 2005/0079228 A1 | 4/2005 | Jaiswal et al. |
| 2005/0084551 A1 | 4/2005 | Jensen et al. |
| 2005/0085843 A1 | 4/2005 | Opolski et al. |
| 2005/0100517 A1 | 5/2005 | Sanzgiri et al. |
| 2005/0101936 A1 | 5/2005 | Gonzales et al. |
| 2005/0106197 A1 | 5/2005 | Blin et al. |
| 2005/0123494 A1 | 6/2005 | Swaile et al. |
| 2005/0123496 A1 | 6/2005 | Shah et al. |
| 2005/0148552 A1 | 7/2005 | Ryan et al. |
| 2005/0153943 A1 | 7/2005 | Ashley |
| 2005/0164993 A1 | 7/2005 | Ashley |
| 2005/0186142 A1 | 8/2005 | Tamarkin et al. |
| 2005/0186147 A1 | 8/2005 | Tamarkin et al. |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0207837 A1 | 9/2005 | Kosh et al. |
| 2005/0222090 A1 | 10/2005 | Cheng et al. |
| 2005/0232869 A1 | 10/2005 | Tamarkin et al. |
| 2005/0244354 A1 | 11/2005 | Speron |
| 2005/0245902 A1 | 11/2005 | Cornish et al. |
| 2005/0252995 A1 | 11/2005 | Westphal et al. |
| 2005/0255048 A1 | 11/2005 | Hirsh et al. |
| 2005/0258189 A1 | 11/2005 | Peterson et al. |
| 2005/0266035 A1 | 12/2005 | Healy et al. |
| 2005/0268416 A1 | 12/2005 | Sommers |
| 2005/0271596 A1 | 12/2005 | Friedman et al. |
| 2005/0276836 A1 | 12/2005 | Wilson et al. |
| 2005/0281749 A1 | 12/2005 | Willcox et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0018937 A1 | 1/2006 | Friedman et al. |
| 2006/0018938 A1 | 1/2006 | Neubourg |
| 2006/0029565 A1 | 2/2006 | Xu et al. |
| 2006/0051301 A1 | 3/2006 | Galopin et al. |
| 2006/0054634 A1 | 3/2006 | Meketa |
| 2006/0057168 A1 | 3/2006 | Larm et al. |
| 2006/0099151 A1 | 5/2006 | Neubourg |
| 2006/0108377 A1 | 5/2006 | Glynn et al. |
| 2006/0110415 A1 | 5/2006 | Gupta |
| 2006/0110418 A1 | 5/2006 | Johnson |
| 2006/0114745 A1 | 6/2006 | Ollmann et al. |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1 | 11/2006 | Friedman et al. |
| 2006/0272199 A1 | 12/2006 | Licciardello et al. |
| 2006/0285912 A1 | 12/2006 | Eini et al. |
| 2006/0292080 A1 | 12/2006 | Abram et al. |
| 2007/0009607 A1 | 1/2007 | Jones |
| 2007/0010580 A1 | 1/2007 | De Paoli Ambrosi |
| 2007/0015739 A1 | 1/2007 | Walker et al. |
| 2007/0017696 A1 | 1/2007 | Lin et al. |
| 2007/0020213 A1 | 1/2007 | Tamarkin et al. |
| 2007/0020304 A1 | 1/2007 | Tamarkin et al. |
| 2007/0027055 A1 | 2/2007 | Koivisto et al. |
| 2007/0036831 A1 | 2/2007 | Baker |
| 2007/0053943 A1 | 3/2007 | Wang et al. |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0111956 A1 | 5/2007 | Matsushima et al. |
| 2007/0134174 A1 | 6/2007 | Irwin et al. |
| 2007/0140998 A1 | 6/2007 | Kato et al. |
| 2007/0140999 A1 | 6/2007 | Puglia et al. |
| 2007/0141086 A1 | 6/2007 | Ohara et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0160548 A1 | 7/2007 | Riccardi et al. |
| 2007/0166274 A1 | 7/2007 | Mazur et al. |
| 2007/0224143 A1 | 9/2007 | Konis |

(56) References Cited

U.S. PATENT DOCUMENTS

| | | |
|---|---|---|
| 2007/0237724 A1 | 10/2007 | Abram et al. |
| 2007/0264317 A1 | 11/2007 | Yosha et al. |
| 2007/0271235 A1 | 11/2007 | Frank et al. |
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0008397 A1 | 1/2008 | Kisilev |
| 2008/0015263 A1 | 1/2008 | Bolotin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0050317 A1 | 2/2008 | Tamarkin et al. |
| 2008/0058055 A1 | 3/2008 | LeMay et al. |
| 2008/0063682 A1 | 3/2008 | Cashman et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0181854 A1 | 7/2008 | Eini et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0255498 A1 | 10/2008 | Houle |
| 2008/0260655 A1 | 10/2008 | Tamarkin et al. |
| 2008/0292560 A1 | 11/2008 | Tamarkin et al. |
| 2008/0311167 A1 | 12/2008 | Oronsky et al. |
| 2008/0317679 A1 | 12/2008 | Tamarkin et al. |
| 2009/0017147 A1 | 1/2009 | Lintner et al. |
| 2009/0053290 A1 | 2/2009 | Sand et al. |
| 2009/0061001 A1 | 3/2009 | Hougaz |
| 2009/0093514 A1 | 4/2009 | Statham et al. |
| 2009/0130029 A1 | 5/2009 | Tamarkin et al. |
| 2009/0131488 A1 | 5/2009 | Harel et al. |
| 2009/0175799 A1 | 7/2009 | Tamarkin et al. |
| 2009/0214628 A1 | 8/2009 | De Rijk |
| 2009/0291917 A1 | 11/2009 | Akama et al. |
| 2010/0111879 A1 | 5/2010 | Tamarkin et al. |
| 2010/0221194 A1 | 9/2010 | Loupenok |
| 2010/0247449 A1 | 9/2010 | Graupe et al. |
| 2010/0286417 A1 | 11/2010 | Mendes et al. |
| 2011/0002969 A1 | 1/2011 | Serraima et al. |
| 2011/0097279 A1 | 4/2011 | Tamarkin et al. |
| 2011/0207765 A1 | 8/2011 | Van Den Bussche et al. |
| 2011/0262542 A1 | 10/2011 | Ashley |
| 2012/0064136 A1 | 3/2012 | Baker, Jr. et al. |
| 2012/0082632 A1 | 4/2012 | Phillips et al. |
| 2012/0087872 A1 | 4/2012 | Tamarkin et al. |
| 2012/0128598 A1 | 5/2012 | Trumbore et al. |
| 2012/0141384 A1 | 6/2012 | Tamarkin |
| 2012/0148503 A1 | 6/2012 | Tamarkin et al. |
| 2012/0156144 A1 | 6/2012 | Tamarkin et al. |
| 2012/0164087 A1 | 6/2012 | Carter |
| 2012/0181201 A1 | 7/2012 | Heggie |
| 2012/0237453 A1 | 9/2012 | Tamarkin et al. |
| 2013/0053353 A1 | 2/2013 | Tamarkin et al. |
| 2013/0115173 A1 | 5/2013 | Trumbore et al. |
| 2013/0161351 A1 | 6/2013 | Eini et al. |
| 2013/0164225 A1 | 6/2013 | Tamarkin et al. |
| 2013/0189195 A1 | 7/2013 | Tamarkin et al. |
| 2013/0189196 A1 | 7/2013 | Tamarkin et al. |
| 2013/0251644 A1 | 9/2013 | Majhi et al. |
| 2013/0261565 A1 | 10/2013 | Wong et al. |
| 2013/0295022 A1 | 11/2013 | Friedman et al. |
| 2013/0296387 A1 | 11/2013 | Saad |
| 2014/0066524 A1 | 3/2014 | Tamarkin et al. |
| 2014/0086848 A1 | 3/2014 | Tamarkin et al. |
| 2014/0121188 A1 | 5/2014 | Tamarkin et al. |
| 2014/0140937 A1 | 5/2014 | Gurge et al. |
| 2014/0182585 A1 | 7/2014 | Tamarkin et al. |
| 2014/0186269 A1 | 7/2014 | Tamarkin et al. |
| 2014/0221320 A1 | 8/2014 | Joks et al. |
| 2014/0228355 A1 | 8/2014 | Kortagere et al. |
| 2014/0242016 A1 | 8/2014 | Binks et al. |
| 2014/0248219 A1 | 9/2014 | Tamarkin et al. |
| 2015/0025060 A1 | 1/2015 | Tamarkin et al. |
| 2015/0098907 A1 | 4/2015 | Tamarkin et al. |
| 2015/0141381 A1 | 5/2015 | Levy et al. |
| 2015/0157586 A1 | 6/2015 | Tamarkin et al. |
| 2015/0164922 A1 | 6/2015 | Tamarkin et al. |
| 2015/0174144 A1 | 6/2015 | Bowser et al. |
| 2015/0196570 A1 | 7/2015 | Tamarkin et al. |
| 2015/0209296 A1 | 7/2015 | Yamamoto |
| 2015/0374625 A1 | 12/2015 | Tamarkin et al. |
| 2016/0101184 A1 | 4/2016 | Tamarkin et al. |
| 2016/0128944 A1 | 5/2016 | Chawrai et al. |
| 2016/0158261 A1 | 6/2016 | Friedman et al. |
| 2016/0213757 A1 | 7/2016 | Edelson et al. |
| 2016/0279152 A1 | 9/2016 | Chen et al. |
| 2016/0287615 A1 | 10/2016 | Chan et al. |
| 2016/0354473 A1 | 12/2016 | Tamarkin et al. |
| 2016/0361252 A1 | 12/2016 | Franke |
| 2016/0361320 A1 | 12/2016 | Zhao et al. |
| 2017/0014517 A1 | 1/2017 | Tamarkin |
| 2017/0049712 A1 | 2/2017 | Bhalani et al. |
| 2017/0119665 A1 | 5/2017 | Tamarkin et al. |
| 2017/0157175 A1 | 6/2017 | Tamarkin et al. |
| 2017/0172857 A1 | 6/2017 | Tamarkin et al. |
| 2017/0181970 A1 | 6/2017 | Tamarkin et al. |
| 2017/0216334 A1 | 8/2017 | Tamarkin et al. |
| 2017/0231909 A1 | 8/2017 | Tamarkin et al. |
| 2017/0274084 A1 | 9/2017 | Friedman et al. |
| 2017/0340743 A1 | 11/2017 | Tamarkin et al. |
| 2017/0348418 A1 | 12/2017 | Tamarkin et al. |
| 2017/0354597 A1 | 12/2017 | Tamarkin et al. |
| 2018/0000734 A1 | 1/2018 | Tamarkin et al. |
| 2018/0064638 A1 | 3/2018 | Tamarkin et al. |
| 2018/0147218 A1 | 5/2018 | Tamarkin et al. |
| 2018/0153804 A1 | 6/2018 | Tamarkin et al. |
| 2018/0214558 A1 | 8/2018 | Tamarkin et al. |
| 2018/0235984 A1 | 8/2018 | Eini et al. |
| 2019/0000980 A1 | 1/2019 | Tamarkin et al. |
| 2019/0022000 A1 | 1/2019 | Tamarkin et al. |
| 2019/0022001 A1 | 1/2019 | Tamarkin et al. |
| 2019/0029958 A1 | 1/2019 | Tamarkin et al. |
| 2019/0054106 A1 | 2/2019 | Tamarkin et al. |
| 2019/0076339 A1 | 3/2019 | Tamarkin et al. |
| 2019/0076356 A1 | 3/2019 | Tamarkin et al. |
| 2019/0076451 A1 | 3/2019 | Friedman et al. |
| 2019/0091149 A1 | 3/2019 | Tamarkin et al. |
| 2019/0134203 A1 | 5/2019 | Tamarkin et al. |
| 2019/0134204 A1 | 5/2019 | Tamarkin et al. |

FOREIGN PATENT DOCUMENTS

| | | |
|---|---|---|
| CA | 2114537 A1 | 2/1993 |
| CA | 2154438 A1 | 1/1996 |
| CA | 2422244 A1 | 9/2003 |
| CA | 2502986 A1 | 5/2004 |
| CA | 2534372 A1 | 10/2005 |
| CH | 639913 A5 | 12/1983 |
| DE | 1 882 100 U | 11/1963 |
| DE | 1926796 A1 | 3/1970 |
| DE | 2 608 226 A1 | 9/1977 |
| DE | 4140474 A1 | 6/1993 |
| DE | 10009233 A1 | 8/2000 |
| DE | 10138495 A1 | 2/2003 |
| DE | 102004016710 A1 | 10/2005 |
| EP | 0 052 404 A2 | 5/1982 |
| EP | 0 156 507 A1 | 10/1985 |
| EP | 0 186 453 A2 | 7/1986 |
| EP | 0 213 827 A2 | 3/1987 |
| EP | 0 214 865 A2 | 3/1987 |
| EP | 0 270 316 A2 | 6/1988 |

(56) References Cited

FOREIGN PATENT DOCUMENTS

| | | |
|---|---|---|
| EP | 0 297 436 A2 | 1/1989 |
| EP | 0 336 812 A2 | 10/1989 |
| EP | 0 414 920 A1 | 3/1991 |
| EP | 0 211 550 B1 | 4/1991 |
| EP | 0 216 856 B1 | 7/1991 |
| EP | 0 454 102 A2 | 10/1991 |
| EP | 0 326 196 B2 | 3/1992 |
| EP | 0 484 530 A1 | 5/1992 |
| EP | 0 485 299 A1 | 5/1992 |
| EP | 0 488 089 A1 | 6/1992 |
| EP | 0 528 190 A1 | 2/1993 |
| EP | 0 552 612 A2 | 7/1993 |
| EP | 0 569 773 A2 | 11/1993 |
| EP | 0 404 376 B1 | 3/1994 |
| EP | 0 598 412 A2 | 5/1994 |
| EP | 0 391 124 B1 | 6/1995 |
| EP | 0 662 431 A2 | 7/1995 |
| EP | 0 535 327 B1 | 10/1996 |
| EP | 0 738 516 A1 | 10/1996 |
| EP | 0 757 959 A1 | 2/1997 |
| EP | 0 824 911 A2 | 2/1998 |
| EP | 0 829 259 A1 | 3/1998 |
| EP | 0 676 198 B1 | 10/1998 |
| EP | 0 979 654 A1 | 2/2000 |
| EP | 0 993 827 A1 | 4/2000 |
| EP | 1 025 836 A1 | 8/2000 |
| EP | 1 055 425 A2 | 11/2000 |
| EP | 0 506 197 B2 | 7/2001 |
| EP | 1 215 258 A2 | 6/2002 |
| EP | 1 287 813 A1 | 3/2003 |
| EP | 1 308 169 A1 | 5/2003 |
| EP | 1 375 386 A1 | 1/2004 |
| EP | 0 504 301 B1 | 3/2004 |
| EP | 1 428 521 A2 | 6/2004 |
| EP | 1 438 946 A1 | 7/2004 |
| EP | 1 189 579 B1 | 9/2004 |
| EP | 1 475 381 A1 | 11/2004 |
| EP | 1 500 385 A1 | 1/2005 |
| EP | 1 537 916 A1 | 6/2005 |
| EP | 1 600 185 A1 | 11/2005 |
| EP | 0 928 608 B1 | 3/2006 |
| EP | 1 734 927 A1 | 12/2006 |
| EP | 1 758 547 A1 | 3/2007 |
| EP | 1 483 001 B1 | 11/2007 |
| EP | 1 584 324 B1 | 11/2007 |
| EP | 1 889 609 A2 | 2/2008 |
| EP | 1 902 706 A1 | 3/2008 |
| EP | 2 422 768 A2 | 2/2012 |
| EP | 2 494 959 A1 | 9/2012 |
| FR | 2 456 522 A1 | 12/1980 |
| FR | 2 591 331 A1 | 6/1987 |
| FR | 2 640 942 A2 | 6/1990 |
| FR | 2 736 824 A1 | 1/1997 |
| FR | 2 774 595 A1 | 8/1999 |
| FR | 2 789 371 A1 | 8/2000 |
| FR | 2 793 479 A1 | 11/2000 |
| FR | 2 814 959 A1 | 4/2002 |
| FR | 2 833 246 A1 | 6/2003 |
| FR | 2 840 903 A1 | 12/2003 |
| FR | 2 843 373 A1 | 2/2004 |
| FR | 2 845 672 A1 | 4/2004 |
| FR | 2 848 998 A1 | 6/2004 |
| FR | 2 860 976 | 4/2005 |
| FR | 2 915 891 A1 | 11/2008 |
| GB | 808 104 A | 1/1959 |
| GB | 808 105 A | 1/1959 |
| GB | 922 930 A | 4/1963 |
| GB | 933 486 A | 8/1963 |
| GB | 998 490 A | 7/1965 |
| GB | 1 026 831 A | 4/1966 |
| GB | 1 033 299 A | 6/1966 |
| GB | 1 081 949 A | 9/1967 |
| GB | 1 121 358 A | 7/1968 |
| GB | 1 162 684 A | 8/1969 |
| GB | 1 170 152 A | 11/1969 |
| GB | 1 201 918 A | 8/1970 |
| GB | 1 347 950 A | 2/1974 |
| GB | 1 351 761 A | 5/1974 |
| GB | 1 351 762 A | 5/1974 |
| GB | 1 353 381 A | 5/1974 |
| GB | 1 376 649 A | 12/1974 |
| GB | 1 397 285 A | 6/1975 |
| GB | 1 408 036 A | 10/1975 |
| GB | 1 457 671 A | 12/1976 |
| GB | 1 489 672 A | 10/1977 |
| GB | 2 004 746 A | 4/1979 |
| GB | 1 561 423 A | 2/1980 |
| GB | 2 114 580 A | 8/1983 |
| GB | 2 166 651 A | 5/1986 |
| GB | 2 153 686 B | 7/1987 |
| GB | 2 172 298 B | 11/1988 |
| GB | 2 206 099 A | 12/1988 |
| GB | 2 337 461 A | 11/1999 |
| GB | 2 367 809 A | 4/2002 |
| GB | 2 406 330 A | 3/2005 |
| GB | 2 406 791 B | 2/2008 |
| GB | 2 474 930 A | 5/2011 |
| IL | 49491 A | 9/1979 |
| IL | 152 486 A | 5/2003 |
| JP | 55-069682 A | 5/1980 |
| JP | 56-039815 A | 4/1981 |
| JP | 57-044429 A | 3/1982 |
| JP | 60-001113 A | 1/1985 |
| JP | 61-275395 A | 12/1986 |
| JP | 62-241701 A | 10/1987 |
| JP | 63-119420 A | 5/1988 |
| JP | 01-100111 A | 4/1989 |
| JP | 01-156906 A | 6/1989 |
| JP | 02-184614 A | 7/1990 |
| JP | 02-255890 A | 10/1990 |
| JP | 03-050289 A | 3/1991 |
| JP | 04-51958 A | 2/1992 |
| JP | 04-282311 A | 10/1992 |
| JP | 04-312521 A | 11/1992 |
| JP | 05-070340 A | 3/1993 |
| JP | 05-213734 A | 8/1993 |
| JP | 06-100414 A | 4/1994 |
| JP | 06-263630 A | 9/1994 |
| JP | 06-329532 A | 11/1994 |
| JP | 07-215835 A | 8/1995 |
| JP | 08-040899 A | 2/1996 |
| JP | 08-501529 A | 2/1996 |
| JP | 08-119831 A | 5/1996 |
| JP | 08-165218 A | 6/1996 |
| JP | 08-277209 A | 10/1996 |
| JP | 09-84855 A | 3/1997 |
| JP | 09-099553 A | 4/1997 |
| JP | 09-110636 A | 4/1997 |
| JP | 10-114619 A | 5/1998 |
| JP | 10-332456 A | 12/1998 |
| JP | 11-501045 A | 1/1999 |
| JP | 11-250543 A | 9/1999 |
| JP | 2000-017174 A | 1/2000 |
| JP | 2000-080017 A | 3/2000 |
| JP | 2000-128734 A | 5/2000 |
| JP | 2000-191429 A | 7/2000 |
| JP | 2000-239140 A | 9/2000 |
| JP | 2000-351726 A | 12/2000 |
| JP | 2000-354623 A | 12/2000 |
| JP | 2001-002526 A | 1/2001 |
| JP | 2001-019606 A | 1/2001 |
| JP | 2001-072963 A | 3/2001 |
| JP | 2002-012513 A | 1/2002 |
| JP | 2002-047136 A | 2/2002 |
| JP | 2002-524490 A | 8/2002 |
| JP | 2002-302419 A | 10/2002 |
| JP | 2003-012511 A | 1/2003 |
| JP | 2003-055146 A | 2/2003 |
| JP | 2004-047136 A | 2/2004 |
| JP | 2004-250435 A | 9/2004 |
| JP | 2004-348277 A | 12/2004 |
| JP | 2005-314323 A | 11/2005 |
| JP | 2005-350378 A | 12/2005 |
| JP | 2006-008574 A | 1/2006 |

(56) References Cited

FOREIGN PATENT DOCUMENTS

| | | |
|---|---|---|
| JP | 2006-036317 A | 2/2006 |
| JP | 2006-103799 A | 4/2006 |
| JP | 2006-525145 A | 11/2006 |
| JP | 2007-131539 A2 | 5/2007 |
| JP | 2007-155667 A | 6/2007 |
| JP | 2007-326996 A | 12/2007 |
| KR | 0143232 A | 7/1998 |
| KR | 2001-003063 A | 1/2001 |
| NZ | 520014 A | 5/2005 |
| NZ | 540166 A | 6/2007 |
| RU | 2277501 C2 | 6/2006 |
| UA | 66796 C2 | 7/2001 |
| WO | WO 82/001821 A1 | 6/1982 |
| WO | WO 86/05389 A1 | 9/1986 |
| WO | WO 88/01502 A1 | 3/1988 |
| WO | WO 88/01863 A1 | 3/1988 |
| WO | WO 88/08316 A1 | 11/1988 |
| WO | WO 89/06537 A1 | 7/1989 |
| WO | WO 90/05774 A1 | 5/1990 |
| WO | WO 91/11991 A1 | 8/1991 |
| WO | WO 92/00077 A1 | 1/1992 |
| WO | WO 92/005142 A1 | 4/1992 |
| WO | WO 92/05763 A1 | 4/1992 |
| WO | WO 92/11839 A1 | 7/1992 |
| WO | WO 92/13602 A1 | 8/1992 |
| WO | WO 93/025189 A1 | 12/1993 |
| WO | WO 94/006440 A1 | 3/1994 |
| WO | WO 96/03115 A1 | 2/1996 |
| WO | WO 96/19921 A1 | 7/1996 |
| WO | WO 96/24325 A1 | 8/1996 |
| WO | WO 96/26711 A1 | 9/1996 |
| WO | WO 96/27376 A1 | 9/1996 |
| WO | WO 96/39119 A1 | 12/1996 |
| WO | WO 97/03638 A1 | 2/1997 |
| WO | WO 97/39745 A1 | 10/1997 |
| WO | WO 98/17282 A2 | 4/1998 |
| WO | WO 98/18472 A1 | 5/1998 |
| WO | WO 98/19654 A1 | 5/1998 |
| WO | WO 98/21955 A1 | 5/1998 |
| WO | WO 98/23291 A1 | 6/1998 |
| WO | WO 98/31339 A1 | 7/1998 |
| WO | WO 98/36733 A2 | 8/1998 |
| WO | WO 98/52536 A1 | 11/1998 |
| WO | WO 99/08649 A2 | 2/1999 |
| WO | WO 99/20250 A1 | 4/1999 |
| WO | WO 99/37282 A2 | 7/1999 |
| WO | WO 99/53923 A1 | 10/1999 |
| WO | WO 2000/09082 A1 | 2/2000 |
| WO | WO 2000/15193 A1 | 3/2000 |
| WO | WO 2000/23051 A1 | 4/2000 |
| WO | WO 2000/33825 A2 | 6/2000 |
| WO | WO 2000/38731 A1 | 7/2000 |
| WO | WO 2000/61076 A1 | 10/2000 |
| WO | WO 2000/62776 A1 | 10/2000 |
| WO | WO 2000/72805 A1 | 12/2000 |
| WO | WO 2000/76461 A2 | 12/2000 |
| WO | WO 2001/01949 A1 | 1/2001 |
| WO | WO 2001/05366 A1 | 1/2001 |
| WO | WO 2001/08681 A1 | 2/2001 |
| WO | WO 2001/10961 A1 | 2/2001 |
| WO | WO 2001/53198 A1 | 7/2001 |
| WO | WO 2001/54212 A1 | 7/2001 |
| WO | WO 2001/54679 A2 | 8/2001 |
| WO | WO 2001/62209 A2 | 8/2001 |
| WO | WO 2001/70242 A2 | 9/2001 |
| WO | WO 2001/76579 A1 | 10/2001 |
| WO | WO 2001/82880 A3 | 11/2001 |
| WO | WO 2001/82890 A1 | 11/2001 |
| WO | WO 2001/85102 A2 | 11/2001 |
| WO | WO 2001/85128 A2 | 11/2001 |
| WO | WO 2001/95728 A1 | 12/2001 |
| WO | WO 2002/00820 A1 | 1/2002 |
| WO | WO 2002/07685 A2 | 1/2002 |
| WO | WO 2002/15860 A1 | 2/2002 |
| WO | WO 2002/15873 A2 | 2/2002 |
| WO | WO 2002/24161 A1 | 3/2002 |
| WO | WO 2002/28435 A1 | 4/2002 |
| WO | WO 2002/41847 A1 | 5/2002 |
| WO | WO 2002/43490 A1 | 6/2002 |
| WO | WO 2002/062324 A2 | 8/2002 |
| WO | WO 2002/078667 A1 | 10/2002 |
| WO | WO 2002/087519 A1 | 11/2002 |
| WO | WO 2003/000223 A1 | 1/2003 |
| WO | WO 2003/002082 A1 | 1/2003 |
| WO | WO 2003/005985 A1 | 1/2003 |
| WO | WO 2003/013984 A1 | 2/2003 |
| WO | WO 2003/015699 A2 | 2/2003 |
| WO | WO 2003/051294 A2 | 6/2003 |
| WO | WO 2003/053292 A1 | 7/2003 |
| WO | WO 2003/055445 A2 | 7/2003 |
| WO | WO 2003/055454 A1 | 7/2003 |
| WO | WO 2003/070301 A1 | 8/2003 |
| WO | WO 2003/071995 A1 | 9/2003 |
| WO | WO 2003/075851 A2 | 9/2003 |
| WO | WO 2003/092641 A1 | 11/2003 |
| WO | WO 2003/094873 A1 | 11/2003 |
| WO | WO 2003/097002 A1 | 11/2003 |
| WO | WO 2004/017962 A2 | 3/2004 |
| WO | WO 2004/037197 A2 | 5/2004 |
| WO | WO 2004/037225 A2 | 5/2004 |
| WO | WO 2004/003284 A1 | 8/2004 |
| WO | WO 2004/064769 A2 | 8/2004 |
| WO | WO 2004/064833 A1 | 8/2004 |
| WO | WO 2004/071479 A1 | 8/2004 |
| WO | WO 2004/078158 A2 | 9/2004 |
| WO | WO 2004/078896 A1 | 9/2004 |
| WO | WO 2004/093895 A1 | 11/2004 |
| WO | WO 2004/112780 A1 | 12/2004 |
| WO | WO 2005/009416 A1 | 2/2005 |
| WO | WO 2005/011567 A2 | 2/2005 |
| WO | WO 2005/018530 A2 | 3/2005 |
| WO | WO 2005/032522 A1 | 4/2005 |
| WO | WO 2005/044219 A1 | 5/2005 |
| WO | WO 2005/063224 A1 | 7/2005 |
| WO | WO 2005/065652 A1 | 7/2005 |
| WO | WO 2005/076697 A2 | 8/2005 |
| WO | WO 2005/097068 A1 | 10/2005 |
| WO | WO 2005/102282 A1 | 11/2005 |
| WO | WO 2005/102539 A1 | 11/2005 |
| WO | WO 2005/117813 A1 | 12/2005 |
| WO | WO 2006/003481 A2 | 1/2006 |
| WO | WO 2006/010589 A2 | 2/2006 |
| WO | WO 2006/011046 A1 | 2/2006 |
| WO | WO 2006/020682 A1 | 2/2006 |
| WO | WO 2006/028339 A1 | 3/2006 |
| WO | WO 2006/031271 A2 | 3/2006 |
| WO | WO 2006/045170 A2 | 5/2006 |
| WO | WO 2006/079632 A1 | 8/2006 |
| WO | WO 2006/081327 A2 | 8/2006 |
| WO | WO 2006/091229 A2 | 8/2006 |
| WO | WO 2006/100485 A1 | 9/2006 |
| WO | WO 2006/1 21 61 | 11/2006 |
| WO | WO 2006/120682 A2 | 11/2006 |
| WO | WO 2006/122158 A2 | 11/2006 |
| WO | WO 2006/129161 A2 | 12/2006 |
| WO | WO 2006/131784 A1 | 12/2006 |
| WO | WO 2007/007208 A2 | 1/2007 |
| WO | WO 2007/010494 A1 | 1/2007 |
| WO | WO 2007/012977 A2 | 2/2007 |
| WO | WO 2007/023396 A2 | 3/2007 |
| WO | WO 2007/031621 A2 | 3/2007 |
| WO | WO 2007/039825 A2 | 4/2007 |
| WO | WO 2007/050543 A2 | 5/2007 |
| WO | WO 2007/054818 A2 | 5/2007 |
| WO | WO 2007/072216 A2 | 6/2007 |
| WO | WO 2007/082698 A1 | 7/2007 |
| WO | WO 2007/085902 A2 | 8/2007 |
| WO | WO 2007/099396 A2 | 9/2007 |
| WO | WO 2007/111962 A2 | 10/2007 |
| WO | WO 2008/008397 A2 | 1/2008 |
| WO | WO 2008/010963 A2 | 1/2008 |
| WO | WO 2008/038147 A2 | 4/2008 |
| WO | WO 2008/041045 A1 | 4/2008 |
| WO | WO 2008/075207 A2 | 6/2008 |

(56) References Cited

FOREIGN PATENT DOCUMENTS

| | | |
|---|---|---|
| WO | WO 2008/087148 A2 | 7/2008 |
| WO | WO 2008/104734 A1 | 9/2008 |
| WO | WO 2008/110872 A2 | 9/2008 |
| WO | WO 2008/152444 A2 | 12/2008 |
| WO | WO 2009/007785 A2 | 1/2009 |
| WO | WO 2009/069006 A2 | 6/2009 |
| WO | WO 2009/072007 A2 | 6/2009 |
| WO | WO 2009/087578 A2 | 7/2009 |
| WO | WO 2009/090495 A2 | 7/2009 |
| WO | WO 2009/090558 A2 | 7/2009 |
| WO | WO 2009/098595 A2 | 8/2009 |
| WO | WO 2011/006026 A1 | 1/2011 |
| WO | WO 2011/013008 A2 | 2/2011 |
| WO | WO 2011/013009 A2 | 2/2011 |
| WO | WO 2011/026094 A2 | 3/2011 |
| WO | WO 2011/039637 A2 | 4/2011 |
| WO | WO 2011/039638 A2 | 4/2011 |
| WO | WO 2011/064631 A1 | 6/2011 |
| WO | WO 2011/106026 A1 | 9/2011 |
| WO | WO 2011/138678 A2 | 11/2011 |
| WO | WO 2013/136192 A2 | 9/2013 |
| WO | WO 2014/134394 A1 | 9/2014 |
| WO | WO 2014/134427 A1 | 9/2014 |
| WO | WO 2014/151347 A1 | 9/2014 |
| WO | WO 2014/201541 A1 | 12/2014 |
| WO | WO 2015/075640 A1 | 5/2015 |
| WO | WO 2015/114320 A1 | 8/2015 |
| WO | WO 2015/153864 A2 | 10/2015 |
| WO | WO 2017/029647 A1 | 2/2017 |
| WO | WO 2017/030555 A1 | 2/2017 |
| WO | WO 2017/089809 A1 | 6/2017 |
| WO | WO 2019/082090 A1 | 5/2019 |

OTHER PUBLICATIONS

"Suppositories?" CareCure Community, SCI Forum [online]. http://sci.rutgers.edu/forum/showthread.php?4176-Suppositories. Published: Apr. 16, 2002, 3 pages.

1058. Benzalkonium Chloride; 2350. Citric Acid; 6143. Methyl Salicylate. The Merck Index: An Encyclopedia of Chemicals, Drugs, and Biologicals. 13th Edition, 2001, pp. 181, 405-406, 1090-1091, 1556.

242. Allantoin, The Merck Index: An Encyclopedia of Chemicals, Drugs, and Biologicals. 10th edition, Merck & Co., Inc., 1983, p. 39.

Abdullah, G.Z. et al. (Jan. 2013) "Carbopol 934, 940 and Ultrez 10 as viscosity modifiers of palm olein esters based nano-scaled emulsion containing ibuprofen" *Pak J Pharm Sci*, 26(1):75-83.

Abrams et al., "Ciclopirox gel treatment of scalp seborrheic dermatitis," in: Shuster, S. (ed.) Hydroxy-Piridones as Antifungal Agents with Special Emphasis on Onychomycosis. Springer, Berlin, Heidelberg; 1999, Chapter 8, pp. 45-50.

Adachi, "Storage and Oxidative Stability of O/W/ Nano-emulsions," Foods Food Ingredients J. Jpn., 2004, 209(11), 1 page (Abstract).

Adisen et al., "Topical tetracycline in the treatment of acne vulgaris," J Drugs Dermatol., Oct. 2008, 7(10):953-955.

Alcohol SDA 40B, 200 Proof. Material Safety Data Sheets [online]. Retrieved from the Internet: http://www.pharmco-prod.com/pages/MSDS/SDA.sub.--40B.sub.--200.pdf, on Dec. 9, 2008. MSDS 044, Revision 2.1, Revision Date Dec. 2005, 2 pages.

Alcohol, Wikipedia, the free encyclopedia [online]. Last modified on Apr. 23, 2014. Retrieved on May 17, 2014, http://en.wikipedia.org/wiki/Alcohol, 17 pages.

Aldara™ (imiquimod) Cream. Highlights of Prescribing Information, Graceway Pharmaceuticals, LLC, Mar. 2007, 29 pages.

Allantoin, Römpp Online, retrieved on Sep. 23, 2015, https://roempp.thieme.de/roempp4.0/do/data/RD-O 1-01552, 5 pages.

Al-Mughrabi et al., "Effectiveness of Essential Oils and Their Combinations with Aluminum Starch Octenylsuccinate on Potato Storage Pathogens," TEOP, 2013, 16(1):23-31.

Ambrose et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, Sep. 1991, 35(9):1799-1803.

Aminobenzoic Acid, Knovel, 2006, retrieved on Apr. 18, 2012, http://www.knovel.com/web/portal/knovel_content?p_p_id=EXT_KNOVEL_CONTENT . . . , 2 pages.

Anton et al., "Water-in-oil nano-emulsion formation by the phase inversion temperature method: a novel and general concept, a new template for nanoencapsulation," Proceedings of the 33rd Annual Meeting and Exposition of the Controlled Release Society, Jul. 2006, Vienna, Austria, 2 pages.

Arct et al., "Common cosmetic hydrophilic ingredients as penetration modifiers of flavonoids," International Journal of Cosmetic Science, Dec. 2002, 24(6):357-366 (Abstract Only).

Arisan, Kozmetic ve Kisisel Bakim Urunleri Grubu, retrieved on Dec. 10, 2008, http://www.arisankimya.com/kozmetik.htm, 8 pages.

Arquad HTL8-MS, AkzoNobel Functional Applications, retrieved on Mar. 18, 2013, Retrieved from the Internet: <URL: http://sc.akzonobel.com/en/fa/Pages/product-detail.aspx?prodID=8764>, 1 page.

Aslam et al. (2015) "Emerging drugs for the treatment of acne" *Expert Opin Emerging Drugs,* 20:91-101.

Atopic Dermatitis/Eczema, ibabydoc.com, Copyright 2000, retrieved on Jan. 30, 2010, http://www.ibabydoc.com/online/diseaseeczema.asp 6 pages.

Ausburger and Shangraw, "Bubble size analysis of high consistency aerosol foams and its relationship to foam rheology; Effects fo Container Emptying, Propellent Type, and Time," J. Pharma Sci, Apr. 1968, 57(4):624-631.

Austria, et al., "Stability of vitamin C derivatives in solution and topical formulations", Journal of Pharmaceutical and Biomedical Analysis, 1997, 15:795-801.

Barry and Badal, "Stability of minocycline, doxycycline, and tetracycline stored in agar plates and microdilution trays," Current Microbiology, 1978, 1:33-36.

Barry and Woodford, "Comparative bio-availability and activity of proprietary topical corticosteroid preparations: vasoconstrictor assays on thirty-one ointments," British J. Dermatology, 1975, 93:563-571.

Baskaran et al., "Poloxamer-188 improves capillary blood flow and tissue viability in a cutaneous burn wound," J. Surg. Res., 2001, 101(1):56-61.

Beauty Banter, "Interesting list of comedogenic ingredients!!!!!!!!!!!" QVC blog, Interesting list of comedogenic ingredients, 2014, 1-14.

Bell-Syer et al., "A systematic review of oral treatments for fungal infections of the skin of the feet," J. Dermatology. Treat., 2001, 12:69-74.

Ben-Et and Tatarsky "Application of NMR for the Determination of HLB Values of Nonionic Surfactants," Journal of the American Oil Chemists Society, Mar. 20, 1972, 49:499-500.

Bernstein and Harrison, "Effects of the Immunomodulating Agent R837 on Acute and Latent Herpes Simplex Virus Type 2 Infections," Antimicrobial Agents and Chemotherapy, Sep. 1989, 33(9):1511-1515.

Beuchat (Feb. 1983) "Influence of Water Activity on Growth, Metabolic Activities and Survival of Yeasts and Molds" *J Food Prot,* 46(2):135-141.

Blaney and Cook, "Topical use of tetracycline in the treatment of acne," Arch Dermatol, Jul. 1976, 112:971-973.

Blute et al., "Phase behaviour of alkyl glycerol ether surfactants", Physikalische Chemie/Physical Chemistry Tenside Surf. Det., 1998, 35(3):207-212.

Boehm et al., "Synthesis of high specific activity [.sup.3 H]-9-cis-retinoic acid and its application for identifying retinoids with unusual binding properties," J. Med. Chem., 1994, 37:408-414.

Brenes, et al., "Stability of Copigmented Anthocyanins and Ascorbic Acid in a Grape Juice Model System", J. Agric Food Chem, 2005, 53(1):49-56 (Abstract Only).

Brisaert, M. et al. (1996) "Investigation on the chemical stability of erythromycin in solutions using an optimization system" *Pharm World Sci,* 18(5):182-186.

(56) References Cited

OTHER PUBLICATIONS

Bronopol, 2-BROMO-2-NURO-1,3-Propanediol, Chemical land, Jul. 17, 2006, retrieved on Jun. 4, 2011, http://chemicalland21.com/specialtychem/perchem/Bronopol.html, 4 pages.
Brown et al., " Structural dependence of flavonoid interactions with Cu2+ ions: implications for their antioxidant properties," Biochem. J., 1998, 330:1173-1178.
Buck and Guth, "Treatment of Vaginal Intraepithelial Neoplasia (Primarily Low Grade) with Imiquimod 5% Cream", Journal of Lower Genital Tract Disease, 2003, 7(3):290-293.
Bucks et al., "Bioavailability of Topically Administered Steroids: A "Mass Balance" Technique," J. Investigative Dermatology, 1988, 91(1):29-33.
Bunker and Dowd, "Alterations in Scalp Blood Flow after the Epicutaneous Application of 3% Minoxidil and 0.1% Hexyl Nicotinate in Alopecia," British Society for Investigative Dermatology, Sep. 1986, 117(5):668-669.
Burn Patients Need Vitamin D Supplements, NUTRAingredients.com, Jan. 23, 2004, retrieved on May 5, 2010, http://www.nutraingredients.com/Research/Burn-patients-need-vitamin-D-supplements, 1page.
Burton and Marshall, "Hypertrichosis due to minoxidil," British J. Dermatology, 1979, 101:593-595.
C12-15 Alkyl Benzoate, Paula's Choice Skincare, retrieved on Oct. 24, 2010, http://ww.cosmeticscop.com/cosmetic-ingredient-dictionary/definition/259/c12-15-alkyl-benzoate.aspx, 1 page.
Campos and Silva, "Ascorbic Acid and Its Derivatives in Cosmetic Formulations", Cosmetics and Toiletries, 2000, 115(6):59-62 (Abstract Only.
Can Tuberous Sclerosis Be Prevented?, Sharecare, 2002, retrieved on Aug. 29, 2013, <URL: http://www.sharecare.com/health/autosomal-dominant-genetic-disorders/can-tuberous-sclerosis-be-prevented;jsessionid=8505791360520A907DE75930E061E60E6>, 2 pages.
Canavan et al. (2016) "Optimizing Non-Antibiotic Treatments for Patients with Acne: A Review" *Dermatol Ther,* 6:555-578.
Carapeti et al., "Topical diltiazem and bethanechol decrease anal sphincter pressure and heal anal fissures without side effects," Dis Colon Rectum, 2000, 43(10):1359-1362.
Carbowax 1000MSDS, Material Safety Data Sheet for Polyethylene glycol 1000 MSDS, last updated Nov. 6, 2008, retrieved on Dec. 13, 2008, http://www.sciencelab.com/xMSDS-Polyethylene.sub.-glycol.sub.-1000-9926-622, 6 pages.
Carelli et al., "Effect of Vehicles on Yohimbine Permeation Across Excised Hairless Mouse Skin", Pharm Acta Helv, Aug. 1978, 73(3):127-134 (Abstract Only).
Causes of Psoriasis, retrieved on Sep. 9, 2010, http://www.quickcare.org/skin/causes-of0psoriasis.html, 3 pages.
Cetearyl Alcohol, Natural Wellbeing, Copyright 2001-2012, retrieved on Apr. 10, 2014, http://www.naturalwellbeing.com/learning-center/Cetearyl_Alcohol, 3 pages.
Chebil et al., "Solubility of Flavonoids in Organic Solvents," J. Chem. Eng. Data, 2007, 52(5):1552-1556 (Abstract Only).
Chemical Characteristics, The Olive Oil Source, © 1998-2015, retrieved on Jun. 12, 2015, http://www.oliveoilsource.com/page/chemical-characteristics, 10 pages.
Cheshire and Freeman, "Disorders of Sweating," Semin Neurol, 2003, 23(4):399-406.
Chevrant-Breton et al., "Etude du Traitement Capillaire <<Bioscalin>> dans les Alopecies Diffuses de la Femme", Gazette Medicale, 1986, 93(17):75-79 (English Abstract).
Chiang et al., "Bioavailability Assessment of Topical Delivery Systems: In Vitro Delivery of Minoxidil from Prototypical Semi-Solid Formulations", Int. J. Pharm, 1989, 49(2):109-114 (Abstract Only).
Chinnian et al., "Photostability Profiles of Minoxidil Solutions", PDA J. Pharm Sci Technol., Mar.-Apr. 1996, 50(2):94-98 (English Abstract).
Chollet et al., "Development of a Topically Active Imiquimod Formulation", Pharmaceutical Development and Technology, 1999, 4(1):35-43.

Chollet et al., "The Effect of Temperatures on the Solubility of Imiquimod in Isostearic Acid", Abstract 3031, Pharmaceutical Research, Nov. 1997, 14(11 Supplemental):S475.
Chrysos et al., "Effect of nifedipine on rectoanal motility," Dis Colon Rectum, Feb. 1996, 39(2):212-216.
Clobetasol Propionate Cream and Ointment, Apr. 2006, retrieved Jul. 3, 2014, http://dailymed.nlm.nih.gov/dailymed/archives/fdaDrugInfo.cfm?archiveid=994, 7 pages.
Cloez-Tayarani et al., "Differential effect of serotonin on cytokine production in lipopolysaccharide-stimulated human peripheral blood mononuclear cells: involvement of 5-hydroxytryptamine2A receptors," Int. Immunol., 2003, 15:233-240.
Coal Tars and Coal-Tar Pitches, *Report on Carcinogens, Twelfth Edition,* 2011, 3 pages.
Coatzee et al., "Acceptability and feasibility of Micralax® applicators and of methyl cellulose gel placebo for large-scale clinical trials of vaginal microbicides," AIDS, 2001, 15:1837-1842.
Coconut Oil, Wikipedia, the free encyclopedia, retrieved on Jul. 3, 2015, https://en.wikipedia.org/wiki/Coconut_oil, 8 pages.
Codex Standard for Olive Oils and Olive Pomace Oils Codex Stan 33/1981, Adopted in 1981, recently amended 2013, 8 pages.
Cole and Gazewood, "Diagnosis and Treatment of Impetigo," American Family Physical Website, 2007, http://www.aafp.org/afp, 6 pages.
Colloidal Silica, W.R. Grace & Co. Enriching Lives, Everywhere™, 2011, retrieved on Jun. 4, 2011, http://www.grace.com/engineeredmaterials/materialsciences/colloidalsilica/default.aspx, 4 pages.
Communication of a Notice of Opposition in European Application No. 03772600.7, dated Jan. 13, 2015, 36 pages.
Cook and Mortenson, "Nifedipine for treatment of anal fissures," Dis Colon Rectum, 2000, 43(3):430-431.
Craig, D.Q.M. et al. (Jul. 1994) "An investigation into the structure and properties of Carbopol 934 gels using dielectric spectroscopy and oscillatory rheometry" *J Controlled Rel,* 30(3):213-223 (Abstract).
Cremophor A Grades, BASF The Chemical Company, Jan. 2008, 6 pages.
Croda Crop Care, Arlacel 165, 2011, retrieved on Aug. 3, 2015, http://www.crodapersonalcare.com/home.aspx?view=dtl&d=content&s=157&r=401&p=2578&productName=&inciname=&application=&subapplication=&productfunction=&consumerbenefit=&prodID=1926, 2 pages.
Croda Product Care Europe, Cetomacrogol 1000, 2011, retrieved on Aug. 3, 2015, http://www.crodapersonalcare.com/home.aspx?view=dtl&d=content&s=157&r=273&p=1859&productName=&inciname=&chemicaltype=&application=&subapplication=&productfunction=&consumerbenefit=&prodID=27, 1 page.
Crohn'S Disease, Merck Manual Home Edition, retrieved on Jan. 16, 2013, <http://www.merckmanuals.com/home/digestive_disorders/inflammatory_bowel_diseases_ibd/crohn_disease.html?qt=crohn's disease&alt=sh>, 3 pages.
Cunha, "Minocycline versus Doxycycline in the treatment of Lyme Neuroborreliosis," Clin. Infect. Diseases, 2000, 30: 237-238.
Dacarbazine, Chemical Book, 2010, retrieved on Oct. 18, 2013, <URL: http://www.chemicalbook.com/ChemicalProductProperty_EN_CB7710656.htm>, 2 pages.
Dalby et al., "Determination of Drug Solubility in Aerosol Propellants," Pharmaceutical Research, 1991, 8(9):1206-1209.
Dawber and Rundegren, "Hypertrichosis in Females Applying Minoxidil Topical Solution and in Normal Controls", JEADV, 2003, 17:271-275.
Denatonium Benzoate, retrieved Dec. 9, 2008, http://www.newdruginfo.com/pharmaceopeia/usp28/v28230/usp28nf23s0_m-22790.htm, 2 pages.
Dentinger, et al., "Stability of Nifedipine in an Extemporaneously Compounded Oral Solution", American Journal of Health-System Pharmacy, 2003, 60(10):1019-1022 (English Abstract).
Derivative, Merriam Webster Online Dictionary, retrieved on Jul. 5, 2008, http://www.merriam-webstercom/cgi-bin/dictionary?book=dictionary&va=derivative, 1 page.
Devos and Miller, "Antisense Oligonucleotides: Treating neurodegeneration at the Level of RNA," Neurotherapeutics, 2013, 10:486-497.

(56) References Cited

OTHER PUBLICATIONS

Diethyltoluamide, Wikipedia, the free encyclopedia, retrieved on Sep. 11, 2015, https://de.wikipedia.org/wiki/Diethyltoluamid, 12 pages.
Dimethylphthalate, Wikipedia, the free encyclopedia, retrieved on Sep. 11, 2015, http://de.wikipedia.org/wiki/Dimethylphthalat, 8 pages.
Disorder, American Heritage Dictionary of the English Language, 2007, retrieved on Oct. 9, 2010, http://www.credoreference.com/entry/hmdictenglang/disorder, 1 page.
Draelos, "Antiperspirants and the Hyperhidrosis Patients," Dermatologic Therapy, 2001, 14:220-224.
Drug Index—Dacarbazine, BC Cancer Agency, Jun. 2004, retrieved on Oct. 18, 2013, <URL:http://www.bccancer.bc.ca/HPI/DrugDatabase/DrugIndexPro/Dacarbazine.htm>, 6 pages.
Drugfuture, Chemical Index Database, "Sorbitan Esters" Monograph [online]. Retrieved from: http://www.drugfuture.com/chemdata/sorbitan-esters.html on Jul. 1, 2016, 2 pages.
Durian et al., "Scaling behavior in shaving cream," The American Physical Society, Dec. 1991, 44(12):R7902-7905.
Durmortier et al., "A review of poloxamer 407 pharmaceutical and pharmacological characteristics," Pharmaceutical Res., Dec. 2006, 23(12):2709-2728.
E7023 Ethanol 200 Proof (Absolute), Sigma-Aldrich Co., © 2008, retrieved on Dec. 9, 2008, http://www.sigmaaldrich.com/catalog/ProductDetail.do?N4=E7023SIAL&N5=SEAR-CH.sub.--CONCAT.sub.--PNOBRAND.sub.--KEY&F=SPEC, 2 pages.
Ebadi et al., "Healing effect of topical nifedipine on skin wounds of diabetic rats," DARU, 2003, 11(1):19-22.
Edens et al., "Storage Stability and Safety of Active Vitamin C in a New Dual-Chamber Dispenser", Journal of Applied Cosmetology, 1999, 17(4):136-143 (English Abstract).
Edirisinghe et al., "Effect of fatty acids on endothelium-dependent relaxation in the rabbit aorta", Clin Sci, Aug. 2006, 111(2): 145-51.
Edwards, "Imiquimod in Clinical Practice," J. Am Acad Dermatol., Jul. 2000 43(1, Pt 2):S12-S17 (English Abstract).
Effendy and Maibach "Surfactants and Experimental Irritant Contact Dermatitis." Contact Dermatol., 1995, 33:217-225.
Elias and Ghadially, "The aged epidermal permeability barrier," Clinical Geriatric Medicine, Feb. 2002, 103-120.
Ellis et al., "The Treatment of Psoriasis with Liquor Carbonis Detergens," J. Invest Dermatology, 1948, 10:455-459.
Emulsifiers With HLB Values, The Herbarie, retrieved on Aug. 5, 2009, http://www.theherbarie.com/files/resources-center/formulating/Emulsifiers-.sub.--HLB.sub.--Values.pdf, 3 pages.
Esposito et al., "Nanosystems for Skin Hydration: A Comparative Study," International Journal of Cosmetic Science, 2007, 29: 39-47.
Established ("Approved") Excipients, Encyclopedia of Pharmaceutical Technology, Second Edition, © 2002, vol. 3, 2146-2147.
Ethylene Oxide Derivatives: An Essence of Every Industry, retrieved on Jul. 12, 2011, http://www.emulsifiers.in/ethylene_oxide_derivatives2.htm, 3 pages.
European Patent Application No. 03772600.7 (Patent No. 1556009): Communication of a Notice of Opposition, dated Sep. 23, 2015, 42 pages.
European Patent Application No. 03772600.7 (Patent No. 1556009): Communication of a Notice of Opposition, dated Sep. 24, 2015, 30 pages.
European Patent Application No. 03772600.7 (Patent No. 1556009): Reply of the Patent Proprietor to the Notices of Opposition, dated May 9, 2016, 134 pages.
European Patent Application No. 03772600.7 (Patent No. 1556009): Summons to Attend Oral Proceedings, dated Jun. 30, 2016, 19 pages.
European Patent Application No. 03772600.7 (Patent No. 1556009): Interlocutory Decision in Opposition Proceedings, dated Feb. 3, 2017, 54 pages.
European Patent Application No. 03772600.7 (Patent No. 1556009): Minutes of Oral Proceedings, dated Feb. 3, 2017, 6 pages.
Excessive Sweating, Merck Manual Home Edition, Oct. 2007, retrieved on Apr. 14, 2011, www.merckmanuals.com/home/print/sec18/ch206/ch206c.html, 2 pages.
Fantin et al., "Critical influence of resistance to streptogramin B-type antibiotics on activity of RP 59500 (Quinupristin-dalfopristin) in experimental endocarditis due to *Staphylococcus aureus*," Antimicrob Agents and Chemothery, Feb. 1995, 39:400-405.
Farahmand et al., "Formulation and Evaluation of a Vitamin C Multiple Emulsion", Pharmaceutical Development and Technology, May 2006, 11(2):255-261 (English Abstract).
Flick, Cosmetic and Toiletry Formulations, 2nd Edition, Copyright 1996, vol. 5, 251-309.
Floyd, "Silicone Surfactants: Applicants in the Personal Care Industry," Silicone Surfactants, 1999, Chapter 7, 181-207.
Fluhr et al., "Glycerol accelerates recovery of barrier function in vivo," Acta Derm. Venereol, 1999, 79:418-421.
Foamix Pharmaceuticals Ltd. (May 1, 2017) "Foamix Pharmaceuticals Announces Plans for Additional Phase 3 Trial for FMX101 in Moderate to Severe Acne," Press Release [online]. Retrieved from: http://www.foamix.co.il/news.asp?nodeID=564&itemID=204, on Jun. 12, 2017, 5 pages.
Foamix Pharmaceuticals, Statement: Use of Luviquat FC 370, Approved by Yohan Hazot, May 3, 2016, 3 pages.
Fontana, "Water Activity: Why It is Important for Food Safety," International Conference on Food Safety, Nov. 16-18, 1998, 177-185.
Fontana (Apr. 1999) "Pharmaceutical Applications for Water Activity" *Pharmaceutical Online* [online]. Retrieved from https://www.pharmaceuticalonline.com/doc/pharmaceutical-applications-for-water-activit- . . . , on Jan. 17, 2018 (4 pages).
Frankel, A.J. et al. (2010) "Coal Tar 2% Foam in Combination with a Superpotent Corticosteroid Foam for Plaque Psoriasis. Case Report and Clinical Implications" *J Clin Aesthet Dermatol*, 3(10):42-45.
Fully-Refined Paraffin Wax (FRP Wax), Industrial Raw Materials LLC, Feb. 21, 2008, retrieved on Aug. 22, 2013, <http://irmwax.com/Wax/Paraffin/fully_refined.asp> 1 page.
Gallarate et al., "On the Stability of Ascorbic Acid in Emulsified Systems for Topical and Cosmetic Use", International Journal of Pharmaceutics, 1999, 188:233-241.
Galligan et al., "Adhesive Polyurethane Liners for Anterior Restorations," J. Dent. Res., Jul.-Aug. 1968, 629-632.
Garti et al. "Sucrose Esters microemulsions," J. Molec. Liquids, 1999, 80:253-296.
Gas Gangrene, Merck Manual Home Edition, 2008, retrieved on Jan. 16, 2013, <http://www.merckmanuals.com/home/infections/bacterial_infections/gas_gangrene.html?qt=gasgangrene&alt=sh>1 page.
Gelbard et al. "Primary Pediatric Hyperhidrosis: A Review of Current Treatment Options," Pediatric Dermatology, 2008, 25(6):591-598.
Gels, UNC: The Pharmaceutics and Compounding Laboratory, retrieved on Aug. 25, 2014, http://pharmlabs.unc.edu/labs/gels/agents/htm, 4 pages.
Ghica, M.V. et al. (2011) "Design and optimization of some collagen-minocycline based hydrogels potentially applicable for the treatment of cutaneous wound infections" *Pharmazie*, 66:853-861.
Gill et al., "Adverse Drug Reactions in a Paediatric Intensive Care Unit," Acta Paediatric, 1995, 84:438-441.
Gladkikh, "Ascorbic Acid and Methods of Increasing its Stability in Drugs", Translated from Khimiko-Farmatsevticheskii Zhurnal, 1970, 4(12):37-42.
Glaser and Ballard, "Hyperhidrosis: A Comprehensive and Practical Approach to Patient Management," Expert Rev. Dermatol., Oct. 2006, 1(6):773-775.
Google Search Strategy for Minocycline Solubility, retrieved on Aug. 15, 2013, <http://www.googl.com/search?rls=com.microsoft%3Aen-us%3AIE-SearchBox&q-melocycline+solubility>, 1 page.
Graves et al., "Structure of Concentrated Nanoemulsions," The Journal of Chemical Physics, Apr. 1, 2005, 122:134703, 6 pages.
Griffin, "Calculation of HLB Values of Non-Ionic Surfactants," Journal of the Society of Cosmetic Chemists, May 14, 1954, 249-256.

(56) References Cited

OTHER PUBLICATIONS

Groveman et al., "Lack of Efficacy of Polysorbate 60 in the Treatment of Male Pattern Baldness", Arch Intern Med, 1985, 145:1454-1458.
Gschnait et al., "Topical Indomethacin Protects from UVB and UVA Irradiation," Arch. Dermatol. Res., 1984, 276:131-132.
Hakan et al., "The protective effect of fish oil enema in acetic acid and ethanol induced colitis," The Turkish Journal of Gastroenterology, 2000, 11(2):155-161.
Hall, "Diaper Area Hemangiomas: A Unique Set of Concerns," retrieved on Dec. 1, 2008, http://members.tripod.com/.about.Michelle.sub.--G/diaper.html, 8 pages.
Hallstar® GMS SE/AS, retrieved on Jun. 4, 2011, http://www.hallstar.com/pis.php?product=1H022, 1 page.
Hammer et al., "Anti-Microbial Activity of Essential Oils and other Plant extracts," J. Applied Microbiology, 1999, 86:985-990.
Hargreaves, "Chemical Formulation, An Overview of Surfactant-Based Preparations Used in Everyday Life", The Royal Society of Chemistry, 2003, 114-115.
Harrison et al., "Effects of cytokines and R-837, a cytokine inducer, on UV-irradiation augmented recurrent genital herpes in guinea pigs", Antiviral Res., 1991, 15(4):315-322.
Harrison et al., "Modification of Immunological Responses and Clinical Disease During Topical R-837 Treatment of Genital HSV-2 Infection," Antiviral Research, 1988, 10:209-224.
Harrison et al., "Pharmacokinetics and Safety of Imiquimod 5% Cream in the Treatment of Actinic Keratoses of the Face, Scalp, or Hands and Arms", Arch. Dermatol. Res., Jun. 2004, 296(1):6-11 (English Abstract).
Harrison et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, Sep. 1994, 38(9):2059-2064.
Harry, "Skin Penetration," The British Journal of Dermatology and Syphilis, 1941, 53:65-82.
Hashim et al., "Tinea versicolor and visceral leishmaniasis," Int J Dermatol., Apr. 1994; 33(4):258-259 (Abstract).
Haute.De, "Substance (INCI-Designation): Triethanolamine" [online]. Retrieved on Sep. 14, 2015, http://www.haut.de/service/inci/anzeige&id=16384&query=Triethanolamine&funktio . . . ; German with English translation, 3 pages.
Haw, "The HLB System: A Time Saving Guide to Surfactant Selection," Presentation to the Midwest Chapter of the Society of Cosmetic Chemists, Mar. 9, 2004, 39 pages.
Healy, "Gelled Emollient Systems for Controlled Fragrance Release and Enhanced Product Performance," Cosmetics and toiletries, 2002, 117(2): 47-54.
Heart Failure, The Merck Manual, 2008, retrieved Oct. 9, 2010, http://www.merck.com/mmhe/sec03/ch025/ch025a.html, 12 pages.
Helmenstine, "Surfactant Definition—Chemistry Glossary Definition of Surfactant," About.com Chemistry, retrieved on Mar. 5, 2012, http://chemistry.about.com/od/chemistryglossary/g/surfactant.htm, 1 page.
Hepburn, "Cutaneous leishmaniasis," Clin Exp Dermatol, Jul. 2000, 25(5):363-370 (Abstract).
HLB Systems, Pharmcal.tripod.com, retrieved on Sep. 17, 2010, http://pharmcal.tripod.com/ch17.htm, 3 pages.
HLB-Numbers, Sigma Aldrich, 2009, retrieved on Feb. 2, 2009, http://www.sigmaaldrich.com/materials-science/micro-and-nanoelectronics/l-ithography-nanopatterning/hlb-numbers.html, 3 pages.
How to Have a Healthy Libido in Mid-Life and Beyond, GreenWillowTree.com, Jan. 2001, retrieved on Jul. 28, 2012, http://www.greenwillowtree.com/Page.bok?file=libido.html, 5 pages.
Hubbe, Colloidal Silica, Mini-Encyclopedia of Papermaking Wet-End Chemistry: Additives and Ingredients, their Composition, Functions, Strategies for Use, Feb. 1, 2001, retrieved on Jun. 4, 2011, http://www4.ncsu.edu/~hubbe/CSIL.htm, 2 pages.
Human Immunodeficiency Virus Infection, Merck Manual Home Edition, 2008, retrieved on Jan. 16, 2013, <http://www.merckmanuals.com/home/infections/human_immunodeficiency_virus_hiv_infection/human_immunodeficiency_virus_infection.html?qt=human immunodeficiency virus infection&alt=sh >, 11 pages.
Hwang et al., "Isolation and identification of mosquito repellents in *Artemisia vulgaris*,"J. Chem. Ecol., 1985, 11: 1297-1306.
ICI Americas Inc., "Meaning of HLB Advantages and Limitations" Chapter 1 in *The HLB System. A Time-Saving Guide to Emulsifier Selection*. Wilmington, Delaware: 1980; pp. 1-4.
Ikuta et al., "Scanning Electron Microscopic Observation of Oil/Wax/Water/Surfactant System", Journal of SCCJ, 2004, 34(4):280-291 (English Abstract).
Indomethacin, Aug. 15, 2009, retrived on Jun. 3, 2011, http://it03.net/com/oxymatrine/down/1249534834.pdf, 3 pages.
Innocenzi et al., "An Open-Label Tolerability and Effacy Study of an Aluminum Sesquichlorhydrate Topical Foam in Axillary and Palmar Primary Hyperhidrosis," Dermatologic Therapy, 2008, 21:S27-S30.
Izquierdo et al. "Formation and Stability of Nano-Emulsions Prepared Using the Phase Inversion Temperature Method," Langmuir, 2002, 18(1):26-30 (Abstract).
Jan, "Troubled Times: Detergent Foam," retrieved on Feb. 9, 2012, http://zetatalk.com/health/theal17c.htm, 2 pages.
Joseph, "Understanding foams & foaming," University of Minnesota, May 1997, http://www.aem.umn.edu/people/faculty/joseph/archive/docs/understandingfoams.pdf, 8 pages.
Kalkan et al., "The Measurement of Sweat Intensity Using a New Technique," Tr. J. of Medical Sciences, 1998, 28:515-517.
Kanamoto et al., "Pharmacokinetics of two rectal dosage forms of ketoprofen in patients after anal surgery," J Pharmacobiodyn., Mar. 1988, 11(3):141-145.
Kang et al., "Enhancement of the Stability and Skin Penetration of Vitamin C by Polyphenol", Immune Netw., Dec. 2004, 4(4):250-254 (English Abstract).
Kanicky, J.R. and D.O. Shah (2002) "Effect of Degree, Type, and Position of Unsaturation on the $pK_a$ of Long-Chain Fatty Acids" *J Colloid and Interface Science,* 256:201-207.
Karasu et al., "Practice Guideline for the Treatment of Patients with Major Depressive Disorder," Second Edition, Apr. 2000, 78 pages.
Kathon™ CG, Rohm and Haas Personal Care, Jun. 2006, 9 pages.
Kaur et al., "Formulation Development of Self Nanoemulsifying Drug Delivery System (SNEDDS) of Celecoxib for Improvement of Oral Bioavailability," Pharmacophore, 2013, 4(4):120-133.
Kim, "Stability of Minoxidil in Aqueous Solution", Yakhak Hoechi, 1986, 30(5):228-231 (English Abstract).
Kinnunen and Hannuksela, "Skin reactions to hexylene glycol," Contact Dermatitis, Sep. 1989, 21(3):154-158.
Kircik, L.H. and S. Kumar (Aug. 2010) "Scalp Psoriasis" *J Drugs Dermatol,* 9(8 Suppl):s101-s137.
Kleber et al., "Practice Guideline for the Treatment of Patients with Substance Use Disorders," Aug. 2006, 276 pages.
Klucel Hydroxypropylcellulose; Chemical and Physical Properties, Hercules Limited, copyright 1986, retrieved on Aug. 25, 2014, http://legacy.library.ucsf.edu/tid/cnf81a99/pdf, 35 pages.
Knight et al., "Topical diltiazem ointment in the treatment of chronic anal fissure," Br. J. Surg., 2001, 88(4):553-556.
Koerber, "Humectants and Water Activity," Water Activity News, 2000, 8 pages.
Kolb, "Emulsifiers, emollients and solubilizers for personal care", pp. 1-9, accessed Jun. 20, 2018.
Kreuter, "Nanoparticles and microparticles for drug and vaccine delivery," J. Anat., 1996, 189:503-505.
Kucharekova et al., "Effect of a lipid-rich emollient containing ceramide 3 in experimentally induced skin barrier dysfunction," Contact Dermatitis, Jun. 2002, 46:331-338.
Kumar et al., "Application of Broad Spectrum Antiseptic Povidone Iodine as Powerful Action: A Review," Journal of Pharmaceutical Science and Technology, 2009, 1(2):48-58.
Kwak et al. "Study of Complete Transparent Nano-Emulsions which Contain Oils." IFSCC Conference, Seoul Korea, Sep. 2003, 3 pages.
Laboratory 6- Characteristics of Surfactants and Emulsions, retrieved on Jan. 29, 2010, http://web.archive.org/web/20000106225413/http://pharmacy.wilkes.edu/kibbeweb/lab7.html, 5 pages.

(56) References Cited

OTHER PUBLICATIONS

Lautenschlager, "A Closer Look on Natural Agents: Facts and Future Aspects," Kosmetic Konzept Kosmetische Praxis, 2006, 5:8-10.
Le Vine et al., "Components of the Goeckerman Regimen," Journal of Investigative Dermatology, 1979, 73:170-173.
Lebwohl and Ali, "Treatment of psoriasis. Part 1. Topical therapy and phototherapy," J. Am Acad Dermatol, Oct. 2001, 487-498.
Lebwohl et al., "A randomized, double-blind, placebo-controlled study of clobestasol propionate 0.05% foam in the treatment of nonscalp psoriasis," International Journal of Dermatology, 2002, 41(5): 269-274.
Lee et al., "Historical review of melanoma treatment and outcomes," Clinics in Dermatology, 2013, 31: 141-147.
Lee et al., "The Stabilization of L-Ascorbic Acid in Aqueous Solution and Water-in-Oil-in-Water Double Emulsion by Controlling pH and Electrolyte Concentration," J. Cosmet. Sci., Jan./Feb. 2004, 55:1-12.
Leive et al., "Tetracyclines of various hydrophobicities as a probe for permeability of *Escherichia coli* outer membrane," Antimicrobial Agents and Chemotherapy, 1984, 25:539-544.
Leunapon-F, Leuna-Tenside, Screenshot, retrieved on Sep. 18, 2015, http://www.leuna-tenside.de/2006_7_14_3143/2006_8_7 5750/2006_8_7 241/cas-68439-49-6, 1 page.
Leung and Robinson, "Bioadhesive Drug Delivery," American Chemical Society, 1991, Chapter 23, 350-366.
Li et al., "Solubility Behavior of Imiquimod in Alkanoic Acids", Pharmaceutical Research, Abstract 3029, Nov. 1997,14(11):S475, 2 pages.
Licking Vaginal Dryness Without a Prescription, retrieved on Dec. 14, 2008, http://www.estronaut.com/a/vag.sub.--dryness.htm, 3 pages.
Lin et al., "Ferulic acid stabilizes a solution of vitamins c and e and doubles its photoprotection of skin," J Invest Dermatol, 2005, 125:826-832.
Lippacher et al., "Liquid and Semisolid SLN Dispersions for Topical Application: Rheological Characterization," European Journal of Pharmaceutics and Biopharmaceutics, 2004, 58:561-567.
Livingstone and Hubel, "Segregation of form, color, movement, and depth: Anatomy, physiology, and perception," Science, May 1988, 240:740-749.
Lupke and Kemper, "The HET-CAM Test: An Alternative to the Draize Eye Test," FD Chem. Toxic., 1986, 24:495-196.
Lupo, "Antioxidants and Vitamins in Cosmetics", Clinics in Dermatology, 2001, 19:467-473.
Luviquat Polymer Grades, BASF The Chemical Company, May 2012, 32 pages.
Mailer, "Chemistry and quality of olive oil," NSW Dept. of Primary Industries, Aug. 2006, Primefact 227, 1-4.
Martindale: The Complete Drug Reference, 33rd Edition, Jun. 2002, Pharmaceutical Press, pp. 1073 and 1473.
Martindale: The Complete Drug Reference, Thirty-third edition, Bath Press, London, 2002, 1073 and 1473.
Martindale: The Extra Pharmacopoeia, Twenty-eighth edition, The Pharmaceutical Press, London, 1982, 862-864.
Material Safety Data Sheet, Luvitol EHO, Caelo, Nov. 28, 2013, 4 pages.
Material Safety Data Sheet, Butane, Gas Innovations, Sep. 7, 2007, 3 pages.
Material Safety Data Sheet, Carbon Dioxide, Airgas, Feb. 11, 2016, 11 pages.
Material Safety Data Sheet, Dimethyl Ether, Airgas, May 14, 2015, 12 pages.
Material Safety Data Sheet, Hydroxyethyl Cellulose, Sigma-Aldrich, Jan. 14, 2004, http://terpconnect.umd.edu/-choi/MSDS/Sigma-Aldrich/HYDROXYETHYL%20CELLULOSE, 5 pages.
Material Safety Data Sheet, Hydroxyethyl Cellulose, Sigma-Aldrich, Jan. 2004, 5 pages.
Material Safety Data Sheet, Liquor carbonis detergens, Caelo, Nov. 28, 2013, 5 pages.
Material Safety Data Sheet, Mineral Oil, Macron Fine Chemicals, Oct. 24, 2011, 6 pages.
Material Safety Data Sheet, N-Butane, Airgas, May 7, 2015, 13 pages.
Material Safety Data Sheet, Nitrous Oxide, Airgas, Feb. 11, 2016, 11 pages.
Material Safety Data Sheet, Propane, Airgas, Oct. 20, 2015, 12 pages.
Material Safety Data Sheet, Science Lab.com, Polyethylene Glycol 200, MSDS, Nov. 6, 2008, 6 pages.
Material Safety Data Sheet, USP, Progesterone, Apr. 26, 2006, 5 pages.
Mead, "Electrostatic Mechanisms Underlie Neomycin Block of the Cardiac Ryanodine Receptor Channel (RyR2)," Biophysical Journal, 2004, (87): 3814-3825.
Messenger et al., "Minoxidil: Mechanisms of Action on Hair Growth", British Journal of Dermatology, 2004, 150:186-194.
Metronidazole (Veterinary-Systemic), The United States Pharmacopeial Convention, 2007, retrieved on Sep. 10, 2009, www.usp.org/pdf/EN/veterinary/metronidazole.pdf, 4 pages.
Metz et al., "A Phase I Study of Topical Tempol for the Prevention of Alopecia Induced by Whole Brain Radiotherapy," Clinical Cancer Research, Oct. 2004, 10:6411-6417.
Meucci et al., "Ascorbic Acid Stability in Aqueous Solutions", Acta Vitaminol Enzymol, 1985, 7(3-4):147-153 (English Abstact).
Milton, D.T. et al. (2006) "A Phase I/II Study of Weekly High-Dose Erlotinib in Previously Treated Patients With Nonsmall Cell Lung Cancer" *Cancer*, 107:1034-1041.
Mineral Oil USP, U.S. Department of Health & Human Services, Chemical Abstracts Service Registry No. 8012-95-1, 2011, 7 pages.
Minocycline (DB01017), Drug Bank, Feb 8, 2013, retrieved on Aug. 15, 2013, <http://www.drugbank.ca/drugs/DB01017>, 10 pages.
Minocycline, Wikipedia, The free encyclopedia, retrieved on Oct. 21, 2011, http://en.wikipedia.org/wiki/Minocycline, 7 pages.
MMP Inc., International Development and Manufacturing, "Formulating specialties," retrieved on Feb. 2, 2010, http://mmpinc.com, 3 pages.
Molan, "World Wide Wounds: Honey as a topical antibacterial agent for treatment of infected wounds," Dec. 2001, retrieved May 7, 2008, http://www.worldwidewounds.com/2001/november/Molan/honey-as-topical-agent.html, 13 pages.
*Molins PLC v. Textron Inc.*, 48 F.3d 1172, 33 USPQ2d 1823 (Fed. Cir. 1995), 19 pages.
Morgan et al., "Enhanced Skin Permeation of Sex Hormones with Novel Topical Spray Vehicles," Journal of Pharmaceutical Sciences, Oct. 1998, 87(10):1213-1218.
Mousse, Merriam-Webster Online Dictionary, retrieved on Dec. 8, 2008, http://www.merriam-webster.com/dictionary/mousse, 2 pages.
Musial, W. and A. Kubis (2004) "Carbopols as factors buffering triethanolamine interacting with artificial skin sebum" *Polim Med*, 34(4):17-30 (Abstract).
Natural Skincare Authority, "Disodium EDTA: Cosmetic Toxin Data," 2011, retrieved on Nov. 17, 2013, http://www.natural-skincare-authority.com/DISODIUM-EDTA.html, 4 pages.
Neutrogena Clinical SPF 30 Facial Lifting Wrinkle Treatment, Apr. 28, 2010, retrieved on Sep. 11, 2010, http://www.cosmetoscope.com/2010/04/neutrogea-clinical-with-johnson-johnsons-cytomimic-techology/, 5 pages.
Neves et al., "Rheological Properties of Vaginal Hydrophilic Polymer Gels," *Current Drug Delivery*, 2009, 6:83-92.
New Nanomaterials to Deliver Anticancer Drugs to Cells Developed, Science Daily, Jun. 2007, retrieved on Oct. 14, 2013, <URL: http://www.sciencedaily.com/releases/2007/06/070607112931.htm>, 3 pages.
Nietz, "Molecular orientation at surfaces of solids," J. Phys. Chem., 1928, 32(2): 255-269.
Niram Chemicals, Chemical products—Cetostearyl Alcohol, Cetyl Alcohol, Stearyl Alcohol and Polyethylene Glycol Importer & Supplier, retrieved on Jul. 17, 2012, http://www.indiamart.com/niramchemicals/chemicals.html, 7 pages.

(56) References Cited

OTHER PUBLICATIONS

Novartis "Lamisil®" Product Information, T2001-29 [online]. Retrieved from: http://www.fda.gov/downloads/Drugs/DrugSafety/PostmarketDrugSafetyInformationforPatientsandProviders/ucm052213.pdf; Published: Apr. 2001, 8 pages.

Oh et al., "Antimicrobial activity of ethanol, glycerol monolaurate or lactic acid against *Listeria moncylogenes*," Int. J. Food Microbiology, 1993, 20:239-246.

Olsen et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, Nov. 2007, 57:767-774.

Om-Cinnamate, MakingCosmetics.com, retrieved on Sep. 26, 2009, http://www.makingcosmetics.com/sunscreens/OM-Cinnamate-p102.html, 1 page.

Omega-9 Fatty Acids (Oleic Acid), Orthomolecular.org, Dec. 2004, retrieved on Aug. 15, 2014, http://orthomolecular.org/nutrients/omega9.html, 1 page.

Optimization of Nano-Emulsions Production by Microfluidization, European Food Research and Technology. Sep. 2007, 22:5-6 (English Abstract).

Oranje et al., "Topical retapamulin ointment, 1%, versus sodium fusidate ointment, 2%, for impetigo: a randomized, observer-blinded, noninferiority study," Dermatology, 2007, 215(4):331-340.

Osborne and Henke, "Skin Penetration Enhancers Cited in the Technical Literature," Pharm. Technology, Nov. 1997, 21(11):58-86.

Padhi et al., "Phospho-olivines as positive-electrode materials for rechargeable lithium batteries," J. Electrochemical Soc., Apr. 1997, 144(4): 1188-1194.

Padi and Kulkarni, "Minocycline prevents the development of neuropathic pain, but not acute pain: possible anti-inflammatory and antioxidant mechanisms," Eur J. Pharmacol, 2008, 601:79-87.

Pakpayat et al., "Formulation of Ascorbic Acid Microemulsions with Alkyl Polyglycosides", European Journal of Pharmaceutics and Biopharmaceutics, 2009, 72:444-452.

Palamaras and Kyriakis, "Calcium antagonists in dermatology: a review of the evidence and research-based studies," Derm. Online Journal, 2005, 11(2):8.

Passi et al., "Lipophilic antioxidants in human sebum and aging," Free Radical Research, 2002,36(4):471-477.

Pharmaceutical Benefits Advisory Committee (PBAC) of Australia. PBAC *Public Summary Document-Nov. 2014 Meeting* (5 pages).

Pendergrass et al., "The shape and dimension of the human vagina as seen in three-dimensional vinyl polysiloxane casts," Gynecol Obstet. Invest., 1996, 42(3):178-82 (Abstract).

Penreco, "Intelligent Gel Technology Product Specifications," Rev. Jun. 2016 (2 pages).

Permethrin (Insecticide), Wildpro, retrieved on Jun. 4, 2015, http://wildpro.twycrosszoo.org/S/00Chem/ChComplex/perm.htm, 5 pages.

Perotti et al., "Topical Nifedipine With Lidocaine Ointment vs. Active Control for Treatment of Chronic Anal Fissure," Dis Colon Rectum, 2002, 45(11):1468-1475.

Polystyrene, Wikipedia, the free encyclopedia, retrieved Apr. 21, 2014, http://web.archive.org/web/20060312210423/http://en.wikipedia.org/wiki/Polystyrene, 4 pages.

PPG-40-PEG-60 Lanolin Oil, Environmental Working Group, 2010, retrieved on May 19, 2010, http://www.cosmeticsdatabase.com/ingredient/722972/PPG-40-PEG-60_Lanolin_Oil/?ingred06=722972., 3 pages.

Prevent, The American Heritage Dictionary of the English Language, 2007, retrieved on Oct. 9, 2010, http://www.credoreference.com/entry/hmdictenglang/prevent, 1 page.

Product Data Sheet for Meclocycline, bioaustralis fine chemicals, Jun. 28, 2013, 1 page.

Promius™ Pharma LLC (2012) *Scytera™ (coal tar) Foam, 2%*. Product Information Sheet, 1 page.

Prud'Homme et al., Foams: theory, measurements and applications, Marcel Dekker, Inc., 1996, 327-328.

Purcell, "Natural Jojoba Oil Versus Dryness and Free Radicals," Cosmetics and Toiletries Manufacture Worldwide, 1988, 4 pages.

Purdy et al., "Transfusion-transmitted malaria: unpreventable by current donor exclusion guidelines?" Transfusion, Mar. 2004, 44:464.

Raschke et al., "Topical Activity of Ascorbic Acid: From In Vitro Optimization to In Vivo Efficacy", Skin Pharmacology and Physiology, Jul./Aug. 2004, 17(4):200-206 (Abstract).

Ravet et al., "Electroactivity of natural and sythetic triphylite," J. Power Sources, 2001, 97-98: 503-507.

Raymond, "Iodine as an Aerial Disinfectant," J. Hygiene, May 1946, 44(5):359-361.

Reaction Rate, Wikipedia, the free encyclopedia, retrieved on Dec. 18, 2011, en.wikipedia.org/wiki/Reaction_rate, 6 pages.

Receptacle, Merriam Webster, retrieved on Jul. 12, 2011, http://www.merriam-webster.com/dictionary/receptacle, 1 page.

Refina, "Viscosity Guide for Paints, Petroleum & Food Products," accessed Mar. 4, 2015, http://www.refina.co.uk/webpdfs/info_docs/Viscosity_guide_chart.pdf, 2 pages.

Regulation (EC) No. 2003/2003 of the European Parliament and of the Council, Official Journal of the European Union, Oct. 13, 2003, 2 pages.

Repa et al. "All-trans-retinol is a ligand for the retinoic acid receptors," Proc. Natl. Acad Sci, USA, Aug. 1993, 90: 7293-7297.

Reregistration Eligibility Decision for Pyrethrins, EPA, Jun. 7, 2006, 108 pages.

Richwald, "Imiquimod", Drugs Today, 1999, 35(7):497 (Abstract).

Rieger and Rhien, "Emulsifier Selection/HLB," Surfactants in Cosmetics, 129, 1997.

Rohstoffinformationen, Hoffmann Mineral, 2008, 8 pages (with English translation).

Rosacea, Clinuvel Pharmaceuticals, 2010, retrieved on Sep. 9, 2010, http://clinuvel.com/skin-conditions/common-skin-conditions/rosacea#h0-6-prevention, 5 pages.

Rowe et al., "Glyceryl Monooleate," Handbook of Pharmaceutical Excipients, 2011, 10 pages, retrieved on Dec. 19, 2011, http://www.medicinescomplete.com/mc/excipients/current/1001938996.htm?q=glyceryl%20monooleate&t=search&ss=text&p=1# hit.

Rowe et al., "Octyldodecanol," Handbook of Pharmaceutical Excipients, 2011, 9 pages, retrieved on Dec. 19, 2011, URL:http://www.medicinescomplete.com/mc/excipients/current/1001942450.htm?q=octyldodecanol&t=search&ss=text&p=1# hit.

Rowe et al., "Sucrose Palmitate," Handbook of Pharmaceutical Excipients, 2011, 11 pages, retrieved on Dec. 19, 2011, URL:http://www.medicinescomplete.com/mc/excipients/current/EXP-TD-c46-mn0001.htm?q=sucrose%20stearate&t=search&ss=text&p=1# hit.

Rowe et al., "Sucrose Stearate," Handbook of Pharmaceutical Excipients, 2011, 11 pages, retrieved on Dec. 19, 2011, URL:http://www.medicinescomplete.com/mc/excipients/current/EXP-TD-cll-mnOOOI-mnOOOI.htm?q=sucrose%20stearate&t=search&ss=text&p=3# hit.

Rses (Oil in Refrigerator Systems, Service Application Manual, 2009).

Rutledge, "Some corrections to the record on insect repellents and attractants," J. Am. Mosquito Control Assoc, Dec. 1988, 4(4): 414-425.

Sakai et al., "Characterization of the physical properties of the stratum corneum by a new tactile sensor," Skin Research and Technology, Aug. 2000, 6:128-134.

Sanders et al., "Stabilization of Aerosol Emulsions and Foams," J. Soc. Cosmet. Chem., 1970, 21:377-391.

Sarpotdar, P.P. et al. (Jan. 1986) "Effect of Polyethylene Glycol 400 on the Penetration of Drugs Through Human Cadaver Skin In Vitro" *J Pharma Sci,* 75(1):26-28.

Savin et al., "Tinea versicolor treated with terbinafine 1% solution," Int J. Dermatol, Nov. 1999; 38(11): 863-865.

Schaefer, "Silicone Surfactants," Tenside Surf. Det., 1990, 27(3): 154-158.

Schmidt, "Malassezia furfur: a fungus belonging to the physiological skin flora and its relevance in skin disorders," Cutis, Jan. 1997, 59(1):21-24 (Abstract).

Schmolka, "A review of block polymer surfactants," Journal of the American Oil Chemists Society, Mar. 1977, 54: 110-116.

(56) References Cited

OTHER PUBLICATIONS

Schott, "Rheology," Remington's Pharmaceutical Sciences, 17th Edition, 1985, 330-345.

Schutze, "Iodine and Sodium Hypochlorite as Wound Disinfectants," The British Medical Journal, 1915, 921-922.

Sciarra, "Aerosol Technology," *Kirk-Othmer Encyclopedia of Chemical Technology*, Jul. 2012, 20 pages.

Scientific Discussion for the Approval of Aldara, EMEA, 2005, 10 pages.

Scott, "A Practical Guide to Equipment Selection and Operating Techniques," Pharmaceutical Dosage Forms: Disperse Systems, vol. 3, Copyright 1998, 291-362.

Scully et al., "Cancers of the oral mucosa treatment and management," Medscape Drugs, Diseases and Procedures, Apr. 20, 2012, retrieved on Oct. 12, 2013, <http://emedicine.medscape.com/article/1075729-treatment>, 10 pages.

Seborrheic Dermatitis, retrieved on Sep. 9, 2010, http://www.cumc.columbia.edu/student/health/pdf/R-S/Seborrhea%20Dermatitis.pdf, 2 pages.

Security Datasheet, Luvitol EHO, Cetearyloctanoat, Nov. 27, 2013, 10 pages.

Sehgal, " Ciclopirox: a new topical pyrodonium antimycotic agent: A double-blind study in superficial dermatomycoses," *British Journal of Dermatology*, 1976, 95:83-88.

Sharp, "Oil," Dictionary of Chemistry, Copyright 1990, 286.

Shear et al., "Pharmacoeconomic analysis of topical treatments for tinea infections," Pharmacoeconomics, Mar. 1995, 7(3):251-267.

Shear, Vocabulary.com, retrieved on Aug. 23, 2013, <URL: https://www.vocabulary.com/dictionary/shear>, 3 pages.

Sheer, Vocabulary.com, retrieved on Aug. 23, 2013, https://www.vocabulary.com/dictionary/sheer, 3 pages.

Shemer, A. et al. (2016) "Topical minocycline foam for moderate to severe acne vulgaris: Phase 2 randomized double-blind, vehicle-controlled study results" *J Am Acad Dermatol*, 74(6):1251-1252.

Sheu et al., "Effect of Tocopheryl Polyethylene Glycol Succinate on the Percutaneous Penetration of Minoxidil from Water/Ethanol/Polyethylene Glycol 400 Solutions," Drug Dev. Ind. Pharm., Jun. 2006, 32(5):595-607 (Abstract).

Shim et al., "Transdermal Delivery of Mixnoxidil with Block Copolymer Nanoparticles," J. Control Release, Jul. 2004, 97(3):477-484 (Abstract).

Shrestha et al., "Forming properties of monoglycerol fatty acid esters in nonpolar oil systems," Langmuir, 2006, 22: 8337-8345.

Sigma-Aldrich. http://www.sigmaaldrich.com/catalog/product/sial/p1754?lang=en® ion=. Published :Mar. 5, 2014.

Sigma Aldrich, "Surfactants Classified by HLB Numbers" 2017 [online]. Retrieved from the Internet: www.sigmaaldrich.com/materials-science/material-science-products.html?TablePage=22686648, on Jul. 8, 2017 (3 pages).

Silicone, Oxford Dictionaries Online, retrieved on Apr. 19, 2011, http://www.oxforddictionaries.com/definition/silicone?view=uk, 1 page.

Simoni et al., "Retinoic acid and analogs as potent inducers of differentiation and apoptosis. New promising chemopreventive and chemotherapeutic agents in oncology," Pure Appl Chem., 2001, 73(9):1437-1444.

Simovic et al., "The influence of Processing Variables on Performance of O/W Emulsion Gels Based on Polymeric Emulsifier (Pemulen® TR-2NF)," International Journal of Cosmetic Science, Dec. 2001, 21(2)119-125 (Abstract).

Smith, "Hydroxy acids and skin again," Soap Cosmetics Chemical Specialties, Sep. 1993, 69(9):54-59.

Smith, "Sore Nipples," Breastfeeding Mom's Sore Nipples / Breastfeeding Basics, retrieved on Feb. 8, 2012, http://breastfeedingbasics.com/articles/sore-nipples, 9 pages.

Softemul-165: Product Data Sheet, Mohini Organics PVT LTD, retrieved Apr. 10, 2014, http://www.mohiniorganics.com/Softemul165.html#, 1 page.

Solans et al., "Overview of basic aspects of microemulsions," Industrial Applications of Microemulsions, New York, 1997, 1-17.

Solodyn® (Minocycline HCI, USP) Prescribing Information; revised Jun. 2016, 2 pages.

Sonneville-Aubrun et al., "Nanoemulsions: A New Vehicle for Skincare Products," Advances in Colloid and Interface Science, 2004, 108-109:145-149.

Spa Collections, Ag & Co. Essential oil workshop, retrieved on Jan. 31, 2010, http://www.agworkshop.com/p3.asp, 1 page.

Squillante et al., "Codiffusion of propylene glycol and dimethyl isosorbide in hairless mouse skin," European J. Pharm. Biopharm., 1998, 46:265-271.

Squire and Goode, "A randomized, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat., Jun. 2002, 13(2):51-60 (Abstract).

Sreenivasa et al., "Preparation and Evaluation of Minoxidil Gels for Topical Application in Alopecia," Indian Journal of Pharmaceutical Sciences, 2006, 68(4):432-436.

Sreenivasan, B. et al. (1956)"Studies on Castor Oil. I. Fatty Acid Composition of Castor Oil" *J Am Oil Chem Soc*, 33:61-66.

Stehle et al., "Uptake of minoxidil from a new foam formulation devoid of propylene glycol to hamster ear hair follicles," J. Invest. Dermatol., 2005, 124(4): A101 (Abstract).

Sugisaka et al., "The Physicochemical Properties of Imiquimod, The First Imidazoquinoline Immune Response Modifier", Pharmaceutical Research, Nov. 1997, 14(11):S475, Abstract 3030.

*Sun Pharmaceutical Industries Ltd. v. Eli Lilly and Co.*, 611 F.3d 1381, 95 USPQ2d 1797 (Fed. Cir. 2010),7 pages.

Sung, J.H. et al. (2010) "Gel characterisation and in vivo evaluation of minocycline-loaded wound dressing with enhanced wound healing using polyvinyl alcohol and chitosan" *Intl J Pharmaceut*, 392:232-240.

Surfactant, Wikipedia, the free encyclopedia, retrieved on Oct. 24, 2010, http://en.wikipedia.org/wiki/Surfactant, 7 pages.

Tadros, "Surfactants in Nano-Emulsions." Applied Surfactants: Principles and Applications, 2005, 285-308.

Tamarkin, D. (2013) "Foam: A Unique Delivery Vehicle for Topically Applied Formulations" in: *Formulating Topical Applications—a Practical Guide*. Dayan N, Ed., Carol Stream, IL: CT Books, Chapter 9, pp. 233-260.

Tan et al., "Effect of Carbopol and PolyvinYlpyrrolidone on the Mechanical, Rheological, and Release Properties of Bioadhesive Polyethylene Glycol Gels," AAPS PharmSciTech, 2000; 1(3) Article 24, 10 pages.

Tanhehco, "Potassium Channel Modulators as Anti-Inflammatory Agents", Expert Opinion on Therapeutic Patents, Jul. 2001, 11(7):1137-1145 (Abstract).

Tarumoto et al., "Studies on toxicity of hydrocortisone 17-butyrate 21-propionate-1. Acute toxicity of hydrocortisone 17-butyrate 21-propionate and its analogues in mice, rats and dogs (author's transl)," J Toxicol Sci., Jul. 1981, 6:1-16 (Abstract).

Tata et al., "Penetration of Minoxidil from Ethanol Propylene Glycol Solutions: Effect of Application Volume On Occlusion," Journal of Pharmaceutical Sciences, Jun. 1995, 84(6):688-691.

Tata et al., "Relative Influence of Ethanol and Propylene Glycol Cosolvents on Deposition of Minoxidil into the Skin," Journal of Pharmaceutical Sciences, Jul. 1994, 83(10):1508-1510.

Tavss et al., "Anionic detergent-induced skin irritation and anionic detergent-induced pH rise of bovine serum albumin," *J. Soc. Cosmet. Chem.*, Jul./Aug. 1988, 39:267-272.

TCI America, Safety Data Sheet; Product Name: Squalane. Product Code: H0096 [online]. Retrieved from: https://www.spectrumchemical.com/MSDS/TCI-H0096.pdf. Revised: Oct. 6, 2014, 5 pages.

Tea Tree Oil, LookChem, Chemical Abstract No. 68647-73-4, 2012, 2 pages.

The HLB System—A Time-Saving Guide to Emulsifier Selection, ICI Americas Inc., Mar. 1980, 1-22.

The United States Pharmacopeia: The National Formulary, USP23/NF18, US Pharmacopoeia, Jan. 1995, p. 10-14.

Third Party Submission in Published Patent Application, U.S. Appl. No. 12/014,088, dated Feb. 4, 2009, 4 pages.

(56) References Cited

OTHER PUBLICATIONS

Thorgeirsdottir et al., "Antimicrobial activity of monocaprin: a monoglyceride with potential use as a denture disinfectant," Acta Odontologica Scandinavica, Feb. 2006, 64:21-26 (Abstract only).
Tirumala et al., "Abstract: D28.00011: Enhanced order in thinfilms of Pluronic (A-B-A) and Brij (A-B) Block copolymers blended with poly (acrylic acid)," Session D28: Block Copolymer Thin Films, Mar. 13, 2006, 1 page, Abstract.
Tjulandin, S. et al. (2013) "Phase I, dose-finding study of AZD8931, an inhibitor of EGFR (erbB1), HER2 (erbB2) and HER3 (erbB3) signaling, in patients with advanced solid tumors" Invest New Drugs, 32(1):145-153.
Todd et al., "Volatile Silicone Fluids for Cosmetic Formulations," Cosmetics and Toiletries, Jan. 1976, 91:27-32.
Torma et al., "Biologic activities of retinoic acid and 3, 4-Didehydroretinoic acid in human keratinocytes are similar and correlate with receptor affinities and transactivation properties," J. Invest. Dermatology, 1994, 102: 49-54.
Torres-Rodriguez, "New topical antifungal drugs," Arch Med Res., Winter 1993, 24(4): 371-375 (Abstract).
Toxicology and Carcinogenesis Studies of T-Butyl Alcohol (CAS No. 75-65-0) in F344/N Rats and B6C3F1 Mice (Drinking Water Studies), May 1995, retrieved on Dec. 9, 2008, http://ntp.niehs.nih.gob/?objectid-=0709F73D-A849-80CA-5FB784E86613576D1, 4 pages.
Trofatter, "Imiqimod in clinical practice", European Journal of Dermatology, Oct./Nov. 1998, 8(7 Supp.):17-19 (Abstract).
Tsai et al., "Drug and Vehicle Deposition from Topical Applications: Use of in Vitro Mass Balance Technique with Minoxidil Solutions", J. Pharm. Sci., Aug. 1992, 81(8):736-743 (Abstract).
Tsai et al., "Effect of Minoxidil Concentration on the Deposition of Drug and Vehicle into the Skin," International Journal of Pharmaceutics, 1993, 96(1-3):111-117 (Abstract).
Tsai et al., "Influence of Application Time and Formulation Reapplication on the Delivery of Minoxidil through Hairless Mouse Skin as Measured in Franz Diffusion Cells," Skin Pharmacol., 1994, 7:270-277.
Tyring, "Immune-Response Modifiers: A New Paradigm in the Treatment of Human Papillomavirus," Current Therapeutic Research, Sep. 2000, 61(9):584-596 (Abstract).
Tzen et al. "Surface Structure and Properties of Plant Seed Oil Bodies," Department of Botany and Plant Sciences, University of California, Riverside, California 92521, Apr. 15, 1992, 9 pages.
Tzen et al., "Lipids, proteins and structure of seed oil bodies from diverse species," Plant Physiol., 1993, 101:267-276.
U.S. Final Office Action for U.S. Appl. No. 11/430,437, Tamarkin et al., dated Dec. 16, 2008, 24 pages.
U.S. Office Action for U.S. Appl. No. 11/430,437, Tamarkin et al., dated May 9, 2008, 27 pages.
U.S. Office Action from U.S. Appl. No. 11/430,599, dated Jul. 28, 2008, 59 pages.
Uner et al., "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel," Pharmazie, 2005, 60:751-755.
United States Standards for Grades of Olive Oil and Olive-Pomace Oil, United States Dept. of Agriculture, Oct. 25, 2010, 21 pages.
Valenta, "Effects of Penetration Enhancers on the In-vitro Percutaneous Absorption of Progesterone," J. Pharm. Pharmacol., 1997, 49: 955-959.
Van Cutsem et al., "The anti-inflammatory effects of ketoconazole," J. Am. Acad. Dermatol., Aug. 1991, 25(2):257-261.
Van Slyke, "On the measurement of buffer values and on the relationship of buffer value to the dissociation constant of the buffer and the concentration and reaction of the buffer solution," J. Biol. Chem., 1922, 52:525-570.
Vera et al., "Scattering optics of Foam," Applied Optics, Aug. 20, 2001, 40(24):4210-4214.

Veron et al., "Stability of Minoxidil Topical Formulations", Ciencia Pharmaceutica, 1992, 2(6):411-414 (Abstract).
Versagel® M Series, Mineral Oil Moisturizing Gels. Product Bulletin, retrieved from https://archive.org/web/, as archived Oct. 15, 2006, 3 pages.
View of NCT01171326 on Dec. 7, 2010, ClinicalTrials.gov archive, Dec. 7, 2010, retrieved on Sep. 9, 2013, http://clinicaltrials.gov/archive/NCT01171326/2010_12_07, 4 pages.
View of NCT01362010 on Jun. 9, 2011, ClinicalTrials.gov archive, Jun. 9, 2011, retrieved on Sep. 9, 2013, < http://clinicaltrials.gov/archive/NCT01362010/2011_06_09>, 3 pages.
Wang and Chen, "Preparation and surface active properties of biodegradable dextrin derivative surfactants," Colloids and Surfaces A: Physicochemical and Engineering Aspects, 2006, 281(1-3):190-193.
Water Jel Technologies, "Material Safety Data Sheet for Neomycin Antibiotic Ointment," Dec. 1, 2004, 7 pages.
WebMD (2014) "Psoriasis Health Center" [online]. Retrieved Apr. 13, 2015; retrieved from the Internet: http://www.webmd.com/skin-problems-and-treatments/psoriasis/psoriasis-symptoms, 3 pages.
WebMD (2014) "Understanding Rosacea—the Basics" [online]. Retrieved Apr. 13, 2015; retrieved from the Internet: http://www.webmd.com/skin-problems-and-treatments/understanding-rosacea-basics (5 pages).
WebMD (2017) "User Reviews & Ratings—Scytera topical" [online]. Retrieved Mar. 1, 2017; retrieved from the Internet: http://www.webmd.com/drugs/drugreview-151502-Scytera+topical.aspx?drugid=151502&drugname=Scytera+topical&sortby=3 (2 pages).
Weindl et al., "Hyaluronic acid in the treatment and prevention of skin diseases: molecular biological, pharmaceutical and clinical aspects," Skin Pharmacology and Physiology, 2004, 17: 207-213.
Wenninger et al., "International Cosmetic Ingredient Dictionary and Handbook," The Cosmetic, Toiletry, and Fragrance Association, Washington, DC., 1997, vol. 1, 4 pages.
Wermuth, "Similarity in drugs: reflections on analogue design," Drug Discovery Today, Apr. 2006, 11(7/8):348-354.
What is CP Serum, Skin Biology, retrieved on Dec. 1, 2008, http://web.archive.org/web/20030810230608/http://www.skinbio.com/cpserum.-html, 21 pages.
What Is TSC?, Tuberous Sclerosis Alliance, Jan. 1, 2005, retrieved on Feb. 6, 2014, http://www.tsalliance.org.pages.aspx?content=2, 3 pages.
Williams et al., "Acne vulgaris," Lancet, 2012, 379:361-372.
Williams et al., "Scale up of an olive/water cream containing 40% diethylene glycol monoethyl ether," Dev. Ind. Pharm., 2000, 26(1):71-77.
Williams et al., "Urea analogues in propylene glycol as penetration enhancers in human skin," International Journal of Pharmaceutics, 1989, 36, 43-50.
Wormser et al., "Protective effect of povidone-iodine ointment against skin lesions induced by sulphur and nitrogen mustards and by non-mustard vesicants," Arch. Toxicol., 1997, 71, 165-170.
Wormser, "Early topical treatment with providone-iodine ointment reduces, and sometimes prevents, skin damage following heat stimulus," Letter to the Editor, Burns, 1998, 24:383.
Wrightson, W.R. et al. (1998) "Analysis of minocycline by high-performance liquid chromatography in tissue and serum" J Chromatography B, 706:358-361.
Wu et al., "Interaction of Fatty Acid Monolayers with Cobalt Nanoparticles," Nano Letters, 2004, 4(2): 383-386.
Yamada et al., "Candesartan, an angiotensin II receptor antagonist, suppresses pancreatic inflammation and fibrosis in rats," J. Pharmacol. Exp. Ther., 2003, 307(1)17-23.
Zeichner, J.A. (2010) "Use of Topical Coal Tar Foam for the Treatment of Psoriasis in Difficult-to-treat Areas" J Clin Aesthet Dermatol, 3(9):37-40.
Zinc Oxide, Knovel, 2006, retrieved on Apr. 18, 2012, http://www.knovel.com/web/portal/knovel_content?p_p_id=EXT_KNOVEL_CONTENT . . . , 2 pages.
Ziolkowsky, "Moderne Aerosolschaume in der Kosmetik (Modern Aerosol Foams in Chemical and Marketing Aspects)" Seifen-Ole-Fette-Wachse, Aug. 1986, 112(13): 427-429 (with English translation).

Figure 1

|  | Control | Classic Emollient | D52 (containing petrolatum) | D50 (containing urea) | D51 (containing water) |
|---|---|---|---|---|---|
| Increase in skin hydration 4 hours after application | 19.5 | 30.2 | 42.0 | 42.8 | 41.1 |

FOAMABLE VEHICLES AND PHARMACEUTICAL COMPOSITIONS COMPRISING APROTIC POLAR SOLVENTS AND USES THEREOF

This application is a Continuation of U.S. application Ser. No. 16/236,704, filed Dec. 31, 2019, which is a Continuation of U.S. application Ser. No. 15/883,134, filed Jan. 30, 2018, which is a Continuation of U.S. application Ser. No. 15/639,114, filed Jun. 30, 2017, which is a Division of U.S. application Ser. No. 13/263,201, filed Dec. 28, 2011, which is a § 371 National Stage entry of PCT/IB2010/001126, filed Apr. 28, 2010, which claims priority to U.S. Provisional Application No. 61/173,378, filed Apr. 28, 2009, all of which are incorporated herein by reference.

BACKGROUND

This invention relates to foamable pharmaceutical and cosmetic compositions and foams, containing aprotic polar solvents and uses.

External topical administration is an important route for the administration of drugs in disease treatment. Administration into body cavities is gaining in importance. Many groups of drugs, including, for example, antibiotic, antifungal, anti-inflammatory, anesthetic, analgesic, anti-allergic, corticosteroid, retinoid and anti-proliferative medications are preferably administered in creams and ointment.

There are many different types of foams and within each foam type there are many levels of qualities. For example, the froth on the head of beer, lather of shampoo, and lather of shaving cream have been loosely described as foam but all are different from one another. Such differences speak to usability applicability. At one end of the cosmetic or pharmaceutical foam spectrum, the foam can be long-lasting and not readily breakable upon mechanical stimulation like shaving foams. Such foams lack suitability for pharmaceutical use since they lather with mechanical stimulation and require washing off. At the other end of the spectrum, the foam can be quick breaking without mechanical stimulation and collapse upon release. Such foams can be inconvenient since they can disappear rapidly before they can be conveniently applied to the intended target. Yet another type of foam is delayed foaming gel which is expelled as a gel but is said to expand into a type of foam on exposure to body temperature. Such expansion can be slow or delayed and inconvenient. Foams are considered a more convenient vehicle for topical delivery of active agents. There are several types of topical foams, including aqueous foams, such as commonly available shaving foams; hydroalcoholic foams; emulsion-based foams, comprising oil and water components; and oleaginous foams, which consist of high oil content. In skin therapy, oil containing foams are preferred, since oil contributes to skin protection and moisturization, which improve the therapeutic effect of the formulation. Typically foams are made using liquefied hydrocarbon gas propellant, such as propane, butane and isobutene, or hydro-fluoro carbon propellants.

Formulations containing aprotic polar solvents, such as Dimethyl sulfoxide ("DMSO"), have been occasionally known. However, these formulations have only been known as creams, gels or liquid formulations. Yet, despite the many benefits of pharmaceutical and cosmetic foam formulations, until now DMSO-containing formulations have not been developed in a commercial foam form.

SUMMARY

The present invention relates to foamable pharmaceutical and cosmetic compositions and foams, comprising aprotic polar solvents.

There is provided, easy to use, stable foamable formulations and foams containing aprotic polar solvents, with improved delivery properties, especially for treatment of dermal and mucosal tissues.

In one or more embodiments waterless formulations comprising at least one aprotic polar solvent are provided. In certain embodiments the waterless formulations are formulated with surfactant. In some embodiments they may also comprise a polymer and or a foam adjuvant. In certain other embodiments they are formulated without surfactant. Surfactant free formulations may in one or more embodiments comprise a polymer and or a foam adjuvant and preferably both. In one or more embodiments the aprotic waterless formulation comprises a short chain alcohol. In one or more embodiments the waterless formulation may form an emulsion, for example between a hydrophobic phase and an aprotic phase. In certain embodiments the formulation may be a single phase until addition of propellant. In one or more embodiments an emulsion is formed or reformed after addition of hydrophobic propellant.

In one or more other embodiments water comprising formulations comprising at least one aprotic polar solvent are provided. In certain embodiments the water comprising formulations are formulated with surfactant. In some embodiments they may also comprise a polymer and or a foam adjuvant. In certain other embodiments they are formulated without surfactant. Surfactant free formulations may in one or more embodiments comprise a polymer and or a foam adjuvant and preferably both. In one or more embodiments the aprotic-aqueous formulation comprises a short chain alcohol. In one or more embodiments the water comprising formulation may form an emulsion, for example between a hydrophobic phase and an aqueous aprotic phase. In certain embodiments the formulation may be a single phase until addition of propellant. In one or more embodiments an emulsion is formed or reformed after addition of hydrophobic propellant.

According to one or more embodiments the foamable carrier comprises:
1. An aprotic polar solvent;
2. At least one foaming or stabilizing member, selected from the group, consisting of:
   a. a surface-active agent;
   b. a foam adjuvant; and
   c. a polymeric agent;
   and
3. A liquefied or compressed gas propellant at a concentration of about 3% to about 25% by weight of the total composition.

According to one or more embodiments the foamable carrier comprises:
1. An aprotic polar solvent;
2. At least one foaming or stabilizing member, selected from the group, consisting of:
   a. a surface-active agent;
   b. a foam adjuvant; and
   c. a polymeric agent;
3. At least one solvent, selected from the group, consisting of:
   a. water
   b. a protic polar solvent; and
   c. a hydrophobic carrier;

and
4. A liquefied or compressed gas propellant at a concentration of about 3% to about 25% by weight of the total composition.

According to one or more embodiments the foamable composition is aqueous and comprises two or more of the foaming or stabilizing members. In one or more embodiments the composition further comprises one of a protic polar solvent or a hydrophobic carrier or mixtures thereof.

According to one or more embodiments the foamable carrier is water-containing (aqueous) and comprises:
1. An aprotic polar solvent
2. At least two foaming or stabilizing members, selected from the group, consisting of:
   a. a surface-active agent;
   b. a foam adjuvant; and
   c. a polymeric agent;
3. Water and optionally at least one solvent, selected from the group, consisting of:
   a. a protic polar solvent; and
   b. a hydrophobic carrier;
   and
4. A liquefied or compressed gas propellant at a concentration of about 3% to about 25% by weight of the total composition.

According to one or more certain embodiments the aqueous foamable carrier is aqueous without a hydrophobic carrier and comprises one stabilizing member comprising a non ionic surfactant with a HLB between about 9 to about 16.

According to one or more embodiments, the foamable composition, comprises a therapeutically effective concentration of an aprotic polar solvent, which possesses inherent therapeutic properties.

In preferred embodiments, the therapeutic aprotic polar solvent comprises Dimethyl sulfoxide (DMSO).

The carrier or pharmaceutical or cosmetic composition is stored in a pressurized canister and when released a foam is formed that is thermally stable, yet breaks easily upon application of shear force. So in one or more embodiments the foam composition is breakable. The breakable foam is thermally stable, yet breaks easily upon application of shear force. By thermally stable is meant that the foam is stable for a sufficient period of time—both at room temperature and when applied to the skin or subjected to at temperature of about 36 C—to facilitate easy and relaxed use and allow for possible distractions or interruptions. In one or more embodiments the foam is stable for at least about 30 secs, at least about 40 secs, at least about 50 secs, at least about 60 secs, at least about 80 secs, at least about 100 secs, at least about 120 secs, at least about 140 secs, at least about 160 secs, at least about 180 secs, at least about 210 secs, at least about 240 secs, at least about 270 secs or at least about 300 secs.

In one or more alternative embodiments the foam composition is quick-break or thermolabile. The quick-breaking foam is thermally instable, and collapses easily upon exposure to body temperature without the need to apply shear force. In one or more embodiments the foam has low stability or is unstable and collapses in less than about 30 secs, in less than about 25 secs, in less than about 20 secs, in less than about 15 secs, in less than about 10 secs, or in less than about 5 secs. Foam can be quick-breaking, for example, wherein the foam formulation comprises high levels of a short chain alcohol, such as, ethanol.

According to one or more embodiments the concentration of the aprotic polar solvent, about 3% to about 97% by weight of the total composition.

According to one or more embodiments, the composition comprises a hydrophobic carrier; and the composition is an emulsion between the water/aprotic polar solvent mixture and the hydrophobic carrier.

According to one or more embodiments, the composition is waterless. In some embodiments the composition is waterless and comprises a protic polar solvent or a hydrophobic carrier or mixtures thereof. In certain embodiments, the composition is waterless, and the composition is a waterless emulsion between the aprotic polar solvent and the hydrophobic carrier.

According to one or more embodiments, the composition is substantially waterless.

According to one or more embodiments the foamable carrier is non-aqueous (waterless) and comprises:
1. An aprotic polar solvent
2. At least one foaming or stabilizing member, selected from the group, consisting of:
   a. a surface-active agent;
   b. a foam adjuvant; and
   c. a polymeric agent;
3. Optionally at least one solvent, selected from the group, consisting of:
   a. a protic polar solvent; and
   b. a hydrophobic carrier;
   and
4. A liquefied or compressed gas propellant at a concentration of about 3% to about 25% by weight of the total composition.

According to one or more embodiments, the foamable carrier is substantially non-aqueous (substantially waterless), and comprises:
   a) An aprotic polar solvent
   b) At least one member, selected from the group, consisting of:
      I. a surface-active agent;
      II. a foam adjuvant; and
      III. a polymeric agent;
   c) Up to about 5% water and optionally a solvent, selected from the group, consisting of:
      I. a protic polar solvent; and
      II. a hydrophobic carrier;
      and
   d) A liquefied or compressed gas propellant at a concentration of about 3% to about 25% by weight of the total composition.

According to one or more embodiments, the foamable carrier is substantially waterless, and comprises:
   a) An aprotic polar solvent
   b) At least one member, selected from the group, consisting of:
      I. a surface-active agent;
      II. a foam adjuvant; and
      III. a polymeric agent;
   c) At least two solvents, one of which is water selected from the group, consisting of:
      IV. Up to about 5% water;
      V. a protic polar solvent; and
      VI. a hydrophobic carrier;
      and
   d) A liquefied or compressed gas propellant at a concentration of about 3% to about 25% by weight of the total composition.

According to one or more embodiments, the composition is alcohol-free, or substantially alcohol-free. According to one or more other certain embodiments the composition is alcoholic.

According to one or more embodiments, the composition is a waterless foamable carrier comprising:
a. DMSO
b. At least one foaming or stabilizing member, selected from the group, consisting of:
  i. a solid surface-active agent at room temperature having a HLB of less than about 5;
  ii. a foam adjuvant;
  iii. hydroxypropyl methyl cellulose;
  iv. a surface active agent and a foam adjuvant and or hydroxypropyl methyl cellulose;
  v. a surface active agent and a foam adjuvant and a polymeric agent; and
  vi. a foam adjuvant and a polymeric agent;
c. Optionally or at least one solvent, selected from the group, consisting of:
  i. a protic polar solvent; and
  ii. a hydrophobic carrier;
and
d. A liquefied or compressed gas propellant at a concentration of about 3% to about 25% by weight of the total composition.

wherein the resultant foam formed from the carrier is thermally stable, yet breaks easily upon application of shear force.

According to one or more embodiments, the hydrophobic solvent comprises a petrolatum.

According to one or more embodiments, the protic polar solvent comprises ethanol.

According to one or more embodiments, the composition further comprises urea.

According to one or more embodiments, the composition is a water containing foamable carrier comprising:
a. DMSO
b. At least two foaming or stabilizing members, selected from the group, consisting of:
  i. a surface-active agent;
  ii. a foam adjuvant;
  iii. a polymeric agent; and
  iv. a foam adjuvant and a polymeric agent;
c. Water and optionally or at least one solvent, selected from the group, consisting of:
  i. a protic polar solvent; and
  ii. a hydrophobic carrier;
and
d. A liquefied or compressed gas propellant at a concentration of about 3% to about 25% by weight of the total composition.

wherein the resultant foam formed from the carrier is thermally stable, yet breaks easily upon application of shear force.

According to one or more embodiments, the water is less than about 5% and the formulation is substantially waterless.

According to one or more embodiments the foamable carrier, further comprises an active agent; In one or more additional embodiments, the aprotic polar solvents possesses inherent therapeutic properties and therefore it can be considered as an "active agent".

According to one or more embodiments the method of treating a disorder of a mammalian subject, includes:
administering a foamable therapeutic composition to a target site, the composition comprising:

a. An aprotic polar solvent
b. At least one foaming or stabilizing member, selected from the group, consisting of:
  i. a surface-active agent;
  ii. a foam adjuvant; and
  iii. a polymeric agent;
c. Optionally or at least one solvent, selected from the group, consisting of:
  i. water;
  ii. a protic polar solvent; and
  iii. a hydrophobic carrier;
and
d. A liquefied or compressed gas propellant at a concentration of about 3% to about 25% by weight of the total composition.

According to one or more embodiments the method of treating a disorder of a mammalian subject, includes:
administering a foamable therapeutic composition to a target site, the composition comprising:
1. An aprotic polar solvent;
2. At least two members, selected from the group, consisting of:
  i. a surface-active agent;
  ii. a foam adjuvant; and
  iii. a polymeric agent;
3. At least one solvent, selected from the group, consisting of:
  i. water;
  ii. a protic polar solvent; and
  iii. a hydrophobic carrier;
and
4. A liquefied or compressed gas propellant at a concentration of about 3% to about 25% by weight of the total composition.

According to one or more embodiments, the method comprises a waterless foamable carrier or composition with at least one of a surfactant, a polymer and a foam adjuvant. According to one or more other embodiments, the method comprises a substantially waterless foamable carrier or composition with at least one of a surfactant, a polymer and a foam adjuvant and up to about 5% water. According to one or other embodiments, the method comprises an aqueous carrier or composition with at least two of a surfactant, a polymer and a foam adjuvant.

According to one or more embodiments, the method comprises foamable carrier or composition, further comprises an active agent.

According to one or more embodiments, the method comprises pre-treating the target area with a foamable carrier or composition comprising an agent that can ameliorate or prevent a taste or odor being experienced after a DMSO foam is applied to a target. According to one or more other embodiments, the method comprises treating the target area with a foamable carrier or composition further comprising an agent that can ameliorate or prevent a taste or odor being experienced after a DMSO foam is applied to a target.

According to one or more embodiments the foamable composition, comprises a therapeutically effective concentration of an aprotic polar solvent, which possesses inherent therapeutic properties.

All % values herein are provided on a weight (w/w) basis.

BRIEF DESCRIPTION OF THE DRAWING

FIG. 1 is a Table illustrating increase in skin hydration 4 hours after application of DMSO foamable carriers.

DETAILED DESCRIPTION

Figure 2:
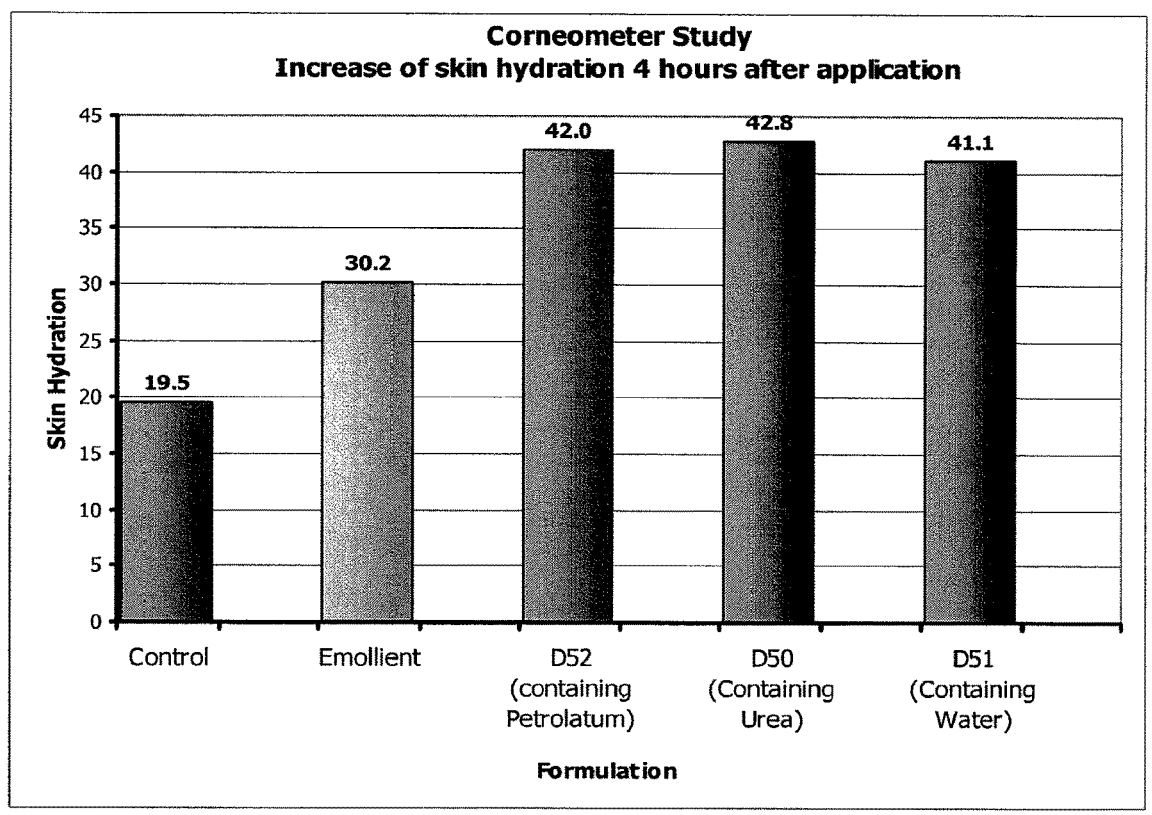
FIG. 2 is a color bar chart illustrating increase in skin hydration 4 hours after application of DMSO foamable carriers.

According to one or more embodiments the present invention includes the embodiments described above in the Summary of the Invention as more particularly detailed, specified and exemplified below.

Aprotic Polar Solvent

Solvents can be broadly classified into polar (hydrophilic) and nonpolar (lipophilic). The polarity can be measured as the dielectric constant or the dipole moment of a compound.

An aprotic solvent is an organic solvent that does not contain an O—H or N—H bond; or does not exchange protons with a substance dissolved in it. In the context herein, the aprotic polar solvent is a solvent with a comparatively high relative permittivity (or dielectric constant), greater than about 15, and a sizable permanent dipole moment, that cannot donate suitably labile hydrogen atoms to form strong hydrogen bonds; and it is miscible in water. Examples of aprotic polar solvents, suitable according to the present invention include, but are not limited to dimethyl sulfoxide (DMSO), dimethylformamide (DMF), acetonitrile, acetone, methyl ethyl ketone, 1,4-Dioxane and tetrahydrofuran (THF). Additional non-limiting examples include N-methylpyrrolidone, pyridine, piperidine, dimethyl ether, hexamethylphosphorotriamide, dimethylformanide, methyl dodecyl sulfoxide, N-methyl-2-pyrrolidone and 1-methyl-2-pyrrolidinone) and azone (1-dodecylazacycloheptan-2-one).

An aprotic solvent can be a defoamer in certain embodiments. It can in certain embodiments act to accelerate the breakdown of the foam and reduce its stability. To an extent this may be countered by adding one or more agents that can stabilize the foam and boost its stability. For example, addition of a polymer and or a foam adjuvant can help to improve the collapse time and likewise slow liquid drainage driven by gravity, which otherwise can and will cause the walls of bubbles to thin and ultimately collapse into adjacent bubble walls that are likewise thinning to form larger bubbles. Examples 1 and 2 indicate, for example, that DMSO is not prone to foaming.

DMSO

Dimethyl sulfoxide (DMSO) is the chemical compound with the formula $(CH_3)_2SO$. This colorless liquid is an important aprotic polar solvent that dissolves both polar and nonpolar compounds and is miscible in a wide range of organic solvents as well as water. It has a distinctive property of penetrating the skin very readily, so that some people report that one can taste it soon after it comes into contact with the skin. In this connection, taking DMSO internally is reported to cause a fish- or oyster-like taste or odor in the mouth. With its high polarity combined with a high dielectric constant, DMSO is known to be an excellent solvent for polar or polarizable organic compounds, but also many acids, alkalis and mineral salts. DMSO is miscible with most co-solvents. The following table provides certain physical characteristics of DMSO and DMF.

|  | DMSO | DMF |
|---|---|---|
| Dielectric constant (25° C.) | 46.4 | 36.7 |
| Polarity (Debye, 25° C.) | 4.3 | 3.8 |
| Boiling point (° C.) | 189 | 153 |
| Flash point (closed cup, ° C) | 87 | 58 |

DMSO can penetrate the skin and other membranes without damaging them and could carry other compounds into a biological system. DMSO has been used most widely as a topical analgesic, in a 70% DMSO, 30% water solution. Laboratory studies suggest that DMSO reduces pain by blocking peripheral nerve C fibers. DMSO also is said to reduce inflammation by several mechanisms. It is further an antioxidant—a scavenger of the free radicals that gather at the site of injury. DMSO also stabilizes membranes and slows or stops leakage from injured cells and is recommended for many inflammatory conditions not caused by infection or tumor. Because DMSO increases the rate of absorption of some compounds through organic tissues including skin and nails, it can be used as a drug delivery system.

In one or more embodiments a method is provided to ameliorate or prevent possible side effects of DMSO such as a taste, which has been described as "garlicy" and a breath odor. As an initial observation although a high proportion of DMSO can be present in the formulations because they are presented as a low density foam it is possible to apply a much thinner layer and cover the same area with a substantially or much smaller amount than a cream or ointment. That being said the position can be further improved by first applying to the target area a composition containing one or more of urea, ethanol, and or lipophilic compounds and then subsequently applying the DMSO foam to the target area. The time interval between the first application and the second application can be about almost immediately afterwards, about 30 secs afterwards, about 1 minute afterwards, about 2 minutes afterwards, about 5 minutes afterwards, about 10 minutes afterwards, about 20 minutes afterwards, about 30 minutes afterwards, about 40 minutes afterwards, about 50 minutes afterwards, about 60 minutes afterwards, or sometimes longer. In one or more embodiments the DMSO presented to the target area simultaneously with another foam containing one or more ingredients known to ameliorate or prevent the taste and odor by using a dual chamber device to apply the two foams such as is described in US publication 2007/0069046 entitled "MEASURE OF CONTENT FROM A PLURALITY OF CONTAINERS" and incorporated herein by reference. In an alternative approach the formulation may itself include one or more ingredients known to ameliorate or prevent the taste and odor.

Concentration

In an embodiment the aprotic polar solvent can be incorporated in the foamable composition of the present invention in a concentration between about 3% and about 98% or between about 10% and about 97%, for example above about 15%, above about 20%, above about 25%, above about 30%, above about 35%, above about; 40%, above about 45%, above about 50%, above about 55%, above about, 60%; above about 70%, above about 80%, above about 90%, or any range between any of the aforesaid amounts; and more preferably from about 10% to about 60% of at least one aprotic polar solvent.

In certain embodiments, the aprotic polar solvent is DMSO and its concentration is in the range between about 30% and about 60%. In an embodiment it is between about 40% to about 50%. In an embodiment, aprotic polar solvent is DMSO and its concentration is about 45%.

In other embodiments, the composition contains more than 60% aprotic polar solvent, and in certain cases, up to about 98% of at least one aprotic polar solvent.

In one or more embodiments where ever a phrase is used to refer to a concentration of above X % or below X % it can also include X % or of above about X % or below about X % it can also include about X %.

General

In one or more embodiments, the aprotic polar solvent is a combination of two or more aprotic solvents. In certain embodiments the main aprotic solvent is DMSO.

In one or more embodiments, the aprotic polar solvent is used in combination with a solid aprotic compound. Non limiting examples of solid aprotic compounds are octyl methyl sulfoxide, nonyl methyl sulfoxide, decyl methyl sulfoxide, undecyl methyl sulfoxide, and dodecyl methyl sulfoxide.

In one or more embodiments, the aprotic polar solvent is used in combination with a sulfoxide derivative which is not aprotic. Non limiting examples of non aprotic sulfoxide compounds having hydroxyl groups are 2-hydroxydecyl methyl sulfoxide, 2-hydroxyundecyl methyl sulfoxide and hydroxydodecyl methyl sulfoxide.

In one or more embodiments, formulations comprising DMSO can produce a quality foam with one or more surfactants without the addition of a polymer and or without the addition of a foam adjuvant. Aprotic solvents are not oil so which surfactants are preferred is not obvious. In one or more embodiments preferred surfactants or surfactant combinations include polyoxyethylene fatty acid ethers, polyoxyethylene fatty acid esters, polysorbates, sucrose esters, glycerides esters, sorbitol esters.

In one or more embodiments, formulations comprising DMSO can unexpectedly produce a quality foam without one or more surfactants. In one or more embodiments good quality waterless foams comprising DMSO can be achieved with a combination of a polymeric agent and a fatty alcohol. In an embodiment the fatty alcohol may be replaced by the fatty acid. In an embodiment a combination of fatty alcohol and fatty acid may be applied together with the polymeric agent.

In one or more embodiments good quality aqueous foams comprising DMSO can be achieved with a combination of a polymeric agent and a fatty alcohol. In one or more embodiments good quality aqueous foams comprising DMSO can be achieved with the addition of a short chain alcohol, such as ethanol, even in high concentrations.

By the term "aqueous" in relation to formulations herein it is intended to indicate and describe a multiplicity of formulations containing some water including formulations comprising low amounts, medium amounts or high amounts of water so as to apply a wide meaning to the term.

Foamable Composition and Foam Properties

The ability to achieve quality foam with substantial concentration of at least one aprotic polar solvent, is surprising, because usually, such solvents are not prone to create a foam. The challenge is not just to achieve a quality foam but also to attain a formulation that will satisfy a plurality of two, three, four, five, six or more of property specifications simultaneously.

1. Uniformity: The composition should be formulated so that it is and can remain uniform without phase separation or precipitation over time. This property is of high importance when the product is intended to be a pharmaceutical product.
2. Flowability: The composition, when placed in an aerosol container and pressurized should be flowable such that it can be expelled through the canister valve. It should preferably also be shakable inside the container. These requirements create a formulation challenge, because low or non-viscous flowable and shakable compositions are prone to undergo phase separation or precipitation.
3. Quality: Upon release from the can, the composition should generate a foam of about good or excellent quality having low density and small bubble size.
4. Stability/Breakability: The fine balance between stability and breakability of the foam coming out of the container is very delicate: on one hand the foam should not be "quick breaking", i.e., it should be at least short term stable upon release from the pressurized container and not break as a result of exposure to skin temperature; and on the other hand, it should be "breakable", i.e., it should spread easily, break down and absorb into the skin or membrane upon application of mild shear force.
5. Skin Feeling: To ensure patient compliance the skin feeling after application should be pleasant, and greasy or waxy residues should be minimalized.
6. Non irritating: The above requirements should be achieved with the awareness that formulation excipients, especially surfactants, can be irritating, and should be used in low concentrations.
7. Delivery: Finally, the composition should also be designed to ensure efficient delivery of a therapeutic agent (other than the aprotic polar solvent) into the target site of treatment.

Based on extensive investigations and trial and error experiments, it has been found that such properties can be achieved for formulations comprising water by incorporating into the composition at least two stabilizing members, and also for formulations that are substantially waterless by incorporating into the composition at least one stabilizing member selected from the group consisting of:
 i. a surface-active agent;
 ii. a foam adjuvant
 iii. a polymeric agent It has further been discovered that such properties can be achieved for waterless formulations by incorporating into the composition at least one stabilizing member, selected from the group, consisting of:
 i. a surface-active agent;
 ii. a foam adjuvant
 iii. a polymeric agent The type, quality, properties and mechanism of foam formation for aprotic formulations cannot be predicted or deduced based on the literature or on existing product experience. The challenge to achieve such foam formulations may be even more pronounced when the aprotic polar solvent composition is waterless or substantially waterless.

As detailed and exemplified below, the aqueous or water containing compositions containing aprotic polar solvents, such as DMSO, conform with the desirable and favorable sensory properties of foam. They further deliver efficacious therapy, as exemplified herein.

As further detailed and exemplified below, even waterless or substantially waterless compositions, containing aprotic polar solvents, such as DMSO, provide favorable sensory properties of foam.

Surface Active Agent

The composition of the present invention contains a surface-active agent. Surface-active agents (also termed "emulsifiers" or "surfactants") include any agent linking oil and water in the composition, in the form of emulsion. A surfactant's hydrophilic/lipophilic balance (HLB) describes the emulsifier's affinity toward water or oil. HLB is defined for non-ionic surfactants. The HLB scale ranges from 1 (totally lipophilic) to 20 (totally hydrophilic), with 10 representing an equal balance of both characteristics. The HLB of a blend of two emulsifiers equals the weight fraction of emulsifier A times its HLB value plus the weight fraction of emulsifier B times its HLB value (weighted average). In many cases a single surfactant may suffice. In other cases a combination of two or more surfactants is desired. Reference to a surfactant in the specification can also apply to a combination of surfactants or a surfactant system. As will be appreciated by a person skilled in the art which surfactant or surfactant system is more appropriate is related to the vehicle and intended purpose. In general terms a combination of surfactants is usually preferable where the vehicle is an emulsion. In an emulsion environment a combination of surfactants can be significant in producing breakable foams of good quality. It has been further discovered that the generally thought considerations for HLB values for selecting a surfactant or surfactant combination are not always binding for emulsions and that good quality foams can be produced with a surfactant or surfactant combination both where the HLB values are in or towards the lipophilic side of the scale and where the HLB values are in or towards the hydrophilic side of the scale. Surfactants also play a role in foam formation where the foamable formulation is a single phase composition.

According to one or more embodiments the composition contains a single surface active agent having an HLB value between about 2 and 9, or more than one surface active agent and the weighted average of their HLB values is between about 2 and about 9. Lower HLB values may in certain embodiments be more applicable, especially in compositions with low water content, or non-aqueous compositions.

According to one or more embodiments the composition contains a single surface active agent having an HLB value between about 7 and 14, or more than one surface active agent and the weighted average of their HLB values is between about 7 and about 14. Mid range HLB values may in certain embodiments be more suitable for oil in water emulsions.

According to one or more other embodiments the composition contains a single surface active agent having an HLB value between about 9 and 20, or more than one surface active agent and the weighted average of their HLB values is between about 9 and about 20.

In a waterless or substantially waterless environment a wide range of HLB values may be suitable; however, surfactants of the low range are sometimes preferred.

Preferably, the composition of the present invention contains a non-ionic surfactant. Nonlimiting examples of possible non-ionic surfactants include:

Polyoxyethylene sorbitan esters (polysorbates), such as Polysorbate 20 (polyoxyethylene (20) sorbitan monolaurate), Polysorbate 40 (polyoxyethylene (20) sorbitan monopalmitate), Polysorbate 60 (polyoxyethylene (20) Sorbitan monostearate) and Polysorbate 80 (polyoxyethylene (20) sorbitan monooleate).

Sorbitan esters, such as Span 20 (Sorbitan monolaurate), Span 40 (Sorbitan monopalmitate), Span 60 (Sorbitan monostearate), Span 65 (Sorbitan tristearate), Span 80 (Sorbitan monooleate).

Polyoxyethylene fatty acid esters, such as, PEG-8 Stearate, PEG-20 Stearate, PEG-40 Stearate, PEG-100 Stearate, PEG-150 Distearate, PEG-8 laurate, PEG-10 laurate, PEG-12 laurate, PEG-20 laurate, PEG-8 oleate, PEG-9 oleate, PEG-10 oleate, PEG-12 oleate, PEG-15 oleate and PEG-20 oleate.

PEG-Fatty Acid Diesters, such as PEG-20 dilaurate, PEG-20 dioleate, PEG-20 distearate, PEG-32 dilaurate and PEG-32 dioleate.

Polyethylene glycol (PEG) ethers of fatty alcohols, e.g., Isoceteth-20, Laureth-4, Laureth-9, Laureth-23, Ceteth-2, Ceteth-10, Ceteth-20, Steareth-2, Steareth-7, Steareth-10, Steareth-20, Steareth-21, Steareth-100, Steareth-200, Oleth-2, Oleth-3, Oleth-5, Oleth-10, Oleth-20, Ceteareth-6, Ceteareth-12, Ceteareth-17, Ceteareth-20, Ceteareth-25, Ceteareth-50, Ceteareth-80, Cetoleth-5, Cetoleth-10, Pareth-12, Pareth-23, C12-13 Pareth-3, C12-13 Pareth-4.

Glycerol esters, such as glyceryl monostearate, glyceryl monolaurate, glyceryl monopalmitate and glyceryl monooleate PEG-fatty Acid Mono- and di-ester Mixtures—several PEG-fatty acid esters are marketed commercially as mixtures or mono- and diesters.

Polyethylene Glycol Glycerol Fatty Acid Esters, such as PEG-7 Glyceryl Cocoate, PEG-7 Glyceryl Cocoate, PEG-20 Almond Glycerides, PEG-12 glyceryl laurate, PEG-20 glyceryl laurate, PEG-30 glyceryl laurate, PEG-40 glyceryl laurate, PEG-20 glyceryl oleate, and PEG-30 glyceryl oleate.

Alcohol-Oil Transesterification Products such as PEG-5 hydrogenated castor oil, PEG-6 almond oil, PEG-6 caprylic/capric glycerides, PEG-6 peanut oil, PEG-6 corn oil, PEG-6 apricot kernel oil, PEG-6 triolein, PEG-7 hydrogenated castor oil, PEG-8 caprylic/capric glycerides, PEG-8 corn oil, PEG-9 hydrogenated castor oil, PEG-20 corn glycerides, PEG-20 almond glycerides, PEG-25 hydrogenated castor oil, PEG-25 trioleate, PEG-35 castor oil, PEG-40 hydrogenated castor oil, PEG-60 corn glycerides, PEG-60 almond oil, PEG-40 palm kernel oil, PEG-50 castor oil, PEG-50 hydrogenated castor oil. Also included as oils in this category of surfactants are oil-soluble vitamins, such as vitamins A, D, E, K, etc. Thus, derivatives of these vitamins, such as tocopheryl PEG-100 succinate, are also suitable surfactants.

Polyglycerized Fatty Acids, such as polyglyceryl oleate, polyglyceryl-2 dioleate, and polyglyceryl-10 trioleate (hydrophobic); and polyglyceryl-10 laurate, polyglyceryl-10 oleate, and polyglyceryl-10 mono, dioleate (hydrophilic). Polyglyceryl polyricinoleates are also preferred hydrophilic and hydrophobic surfactants.

Propylene glycol fatty acid esters, such as propylene glycol monolaurate, propylene glycol ricinoleate, propylene glycol monooleate, propylene glycol dicaprylate/dicaprate and propylene glycol dioctanoate.

Mono- and diglycerides, such as glyceryl monooleate, glyceryl ricinoleate, glyceryl laurate, glyceryl dilaurate, glyceryl dioleate, glyceryl mono/dioleate, glyceryl caprylate/caprate, caprylic acid mono/diglycerides, and mono- and diacetylated monoglycerides.

Sterol and sterol derivatives, such as PEG-24 cholesterol ether.

Sugar esters (mono-, di- and tri-esters of sucrose with fatty acids), such as sucrose monopalmitate and sucrose monolaurate.

Polyethylene glycol alkyl phenols

The following table provides by examples the HLB values of various non-ionic surfactants, sorted by HLB from lowest (hydrophobic) to highest (hydrophilic).

| | |
|---|---|
| Glycol Distearate HLB = 1 | PEG-7 Olivate HLB = 11 |
| Sorbitan Trioleate HLB = 1.8 | Cetearyl Glucoside HLB = 11 |
| Propylene Glycol Isostearate HLB = 2.5 | PEG-8 Oleate HLB = 11.6 |
| | Polyglyceryl-3 Methyglucose |
| Glycol Stearate HLB = 2.9 | Distearate HLB = 12 |
| Sorbitan Sesquioleate HLB = 3.7 | Oleth-10 HLB = 12.4 |
| Glyceryl Stearate HLB = 3.8 | Oleth-10/Polyoxyl 10 Oleyl |
| Lecithin HLB = 4 | Ether NF HLB = 12.4 |
| Sorbitan Oleate HLB = 4.3 | Ceteth-10 HLB = 12.9 |
| Sorbitan Monostearate NF HLB = 4.7 | PEG-8 Laurate HLB = 13 |
| Sorbitan Stearate HLB = 4.7 | Cocamide MEA HLB = 13.5 |
| Sorbitan Isostearate HLB = 4.7 | Polysorbate 60 HLB = 14.9 |
| Steareth-2 HLB = 4.9 | Polysorbate 80 HLB = 15 |
| Oleth-2 HLB = 4.9 | Isosteareth-20 HLB = 15 |
| Glyceryl Laurate HLB = 5.2 | PEG-60 Almond Glycerides |
| Ceteth-2 HLB = 5.3 | HLB = 15 |
| PEG-30 Dipolyhydroxystearate HLB = 5.5 | Polysorbate 80 HLB = 15 |
| | PEG-20 Methyl Glucose |
| Glyceryl Stearate SE HLB = 5.8 | Sesquistearate HLB = 15 |
| PEG-4 Dilaurate HLB = 6 | Ceteareth-20 HLB = 15.2 |
| Methyl Glucose Sesquistearate HLB = 6.6 | Oleth-20 HLB = 15.3 |
| | Steareth-20 HLB = 15.3 |
| Sorbitan Laurate HLB = 8.6 | Steareth-21 HLB = 15.5 |
| PEG-40 Sorbitan Peroleate HLB = 9 | Ceteth-20 HLB = 15.7 |
| Laureth-4 HLB = 9.7 | Isoceteth-20 HLB = 15.7 |
| PEG-7 Glyceryl Cocoate HLB = 10 | Polysorbate 20 HLB = 16.7 |
| PEG-20 Almond Glycerides HLB = 10 | Laureth-23 HLB = 16.9 |
| PEG-25 Hydrogenated Castor Oil HLB = 10.8 | PEG-100 Stearate HLB = 18.8 |
| | Steareth-100 HLB = 18.8 |
| Stearamide MEA HLB = 11 | PEG-80 Sorbitan Laurate |
| Polysorbate 85 HLB = 11 | HLB = 19.1 |

In one or more embodiments of the composition comprises water and a single stabilizing member, which is at least one surface active agent. In such embodiments the at least one surface active agent is non ionic and can comprise a solid (for example ceteth −20) or liquid surfactant (for example Tween 80) with a HLB between about 9 and about 16. As can be seen from the results in Example 8 in which a non ionic surfactant alone with a HLB between about 9-16 provides a better foam quality and stability than a non ionic surfactant alone with a HLB value lower than about 9 or higher than about 16. However, in order to improve stability and collapse time the aqueous formulations comprise a second stabilizing member, which can be an appropriate polymeric agent (such as hydroxypropyl methylcellulose) and or an appropriate foam adjuvant (such as cetostearyl alcohol, stearyl alcohol, stearic acid and isostearic acid) or a polymeric agent, which has surfactant properties such as a poloxamer. In certain embodiments a combination of at least two stabilizing members is a synergistic combination, such as observed in Example 9. Also by providing two or more stabilizing members it can allow a wider range of agents and or a broader range of HLB. In one or more other embodiments the formulation comprises a hydrophobic or lipophilic component and the formulation prior to addition of the propellant is an emulsion. In such embodiments the surface active agent has a role in stabilizing the emulsion and a role in generating a stable breakable foam. Furthermore a system has to be selected such that upon addition of the propellant the emulsion is not destabilized. The emulsion can be an oil in water emulsion or if an appropriate surfactant is used such as the following non limiting examples of glyceryl stearate, sorbitan stearate, polyglyceryl oleate or other surfactants with an HLB value lower than about 9, a water in oil emulsion may be formed.

In one or more embodiments the composition is a waterless composition and a single stabilizing member. The stabilizing member can be at least one polymeric agent, at least one foam adjuvant or at least one surface active agent. In such embodiments the at least one surface active agent is non ionic and can comprise a solid surface active agent, which is a solid ambient temperature. In one preferred embodiment the surfactant generally comprises a linear molecule with a more polar head, for example sorbitan monostearate and or glyceryl monostearate. It has been observed, for example, that when a surfactant with a non linear unsaturated fatty acid chain is used, such as sorbitan monoleate, only a bubbly liquid is achieved (See Example 3). This incidentally is in contrast to the position with an aqueous system where for example Tween 80 has been used successfully although it has an oleate moiety. In another preferred embodiment, in the context of a waterless composition, the surfactant has a low HLB value, being between about 2 and about 9. In certain embodiments, the HLB of the solid surface active agent is between about 2 and about 5. It has been surprisingly discovered that a solid surface active agent, having low HLB provides a foam with better quality and stability than a liquid and/or a high HLB surfactant. It has been further surprisingly discovered that a solid surface active agent, having low HLB evolves a breakable foam of quality, even without any additional foam stabilizing agents (such as a polymer or a foam adjuvant).

In one or more embodiments the surface active agent is a combination of two or more surface active agents. Such a combination may be in certain cases more effective than a single surfactant and provides a more stable emulsion or improved foam quality. For example and by way of non-limiting explanation it has been found that by choosing two surfactants, one hydrophobic and the other hydrophilic the combination can produce a more stable emulsion than a single surfactant. In certain embodiments the combination is a synergistic combination. In one or more embodiments the difference in the HLB of two surfactants is about at least 2, or is about at least 3, or is about at least 4.

In one or more embodiments the surfactant can be, a surfactant system comprising of a surfactant and a co surfactant, a waxy emulsifier, a liquid crystal emulsifier, an emulsifier which is solid or semi solid at room temperature and pressure, or combinations of two or more agents in an appropriate proportion as will be appreciated a person skilled in the art. Where a solid or semi solid emulsifier combination is used it can also comprise a solid or semi solid emulsifier and a liquid emulsifier.

In one or more embodiments the surface-active agent includes at least one non-ionic surfactant. Ionic surfactants are known to be irritants. Therefore, non-ionic surfactants are preferred in applications including sensitive tissue such as found in most mucosal tissues, especially when they are infected or inflamed. We have surprisingly found that non-ionic surfactants alone can provide formulations and foams of good or excellent quality in the carriers and compositions disclosed herein.

Yet, in certain embodiments, the foamable composition includes a mixture of at least one non-ionic surfactant and at least one ionic surfactant, selected from the group of anionic, cationic, zwitterionic, amphoteric and ampholytic surfactants, in a ratio in the range of about 100:1 to 6:1. In one or more embodiments, the non-ionic to ionic surfactant ratio is greater than about 6:1, or greater than about 8:1; or greater than about 14:1, or greater than about 16:1, or greater than about 20:1. In further embodiments, surface active agent comprises a combination of a non-ionic surfactant and an ionic surfactant, at a ratio of between 1:1 and 20:1.

In selecting a suitable surfactant or combination thereof it should be borne in mind that the upper amount of surfactant that can be used may be limited by the shakability of the composition. In general terms, as the amount of non liquid surfactant is increased the shakability of the formulation reduces until a limitation point is reached where the formulation becomes non shakable and unsuitable. Thus in an embodiment any effective amount of surfactant may be used provided the formulation remains shakable. In other certain exceptional embodiments the upper limit may be determined by flowability such as in circumstances where the composition is marginally or apparently non shakable. Thus in an embodiment any effective amount of surfactant may be used provided the formulation remains flowable.

In certain embodiments the amount of surfactant or combination of surfactants is between about 0.05% to about 20%; between about 0.05% to about 15%; or between about 0.05% to about 10%. In a preferred embodiment the concentration of surface active agent is between about 0.2% and about 8%. In a more preferred embodiment the concentration of surface active agent is between about 1% and about 6%. In certain embodiments by comprising a second or a second and a third stabilizing member it is possible to minimize the amount of surfactant used in the formulation, for example such that the surface active agent is between about 0.5% and about 3%.

If the composition as formulated is a substantially non shakable composition it is nevertheless possible as an exception in the scope disclosed herein for the formulation to be flowable to a sufficient degree to be able to flow through an actuator valve and be released and still expand to form a good quality foam. This surprising and unusual exception may be due one or more of a number of factors such as the high viscosity, the softness, the lack of crystals, the pseudoplastic or semi pseudo plastic nature of the composition and the dissolution of the propellant into the formulation.

Foam Adjuvant

In one or more embodiments the foamable vehicle further includes a foam adjuvant. More particularly the foam adjuvant is preferably a fatty acid or a fatty alcohol. Foam adjuvants, as defined herein are also useful in facilitating improved spreadability and absorption of the composition.

In one or more embodiments the foam adjuvant includes fatty alcohols having 15 or more carbons in their carbon chain, such as cetyl alcohol and stearyl alcohol (or mixtures thereof). Other examples of fatty alcohols are arachidyl alcohol (C20), behenyl alcohol (C22), 1-triacontanol (C30), as well as alcohols with longer carbon chains (up to C50).

In one or more embodiments the foam adjuvant includes fatty acids having 16 or more carbons in their carbon chain, such as hexadecanoic acid (C16) stearic acid (C18), arachidic acid (C20), behenic acid (C22), octacosanoic acid (C28), as well as fatty acids with longer carbon chains (up to C50), or mixtures thereof. As for fatty alcohols, the amount of fatty acids required to support the foam system is inversely related to the length of its carbon chain.

In one or more embodiments, a combination of a fatty acid and a fatty alcohol is employed.

Optionally, the carbon atom chain of the fatty alcohol or the fatty acid may have at least one double bond. A further class of foam adjuvant includes a branched fatty alcohol or fatty acid. The carbon chain of the fatty acid or fatty alcohol also can be substituted with a hydroxyl group, such as 12-hydroxy stearic acid.

An important property of the fatty alcohols and fatty acids used in context of the composition disclosed herein is related to their therapeutic properties per se. Long chain saturated and mono unsaturated fatty alcohols, e.g., stearyl alcohol, erucyl alcohol, arachidyl alcohol and behenyl alcohol (docosanol) have been reported to possess antiviral, antiinfective, antiproliferative and anti-inflammatory properties (see, U.S. Pat. No. 4,874,794). Longer chain fatty alcohols, e.g., tetracosanol, hexacosanol, heptacosanol, octacosanol, triacontanol, etc., are also known for their metabolism modifying properties and tissue energizing properties. Long chain fatty acids have also been reported to possess anti-infective characteristics.

In one or more embodiments, a combination of a foam adjuvant and a polymeric agent is employed. In certain embodiments the combination is synergistic, for example as observed in Example 5 Part B, where stearyl alcohol and hydoxypropyl methylcellulose were noted to have a synergistic effect.

In one or more embodiments, a combination of a foam adjuvant and a surface active agent is employed.

In one or more embodiments, a combination of a foam adjuvant and a polymeric agent is employed.

In one or more embodiments, a combination of a foam adjuvant, a polymeric agent and a surface active agent is employed.

Polymeric Agent

In one or more embodiments, the composition disclosed herein contains a polymeric agent selected from the group consisting of a bioadhesive agent, a gelling agent, a film forming agent and a phase change agent. A polymeric agent enhances the creation of foam having fine bubble structure, which does not readily collapse upon release from the pressurized aerosol can. The polymeric agent serves to stabilize the foam composition and to control drug residence in the target organ. In certain embodiments the polymer can have surfactant like properties and contribute to the stabilization of emulsion formulations, such as poloxamer or pemulen.

Exemplary polymeric agents include, in a non-limiting manner, naturally-occurring polymeric materials, such as locust bean gum, sodium alginate, sodium caseinate, egg albumin, gelatin agar, carrageenin gum, sodium alginate, xanthan gum, quince seed extract, tragacanth gum, guar gum, cationic guars, hydroxypropyl guar gum, starch, amine-bearing polymers such as chitosan; acidic polymers obtainable from natural sources, such as alginic acid and hyaluronic acid; chemically modified starches and the like, carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like.

Additional exemplary polymeric agents include semisynthetic polymeric materials such as cellulose ethers, such as methylcellulose, hydroxypropyl cellulose, hydroxypropyl methylcellulose, hydroxyethyl cellulose, hydroxy propylmethyl cellulose, methylhydroxyethylcellulose, methylhydroxypropylcellulose, hydroxyethylcarboxymethylcellulose, carboxymethyl cellulose, carboxymethylcellulose carboxymethylhydroxyethylcellulose, and cationic celluloses, carbomer (homopolymer of acrylic acid is crosslinked with an allyl ether pentaerythritol, an allyl ether of sucrose, or an allyl ether of propylene, such as Carbopol® 934, Carbopol® 940, Carbopo® 941, Carbopol® 980 and Carbopol® 981. Poloxamers (synthetic block copolymer of ethylene oxide and propylene) such as Poloxamer 124, Poloxamer 188, Poloxamer 237, Poloxamer 338 and Poloxamer 407. Other useful Poloxamers are: 181, 182, 183, 184, 185, 212, 215, 217, 231, 234, 235, 238, 331, 333, 334, 335, 401, 402, and 403. Polyethylene glycol, having molecular weight of 1000 or more (e.g., PEG 1,000, PEG 4,000, PEG 6,000 and PEG 10,000) also have gelling capacity and they are also considered polymeric agents.

In one or more embodiments the polymer is hydoxypropyl methyl cellulose, for example where the formulation is waterless and a single stabilizing member is utilized, the polymeric agent comprises hydroxypropyl methyl cellulose.

Mixtures of the above polymeric agents are contemplated.

In one or more embodiments the polymer is used in combination with another stabilizing member, which can be a surfactant and or a foam adjuvant.

The concentration of the polymeric agent should be selected so that the composition, after filling into aerosol canisters and pressurized with propellant, is flowable, and can be shaken in the canister. In one or more embodiments, the concentration of the polymeric agent is selected such that the viscosity of the composition, prior to filling of the composition into aerosol canisters, is less than about 30,000 CP, and more preferably, less than about 15,000 CP. In one or more embodiments, the viscosity of the composition, prior to filling of the composition into aerosol canisters, is less than about 10,000 CP, or less than about 5,000 CP, or less than about 3,000 CP.

Combination of a Foam Adjuvant and a Polymeric Agent

Interestingly, when a foam adjuvant (e.g., stearyl alcohol) alone or a polymeric agent (e.g., hydroxypropyl methylcellulose) alone is used with DMSO, a foam of good quality is obtained, but it quickly collapses upon exposure to 36° C. (collapse time 10 and 30 sec respectively), as shown in formulations D21 and D07. However, surprisingly, when these two components are combined with DMSO, they act synergistically to produce a good quality foam with a collapse time of 120 seconds as shown in formulation D22 (See Example 5 Part B).

Optional Organic Carriers

Optionally, the foamable composition further includes at least one organic carrier selected from the group consisting of a hydrophobic organic carrier, a petrolatum, an organic protic polar solvent, and mixtures thereof, at a concentration of about 2% to about 50% by weight.

Hydrophobic Solvent/Emollient

One or more hydrophobic solvents are optionally included in the composition, in order to add to the sensory properties of the composition and/or in order to impart skin conditioning properties. In an embodiment, the hydrophobic solvent is an emollient, i.e., a substance that softens and soothes the skin. Emollients are used to correct dryness and scaling of the skin. The hydrophobic solvent and/or the emollient can be selected from the group consisting of mineral oil, alkyl esters of fatty acids such as isopropyl palmitate, isopropyl isostearate, diisopropyl adipate, diisopropyl dimerate, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, maleated soybean oil, unsaturated or polyunsaturated oils, such as olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil, evening primrose oils; essential oils; and silicone oils, such as dimethicone, cyclomethicone, polyalkyl siloxane, polyaryl siloxane, polyalkylaryl siloxane, a polyether siloxane copolymer and a poly(dimethylsiloxane)-(diphenyl-siloxane) copolymer. In certain embodiments the carrier is a petrolatum.

While the aprotic polar solvent and water are generally miscible, when a hydrophobic carrier is included to the composition, it is necessary to create an emulsion between the water/aprotic polar solvent mixture and the hydrophobic carrier. Even when the composition is waterless, the hydrophobic carrier is typically insoluble in the aprotic solvent, and therefore it is necessary to create an emulsion between the aprotic polar solvent and the hydrophobic carrier.

Protic Polar Solvent

A "protic polar solvent" is an organic solvent that has a hydrogen atom bound to an oxygen as in a hydroxyl group or a nitrogen as in an amine group. They are typically soluble in both water and oil.

In one or more embodiments, the formulation can comprise a protic polar solvent.

In one or more embodiments, the protic polar solvent is a polyol. Polyols are organic substances that contain at least two hydroxy groups in their molecular structure.

In one or more embodiments, the protic polar solvent contains an diol (a compound that contains two hydroxy groups in its molecular structure), such as propylene glycol (e.g., 1,2-propylene glycol and 1,3-propylene glycol), butanediol (e.g., 1,4-butaneediol), butanediol (e.g., 1,3-butaneediol and 1,4-butenediol), butynediol, pentanediol (e.g., 1,5-pentanediol), hexanediol (e.g., 1,6-hexanediol), octanediol (e.g., 1,8-octanediol), neopentyl glycol, 2-methyl-1,3-propanediol, diethylene glycol, triethylene glycol, tetraethylene glycol, dipropylene glycol and dibutylene glycol.

In one or more embodiments, the polar solvent contains a triol (a compound that contains three hydroxy groups in its molecular structure), such as glycerin and 1,2,6-Hexanetriol. Additional examples of protic polar solvents include polyols, such as glycerol (glycerin), propylene glycol, hexylene glycol, diethylene glycol, propylene glycol n-alkanols, terpenes, di-terpenes, tri-terpenes, terpen-ols, limonene, terpene-ol, 1-menthol, dioxolane, ethylene glycol, other glycols, alkanols, such as dialkylamino acetates, and admixtures thereof, dimethyl isosorbide, ethyl proxitol, dimethylacetamide (DMAc) and alpha hydroxy acids, such as lactic acid and glycolic acid.

According to still other embodiments, the polar solvent is a polyethylene glycol (PEG) or PEG derivative that is liquid at ambient temperature, including PEG200 (MW (molecular weight) about 190-210 kD), PEG300 (MW about 285-315 kD), PEG400 (MW about 380-420 kD), PEG600 (MW about 570-630 kD) and higher MW PEGs such as PEG 4000, PEG 6000 and PEG 10000 and mixtures thereof.

Lower molecular weight alcohols can sometimes be more potent as a solvent, for example by extracting lipids from the skin layers more effectively, which characteristic can adversely affect the skin structure and cause dryness and irritation. So where a lower molecular weight alcohol is used in a formulation other ingredients are ideally selected to ameliorate or prevent such side effects.

Many polar solvents, for example propylene glycol and glycerin, possess the beneficial property of a heumectant.

In one or more embodiments, the polar solvent is a humectant.

Additional Components

In an embodiment, a composition disclosed herein includes one or more additional components. Such additional components include but are not limited to anti oxidants anti perspirants, anti-static agents, buffering agents, bulking agents, chelating agents, cleansers, colorants, conditioners, deodorants, diluents, dyes, emollients, fragrances, hair conditioners, herbal extracts, humectants, keratolytic agents, pearlescent aids, perfuming agents, permeation enhancers, pH-adjusting agents, preservatives, protectants, skin penetration enhancers, softeners, solubilizers, sunscreens, sun blocking agents, sunless tanning agents, viscosity modifiers, flavanoids and vitamins. As is known to one skilled in the art, in some instances a specific additional component may have more than one activity, function or effect.

Propellants

The composition of the present invention requires the addition of a propellant in order to generate a foam. In one or more embodiments the propellant makes up between about 3% and about 45% or between about 3% and about 35% of the foamable composition, preferably between about 5% and about 25% of the composition. In preparing the formulations the ingredients other than propellant are combined to 100% and the propellant is added thereafter so that the ratio of formulation to propellant can range from 100:3 to 100:45 or from 100:3 to 100:35 or preferably 100:5 to 100:25. In the case of bag in can where the propellant is separate from the composition any amount can be used that is sufficient to drive the contents of the bag out of the canister. In certain embodiments the propellant in the bag can be the same as and in certain other embodiments be different from the propellant in the composition.

Suitable propellants include volatile hydrocarbons such as butane, propane, isobutene or mixtures thereof. In one or more embodiments a hydrocarbon mixture AP-70 is used. Hydrofluorocarbon (HFC) propellants are also suitable as propellants in the context disclosed herein. Exemplary HFC propellants include 1,1,1,2 tetrafluorethane (Dymel 134), and 1,1,1,2,3,3,3 heptafluoropropane (Dymel 227). Dimethyl ether is also useful. In one or more embodiments use of compressed gases (e.g., air, carbon dioxide, nitrous oxide, and nitrogen) is also possible. Chloro fluorocarbon propellants on the other hand are no longer considered suitable for use in cosmetic, pharmaceutical and other formulations due to inter alia the potential environmental damage that they can do.

In one or more embodiments a combination of at least two propellants, selected from HFC, hydrocarbon propellants, dimethyl ether and compressed gases is contemplated.

In one or more embodiments the propellant can also be used to expel formulation using a bag in can system or a can in can system as will be appreciated by someone skilled in the art. In certain embodiments the part of the propellant system is in the formulation and part separate from the formulation. In this way it is possible to reduce the amount of surfactant in the formulation but still provide good expulsion from the canister, where the foamable formulation is expelled quickly but without jetting or noise.

Alcohol Free

According to one or more embodiments, the foamable composition is substantially alcohol-free, i.e., free of short chain alcohols. Short chain alcohols, having up to 5 carbon atoms in their carbon chain skeleton and one hydroxyl group, such as ethanol, propanol, isopropanol, butanol, iso-butanol, t-butanol and pentanol, are considered less desirable solvents or polar solvents due to their skin-irritating effect. Thus, the composition is substantially alcohol-free and includes less than about 5% final concentration of lower alcohols, preferably less than about 2%, more preferably less than about 1%.

Alcoholic

According to one or more certain other embodiments, the foamable composition includes a short chain alcohol. In a preferred embodiment the short chain alcohol is ethanol. In one embodiment the composition is waterless. In another embodiment it is aqueous or water containing and in a further embodiment it is substantially non-aqueous. In various embodiments the amount of short chain alcohol is about or above about 5%, about or above about 10%; about or above about 15% about or above about 20%. In one or more embodiments the range of short chain alcohol is between about 5% to about 25%. In certain embodiments when short chain alcohol is present the formulation is breakable and not thermolabile or substantially not thermolabile. By substantially not thermolabile is meant that the foam upon expulsion onto a warm body surface at about 35-37° C. does not collapse rapidly within about 30 seconds. In one or more alternative embodiments the formulation is thermolabile.

In one or more alternative embodiments the formulation comprises high amounts of short chain alcohol. In certain embodiments the amount of short chain alcohol is about or above about 25%, is about or above about 30%, is about or above about 35%, is about or above about 40%; is about or above about 45%, is about or above about 50%; is about or above about 55% or is about or above about 60%.

In one or more embodiments there is provided a composition comprising an aprotic polar solvent and a protic polar solvent, in which the protic polar solvent can be a short chain alcohol. Such a combination may conceivably contribute to directed skin delivery of active agents.

Aprotic-Aqueous Formulations

In certain cases, the active agent is soluble in the presence of water, and therefore, in such cases the presence of water in the composition can be desirable. In certain preferred embodiments, the composition comprises only a small amount of water. In other embodiments water is a substantial component. In one or more embodiments the range of water can be from about 0.1% to about 5%, or from about 5% to about 15%, or from about 15% to about 25%, or from about 25% to about 35%, or from about 35% to about 45%, or from about 45% to about 55%, or from about 55% to about 65%, or from about 55% to about 65%, or from about 65% to about 75%, or from about 75% to about 85% or from about 5% to about 85%, or from about 10% to about 75%. In one or more embodiments the formulation can be aprotic-hydroalcoholic.

Waterless Formulations

In certain cases, the active agent degrades in the presence of water, and therefore, in such cases the presence of water in the composition is not desirable. Thus, in certain preferred embodiments, the composition is substantially non-aqueous. The term "substantially non-aqueous" or "substantially waterless" is intended to indicate that the composition has water content below about 5%, preferably below about 2%, such as below about 1.5%. In certain other preferred embodiments the composition is non aqueous or waterless.

By non aqueous or waterless is meant that the composition contains no or substantially no, free or unassociated or absorbed water. It will be understood by a person of the art that the waterless solvents and substances miscible with them disclosed herein can be hydrophilic and can contain water in an associated or entrapped or absorbed form and may absorb water from the atmosphere and the ability to do so is its hygroscopic water capacity. It is intended that essentially non-aqueous formulations are included within its scope such that the formulations may have present a small amount of water. In some embodiments the composition ingredients are pretreated to reduce, remove or eliminate any residual or associated or absorbed water.

Modulating Agent

In one or more embodiments the formulation includes a modulating agent, The term modulating agent is used to describe an agent which can improve the stability of or stabilize a foamable carrier or composition and or an active agent by modulating the effect of a substance or residue present in the carrier or composition.

In one or more embodiments the substance or residue may for example be acidic, basic or a buffer system and potentially alter an artificial pH in a waterless or substantially non-aqueous environment or it may be one or more metal ions which may act as a potential catalyst in a waterless or substantially non aqueous environment. In various certain embodiments it may be an ionization agent or an anti oxidization agent or a flavanoid or mixtures thereof that are effective in a waterless or substantially non aqueous environment. The modulating agent may in one or more embodiments act to modulate the ionic or polar characteristics and any acid-base balance of a waterless or substantially non-aqueous carrier, composition, foamable carrier or foamable composition or resultant foam disclosed herein.

In one or more other embodiments the modulating agent is used to describe an agent which can affect pH in an aqueous solution. The agent can be any of the known buffering systems used in pharmaceutical or cosmetic formulations as would be appreciated by a man of the art. It can also be an organic acid, a carboxylic acid, a fatty acid an amino acid, an aromatic acid, an alpha or beta hydroxyl acid an organic base or a nitrogen containing compound.

In certain embodiments the substance or residue may be one or more metal ions which may act as a potential catalyst in a aqueous environment. In various certain embodiments it may be an ionization agent or an anti oxidization agent or a flavanoid or mixtures thereof that are effective in an aqueous environment. The modulating agent may in one or more embodiments act to modulate the ionic or polar characteristics and any acid-base balance of an aqueous carrier, composition, foamable carrier or foamable composition or resultant foam disclosed herein.

In certain embodiments the formulation is an emulsion. The emulsion may be formed prior to the addition of propellant or upon the introduction of propellant. The emulsion may be a waterless emulsion or it may be an aqueous emulsion (oil in water or oil in water). In various certain embodiments the substance or residue may for example be acidic or basic and potentially alter pH in an emulsion environment or it may be one or more metal ions which may act as a potential catalyst in an emulsion environment. In various certain embodiments it may be an ionization agent or an anti oxidization agent or a flavanoid or mixtures thereof that are effective in an emulsion environment. The modulating agent may in one or more embodiments act to modulate the ionic or polar characteristics and any acid-base balance of an emulsion carrier, composition, foamable carrier or foamable composition or resultant foam disclosed herein.

In one or more further embodiments the modulating agent is a chelating or sequestering or complexing agent that is sufficiently soluble or functional in the solvent to enable it to "mop up" or "lock" metal ions. In one or more embodiments a preferred non limiting example is EDTA.

In other embodiments the modulating agent is a buffer, as defined by Van Slyke [Van Slyke, J. Biol. Chem. 52, 525 (1922)], as "a substance which by its presence in solution increases the amount of acid or alkali that must be added to cause unit change in pH."

Modulating agents may be added to the compositions of the subject invention, preferably from about 0.1% to about 10%, more preferably from about 1% to about 5%, of the composition. Where the active agent itself is the modulating agent alone or in combination with another modulating agent it will be added at an effective dose which may be outside these ranges. For example azelaic acid may be at about 15% of the composition.

It is important to maintain skin surface pH in order to prevent susceptibility to bacterial skin infections or skin damage and disease. Thus, adding a modulating agent, which contributes to the stabilization of skin pH at the desirable level, is advantageous.

In the same fashion, adding an acidic modulating agent to a foamable composition, which is intended for vaginal application is advantageous, since better protection against vaginal infection is attained with pH lower than about 4.5.

Non-limiting examples of antioxidants/radical scavengers are ascorbic acid and derivatives, tocopherol or derivatives thereof (succinate, or sorbate or acetate or other esters), propyl galate, butylated hydroxy toluene and butyl hydroxy anisol. Non-limiting examples of positive ionization agents are benzyl conium chloride, and cetyl pyridium chloride. Non-limiting examples of negative ionization agents are sodium lauryl sulfate, sodium lauryl lactylate and phospholipids.

A non-limiting list of flavanoid compounds is: benzquercin, diosmin, ethoxazorutoside, flavodate, sodium hesperidin, leucocianido, monoxerutin, oxerutin, quercetin, rutoside, rosmarinic acid.

In one or more embodiments the modulating agent is mixture or combination of two or more modulating agents.

Composition and Foam Physical Characteristics and Advantages

A pharmaceutical or cosmetic composition manufactured using the foamable carrier is very easy to use. When applied onto the afflicted body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

In one or more embodiments the foamable composition has an acceptable shelf-life of at least six months or at least one year, or preferably, at least two years at ambient temperature.

The foamable compositions according to the present invention are stable chemically and physically. For example as seen in Example 14 following accelerated stability studies, the foam met the specified stability and assay criteria. The high quality foams disclosed herein can demonstrate desirable texture; can form fine bubble structures that do not break immediately upon contact with a surface, and can spread easily on the treated area and can absorb quickly.

The composition should also preferably be free flowing, to allow it to flow through the aperture of the container, e.g., and aerosol container, and create an acceptable foam.

Foam Quality

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administrable foams are typically of quality grade E or G, when released from the aerosol container. Smaller bubbles are indicative of more stable foam, which does not collapse spontaneously immediately upon discharge from the container. The finer foam structure looks and feels smoother, thus increasing its usability and appeal.

Breakability

A further aspect of the foam is breakability. The balance between stability and breakability of the foam coming out of the container is very delicate: on one hand the foam should not be "quick breaking", i.e., it should be stable upon release from the pressurized container and not break as a result of exposure to skin temperature; and on the other hand, it should be "breakable", i.e., it should spread easily, break down and absorb into the skin or membrane upon application of mild shear force. The foam is thermally stable, yet breaks under shear force. Shear-force breakability of the foam is clearly advantageous over thermally induced breakability. Thermally sensitive foams immediately or quickly collapse upon exposure to skin temperature and, therefore, cannot be usefully applied on the hand and afterwards delivered to the afflicted area since transfer would have to be effected immediately.

Breakable foam is a specialized low density type of foam that is stable on release at least in the short time span of about minutes, but can break readily upon the application of shear force such as gentle rubbing to spread easily over a target surface. Unlike other types of foams, breakable foam is not thermolabile, nor does it display late or long-delayed expansion over minutes.

Foam Density

Another property of the foam is density (specific gravity), as measured upon release from the aerosol can. Typically, foams have specific gravity of about 0.20 g/mL or less, such as less than about 0.20 g/mL; or less than about 0.12 g/mL; or less than about 0.10 g/mL; or less than about 0.08 g/mL, depending on their composition and on the propellant concentration.

Shakability

'Shakability' means that the composition contains some or sufficient flow to allow the composition to be mixed or remixed on shaking. That is, it has fluid or semi fluid properties. Shakability is described further in the section on Tests.

Collapse Time

The collapse time of foam represents its tendency to be temperature-sensitive and its ability to be at least short term stable so as to allow a user sufficient time to comfortably handle and apply the foam to a target area without being rushed and or concerned that it may rapidly collapse, liquefy and or disappear. Collapse time is examined by dispensing a given quantity of foam and photographing sequentially its appearance with time during incubation at 36° C. Thus, it is useful for selecting foam products, which are "breakable" but not "quick breaking", which maintain structural stability at skin temperature for at least a reasonable period of time. In one or more embodiments it can be about more than a minute, about more than two minutes, about more than 3 minutes, about more than 4 minutes, about more than 5 minutes or longer. In one or more limited embodiments it can be shorter than one minute, for example about more than 50 seconds, about more than 40 seconds and occasionally about more than 30 seconds. In a preferred embodiment it can be more than about one minute and in a more preferred embodiment it can be more than about 3 minutes. Collapse time can also provide an indication of the rate of drainage in the foam formulation of the fluid around the bubbles under the influence of gravity. Short collapse times indicate fast or rapid drainage, whilst long collapse times indicate slow drainage.

Pharmaceutical Composition

The foamable composition is an ideal vehicle for active pharmaceutical ingredients and active cosmetic ingredients. In the context active pharmaceutical ingredients and active cosmetic ingredients are collectively termed "active agent" or "active agents". In one or more embodiments the composition comprises a therapeutically effective concentration of at least one active agent. In one or more embodiments the composition comprises at least two therapeutic agents. In certain embodiments the aprotic formulation facilitates the combination of active agents otherwise unstable in water, which for example are unstable at different pH's.

Suitable active agents include but are not limited to an active herbal extract, an acaricides, an age spot and keratose removing agent, an allergen, an alpha hydroxyl acid, an analgesic agent, an antiacne agent, an antiallergic agent, an antiaging agent, an antibacterial agent, an antibiotic, an antiburn agent, an anticancer agent, an antidandruff agent, an antidepressant, an antidermatitis agent, an antiedemic anent, an antifungal agent, an antihistamine, an antihelminth agent, an antihyperkeratolyte agent, an anti-infective agent, an antiinflammatory agent, an antiirritant, an antilipemic agent, an antimicrobial agent, an antimycotic agent, an antioxidant, an antiparasitic agent, an antiproliferative agent, an antipruritic agent, an antpsoriatic agent, an antirosacea agent, an antiseborrheic agent, an antiseptic agent, an antiswelling agent, an antiviral agent, an anti-wart agent, an anti-wrinkle agent, an antiyeast agents, an astringent, a beta-hydroxy acid, benzoyl peroxide, a topical cardiovascular agent, a chemotherapeutic agent, a corticosteroid, an immunogenic substance, a dicarboxylic acid, a disinfectant, a fungicide, a hair growth regulator, a haptene, a hormone, a hydroxy acid, an immunosuppressant, an immunoregulating agent, an immunomodulator, an insecticide, an insect repellent, a keratolytic agent, a lactam, a local anesthetic agent, a lubricating agent, a masking agent, a metals, a metal oxide, a mitocide, a neuropeptide, a non-steroidal anti-inflammatory agent, an oxidizing agent, a pediculicide, a peptide, a protein, a photodynamic therapy agent, a radical scavenger, a refatting agent, a retinoid, a sanative, a scabicide, a self tanning agent, a skin protective agent, a skin whitening agent, a steroid, a steroid hormone, a vasoconstrictor, a vasodilator, a vitamin, a vitamin A, a vitamin A derivative, a vitamin B, a vitamin B derivative, a vitamin C, a vitamin C derivative, a vitamin D, a vitamin D derivative, a vitamin D analog, a vitamin F, a vitamin F derivative, a vitamin K, a vitamin K derivative, a wound healing agent and a wart remover. As is known to one skilled in the art, in some instances a specific active agent may have more than one activity, function or effect.

Encapsulation of an Active Agent

In one or more embodiments, the active agent is encapsulated in particles, microparticles, nanoparticles, microcapsules, microsphres, nanocapsules, nanospheres, liposomes, niosomes, polymer matrix, silica-gel, graphite, nanocrystals or microsponges. Such particles can have various functions, such as (1) protection of the drug from degradation; (2) modification of the drug release rate from the composition; (3) control of skin penetration profile; and (4) mitigation of adverse effects, due to the controlled release of the active agent from the encapsulation particles.

Solubility of an Active Agent

In an embodiment, the active agent is not fully soluble in water or, is not fully soluble in the presence of a hydrophobic solvent in the formulation, or is not fully soluble in the oil phase of the emulsion. In one or more embodiments the active agent is soluble in the composition or a phase thereof. In one or more embodiments the active agent is insoluble in water and wherein the active agent is solubilized in the the composition. In an embodiment, the aprotic polar solvent is present in the composition in an amount sufficient to solubilize the active agent in the composition. In one or more embodiments, aprotic polar solvent acts to improve the solubility of an active agent. In certain preferred embodiments, the active agent to be solubilized is selected from the group consisting of a non-steroidal anti-inflammatory agent, a local anesthetic agent, a steroid, an immunomodulators, a keratolytically active agent, an anti-acne agent, an antirosacea agent, an antiinfective agent and an anti-psoriasis agent. In a preferred embodiment the active agent to be solubilized is diclofenac. In one or more embodiments a protic solvent acts to improve solubility of an active agent. In one or more embodiments the delivery of the active agent is improved by the aprotic solvent and or protic solvent.

In one or more embodiments the active agent is intended for transdermal delivery. In certain embodiments the aprotic polar solvent in included in the composition in a concentration which is sufficient to increase the rate of absorption of such active agent through organic tissues including skin and nails.

Exemplary Groups of Active Agents

NSAID

In an embodiment, the active agent is a non-steroidal anti-inflammatory agent. In the context a nonsteroidal anti-inflammatory agent (also termed herein "NSAID") is a pharmaceutically active compound, other than a corticosteroid, which affects the immune system in a fashion that results in a reduction, inhibition, prevention, amelioration or prevention of an inflammatory process and/or the symptoms of inflammation and or the production pro-inflammatory cytokines and other pro-inflammatory mediators, thereby treating or preventing a disease that involves inflammation.

In one or more embodiments, the NSAID is an inhibitor of the cyclooxygenase (COX) enzyme. Two forms of cyclooxygenase are known today: the constitutive cyclooxygenase (COX-1); and the inducible cyclooxygenase (COX-2), which is pro-inflammatory. Thus, in one or more embodiments, the NSAID is selected from the group consisting of a COX-1 inhibitor, a COX-2 inhibitor or a non-selective NSAID, which simultaneously inhibits both COX-1 and COX-2.

In one or more embodiments, the NSAID is salicylic acid a salicylic acid derivatives. Exemplary salicylic acid derivative include, in a non limiting fashion, aspirin, sodium salicylate, choline magnesium trislicylate, salsalate, diflunisal, salicylsalicylic acid, sulfasalazine, olsalazine, esters of salicylic acid with a carboxylic acid, esters of salicylic acid with a dicarboxylic acid, esters of salicylic acid with a fatty acid, esters of salicylic acid with a hydroxyl fatty acid, esters of salicylic acid with an essential fatty acid, esters of salicylic acid with a polycarboxylic acid, and any compound wherein salicylic acid is linked to an organic moiety through a covalent bond.

In one or more embodiments, the NSAID is para-aminophenol (e.g., acetaminophen) and salts and derivatives thereof.

In one or more embodiments, the NSAID is an indole or an indole-acetic acid derivative (e.g., indomethacin, sulindac, etodolac) and salts and derivatives thereof.

In one or more embodiments, the NSAID is an aryl acetic acids (e.g., tolmetin, diclofenac, ketorolac) and salts and derivatives thereof.

In one or more embodiments, the NSAID is an arylpropionic acid and salts and derivatives thereof. Exemplary arylpropionic acid derivative include, in a non limiting fashion, are ibuprofen, naproxen, flubiprofen, ketoprofen, fenoprofen, oxaprozin.

In one or more embodiments, the NSAID is anthranilic acids or an anthranilic acid derivative, also termed "fenamates" (e.g., mefenamic acid, meclofenamic acid) and salts and derivatives thereof.

In one or more embodiments, the NSAID is selected from the group of enolic acids, enolic acid salts, enolic acid esters, amides, anhydrides and salts and derivatives thereof. Non-limiting examples of enolic acid derivatives include oxicams (piroxicam, tenoxicam) and pyrazolidinediones (phenylbutazone, oxyphenthratrazone)

Yet, in additional embodiments, the NSAID is an alkanone (e.g., nabumetone).

Selective COX-2 Inhibitors include, in an exemplary manner diaryl-substituted furanones (e.g., Rofecoxib); diaryl-substituted pyrazoles (e.g., Celecoxib); indole acetic acids (e.g., Etodolac); and sulfonanilides (e.g., Nimesulide) and salts and derivatives thereof.

In an embodiment, the aprotic polar solvent is present in the composition in an amount sufficient to solubilize the NSAID, as exemplified herein by the solubilization of diclofenac.

Local Anesthetic Agents

In an embodiment, the active agent is a local anesthetic agent. Without limiting the scope of the invention, the anesthetic agent can be selected from the group consisting of benzocaine, lidocaine, bupivacaine, chlorprocaine, dibucaine, etidocaine, mepivacaine, tetracaine, dyclonine, hexylcaine, procaine, cocaine, ketamine, pramoxine, phenol, any pharmaceutically acceptable salts thereof and mixtures of such anesthetic agents. Any mixture of synergistically beneficial anesthetic agents is contemplated. In an embodiment, the aprotic polar solvent is present in the composition in an amount sufficient to solubilize the anesthetic agent.

Steroids

In an embodiment, the active agent is a steroid. In certain embodiments the steroid is a corticosteroid, including but not limited to, bydrocortisone, hydroxyltriamcinolone, alpha-methyl dexamethasone, dexamethasone-phosphate, beclomethsone dipropionate, clobetasol valemate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortmate, mepreddisone, paramethasone, prednisolone, prednisone, beclomethasone dipropionate, triamcinolone, as well as analogs, derivatives, salts, ions and complexes thereof.

In certain embodiments, the steroid is a hormone or a vitamin, as exemplified by pregnane, cholestane, ergostane, aldosterone, androsterone, calcidiol, calciol, calcitriol, calcipotriol, clomegestone, cholesterol, corticosterone, cortisol, cortisone, dihydrotestosterone, ergosterol, estradiol, estriol, estrone, ethinylestradiol, fusidic acid, lanosterol, prednisolone, prednisone, progesterone, spironolactone, timobesone and testosterone, as well as analogs, derivatives, salts, ions and complexes thereof.

In an embodiment, the aprotic polar solvent is present in the composition in an amount sufficient to solubilize the steroid.

Keratolytically Active Agents

A keratolytic agent may be included as an active agent of a foamable composition. The term "keratolytically active agent" as used herein includes a compound that loosens and removes the stratum corneum of the skin, or alters the structure of the keratin layers of skin. Keratolytically active agents are used in the treatment of dermatological disorders that involve dry skin, hyperkeratinization (such as psoriasis), skin itching (such as xerosis), acne and rosacea.

Suitable keratolytically active agents include phenol and substituted phenolic compounds. Such compounds are known to dissolve and loosen the intracellular matrix of the hyperkeratinized tissue. As such, they are used in the treatment of dermatological disorders. Dihydroxybenzene and derivatives thereof have been recognized as potent keratolytic agents. Resorcinol (m-dihydroxybenzene) and derivatives thereof are used in anti-acne preparations. In addition to hydroquinone (p-dihydroxybenzene) having anti-pigmentation properties, hydroquinone is also known to be keratolytic. These compounds also exhibit antiseptic properties. Cresols also possess bactericidal and keratolytic properties.

Vitamin A and vitamin A derivatives, also termed herein "retinoids", such as retinoic acid, isoretinoic acid, retinol and retinal are another class of keratolytically active agents.

Another group of keratolytically active agents include alpha-hydroxy acids, such as lactic acid and glycolic acid and their respective salts and derivatives; and beta-hydroxy acids, such as salicylic acid (o-hydroxybenzoic acid) and salicylic acid salts and pharmaceutically acceptable derivatives.

Another class of keratolytically active agents includes urea and urea derivatives.

Immunomodulators

In an embodiment, the active agent is an immunomodulator. Immunomodulators are chemically or biologically-derived agents that modify the immune response or the functioning of the immune system. Immunomodulators suitable for use according to the present invention include, among other options, cyclic peptides, such as cyclosporine, tacrolimus, tresperimus, pimecrolimus, sirolimus, verolimus, laflunimus, laquinimod and imiquimod, as well as analogs, derivatives, salts, ions and complexes thereof. Such compounds, delivered in the foam, are especially advantageous in skin disorders such as psoriasis, eczema and atopic dermatitis, where the large skin areas are to be treated. In an embodiment, the aprotic polar solvent is present in the composition in an amount sufficient to solubilize the immunomodulator.

Retinoids

In an embodiment, the active agent is a retinoid. Retinoids suitable for use according to the present invention include, among other options, retinol, retinal, retinoic acid, isotretinoin, tazarotene, adapalene, 13-cis-retinoic acid, acitretin all-trans beta carotene, alpha carotene, lycopene, 9-cis-beta-carotene, lutein and zeaxanthin, as well as analogs, derivatives, salts, ions and complexes thereof.

Anti-Acne and Anti-Rosacea Active Agents

In an embodiment, the active agent is an anti-acne or an anti-rosacea agent. The anti-acne agent can be selected from the group consisting of resorcinol, sulfur, salicylic acid and salicylates, alpha-hydroxy acids, nonsteroidal anti-inflammatory agents, benzoyl peroxide, retinoic acid, isoretinoic acid and other retinoid compounds, adapalene, tazarotene, azelaic acid and azelaic acid derivatives, antibiotic agents, such as erythromycin and clyndamycin, coal tar, zinc salts and complexes, and combinations thereof, in a therapeutically effective concentration.

Antipsoriasis Agents

In an embodiment, the active agent is an anti-psoriasis agent. Such anti-psoriasis agent can be selected, among other options, from the group of keratolytically-active agents, salicylic acid, coal tar, anthralin, corticosteroids, vitamin D and derivatives and analogs thereof, including vitamin D3 analogs such as calcitriol, calcipotriol; retinoids, such as tazarotene and photodymamic therapy agents.

Antiinfective Agents

In an embodiment, the active agent is an anti-infective agent. Such anti-infective agent can be selected from the group of an antibiotic agent, an antibacterial agent, an antifungal agent, an agent that controls yeast, an antiviral agent and an antiparasitic agent. Exemplary antiinfective agents are exemplified by beta-lactam antibiotic, an aminoglycoside, an ansa-type antibiotic, an anthraquinone, an azole, metronidazole, an antibiotic glycopeptide, a macrolide, erythromycin, clindamycin, an antibiotic nucleoside, an antibiotic peptide, polymyxin B, an antibiotic polyene, an antibiotic polyether, an antibiotic quinolone, an antibiotic steroid, fucidic acid, mupirocin, chloramphenicol, a sulfonamide, tetracycline, an antibiotic metal, silver, copper, zinc, mercury, tin, lead, bismuth, cadmium, chromium, an oxidizing agent, iodine, iodate, a periodate, a hypochlorite, a permanganate, a substance that release free radicals and/or active oxygen, a cationic antimicrobial agent, a quaternary ammonium compound, a biguanide, chlorhexidine, a triguanide, a bisbiguanide, a polymeric biguanide and a naturally occurring antibiotic compound, as well as analogs, derivatives, salts, ions and complexes thereof.

Aprotic Polar Solvents with Therapeutic Properties

In certain embodiments, the aprotic polar solvent possesses therapeutic properties on its own and therefore, it can be regarded as "active agent". For example, DMSO acts as a topical analgesic, it reduces pain and it also reduces inflammation by several mechanisms. It is an antioxidant—a scavenger of the free radicals that gather at the site of injury.

Because aprotic polar solvents, such as DMSO increases the rate of absorption of some compounds through organic tissues including skin and nails, formulations comprising such aprotic polar solvents can be used as a drug delivery system.

Fields of Applications

The foamable carrier is suitable for treating any inflicted surface. In one or more embodiments, foamable carrier is suitable for administration to the skin, a body surface, a mucosal surface and a body cavity, e.g., the cavity and/or the mucosa of the nose, mouth, eye, ear, respiratory system, vagina or rectum (severally and interchangeably termed herein "target site").

By selecting a suitable active agent, or a combination of two or more active agents, the foamable composition is useful in treating an animal or a human patient having any one of a variety of dermatological disorders, including dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, ecthyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, granuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing moistens, gangrene, scarring, and vitiligo.

Likewise, the foamable composition is suitable for treating a disorder of a body cavity or mucosal surface, e.g., the mucosa of the nose, mouth, eye, ear, respiratory system, vagina or rectum. Non limiting examples of such conditions include chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranuloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum.

In an embodiment the composition is useful for the treatment of an infection. In one or more embodiments, the composition is suitable for the treatment of an infection, selected from the group of a bacterial infection, a fungal infection, a yeast infection, a viral infection and a parasitic infection.

In an embodiment the composition is useful for the treatment of wound, ulcer and burn.

In an embodiment the target site is selected from the group consisting of the skin, a body cavity, a mucosal surface, the nose, the mouth, the eye, the ear canal, the respiratory system, the vagina and the rectum.

The composition is also suitable for administering a hormone to the skin or to a mucosal membrane or to a body cavity, in order to deliver the hormone into the tissue of the target organ, in any disorder that responds to treatment with a hormone.

In an embodiment the target site is selected from the group consisting of the skin, a body cavity, a mucosal surface, the nose, the mouth, the eye, the ear canal, the respiratory system, the vagina and the rectum. In an embodiment the disorder is selected from the group consisting of dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, ecthyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, granuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo, chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranuloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum; and wherein the active agent is suitable for treating said disorder.

In one embodiment the disorder is an inflammation, skin inflammation, acne, rosacea, actinic keratosis, skin cancer, a local pain, joint pain and ostheoarthritis; the active agent is a nonsteroidal anti-inflammatory drug, given at a therapeutically effective concentration.

In one embodiment the disorder is psoriasis; the active agent is a vitamin D, a vitamin D derivative, a vitamin D analog, a vitamin D3 analog (such as calcitriol and calcipotriol) given at a concentration between about 0.0001% and about 0.02% by weight.

In one embodiment the active agent is permethrin. In a Preferred embodiment it is at a concentration between about 1% and about 8% by weight.

Cosmetic Use

In one or more embodiments, the aprotic polar solvent foamable carrier may be used for cosmetic use. For example it may be used as part of a cosmetic formulation to prevent a cosmetic disorder or to improve the skin. Alternatively it may be used with cosmetic effect for example as a cosmetic remover. Unexpectedly, it has been found that foam containing aprotic solvents displays advantages over the prior art removers. It can be dispensed in small quantities as a foam targeted to a surface and applied locally with mechanical force causing the foam to break. The aprotic solvent can then solubilize the cosmetic which can then be and removed for example using a cloth. The foam is short term stable and avoids the mess, spills and over use of liquid aprotic solvents.

The following examples further exemplify the aprotic polar solvent foamable pharmaceutical carriers, pharmaceutical compositions thereof, cosmetic carriers, cosmetic compositions thereof, methods for preparing the same, and uses of the compositions. The examples are for the purposes of illustration only and are not intended to be limiting of the invention. Many variations may be carried out by one of ordinary skill in the art and are contemplated within the full scope disclosed herein.

In one embodiment the foamable compositions and foams are suitable for use in treating, ameliorating, reducing or preventing a dermatological, cosmetic or mucosal disorder. More particularly, they are suitable for use where such disorders would otherwise be less responsive when treated with one agent alone.

Methods/Tests

General Manufacturing Procedures

The following procedures are used to produce the foam samples described in the examples below, in which only the steps relevant to each formulation are performed depending on the type and nature of ingredients used.

A) Waterless Formulations

Step 1: Gelling agents, if present, are added to the aprotic polar solvent at room temperature under mixing until formulation homogeneity is obtained.

Step 2: The mixture/solvent is warmed to about 50-60° C., surfactants and/or foam adjuvants, if present, are added under agitation until complete dissolution.

Step 3: Hydrophobic and/or hydrophilic solvents, if present are heated to 50-60° C. and added under mixing until formulation homogeneity is achieved.

Step 4: The mixture is cooled down to room temperature and temperature-sensitive agents (e.g., active agents), humectants, preservatives, pH-buffering agents or cosmetic agents, if present, are added under mixing until dissolution.

Step 5: The formulation is packaged in aerosol canisters which are crimped with a valve, pressurized with propellant and equipped with an actuator suitable for foam dispensing.

B) Aqueous or Water Containing Formulations

Step 1: Water is added to the aprotic polar solvent at room temperature. Gelling agents, if present, are added to the mixture at room temperature under mixing until formulation homogeneity is obtained.

Step 2: The mixture/aqueous solvent is warmed to about 50-60° C., surfactants and/or foam adjuvants, if present, are added under agitation until complete dissolution.

Step 3: Hydrophobic and/or hydrophilic solvents, if present, are heated to 50-60° C. and added under mixing until formulation homogeneity is achieved (to form an emulsion).

Step 4: The mixture is cooled down to room temperature and temperature-sensitive agents (e.g., active agents), humectants, preservatives, pH-buffering agents or cosmetic agents, if present, are added under mixing until dissolution.

Step 5: The formulation is packaged in aerosol canisters which are crimped with a valve, pressurized with propellant and equipped with an actuator suitable for foam dispensing.

Materials

TABLE 1

Exemplary possible ingredients suitable for the production of foamable compositions disclosed herein.

| Chemical Name | Function | Commercial Name | Supplier |
|---|---|---|---|
| Carbomer 934P | Gelling agent | Carbomer 934P | Spectrum |
| Carbomer copolymer Type A | Gelling agent | Pemulen TR-2 | Noveon |
| Ceteth 2 | Surfactant | Brij 52 | Fluka |
| Ceteth 20 | Surfactant | Lipocol C20 | Lipo |
| Cetostearyl alcohol | Foam adjuvant | Speziol C16-C18 | Cognis |
| Diclofenac sodium | Active agent | Diclofenac sodium | Sriken |
| Dimethyl Sulfoxide | Solvent | Dimethyl Sulfoxide | Fluka |
| Ethanol absolute | Solvent | Ethanol | J. T Baker |
| Glycerin | Humectant | Glycerin | Cognis |
| Glycerol Monostearate | Surfactant | Cutina GMS | Cognis |
| Hydroxypropyl cellulose | Gelling agent | Klucel EF | Hercules |
| Hydroxypropyl methylcellulose | Gelling agent | Methocel K100M | Colorcon Dow |
| Light Mineral Oil | Solvent | Light Liquid Paraffin | Gadot |
| Minocycline HCl | Active agent | Minocycline HCl | Hovione |
| Paraffin Wax | Thickener; Stabilizer | Paraffin 51-53 | Merck |
| PEG-100 Stearate | Surfactant | Myrj 59P | Uniqemqa |
| Petrolatum, White | Solvent | Sofmetic LMP | MMP |
| Poloxamer 188 | Gelling agent | Lutrol F68 | BASF |
| Poloxamer 407 | Gelling agent | Lutrol F127 | BASF |
| Polyglyceryl Oleate | Surfactant | Plurol Oleique CC497 | Gattefosse |
| Polysorbate 80 | Surfactant | Tween 80 | Croda |
| Propane/Isobutane/Butane (55:18:27) | Propellant | AP-70 | Aeropress Corporation |
| Propylene glycol | Humectant | Propylene Glycol | Gadot |
| Sorbitan Monooleate | Surfactant | Span 80 | Spectrum |
| Sorbitan Monostearate | Surfactant | Span 60 | Degussa |
| Steareth-2 | Surfactant | Sympatens AS/020G | Kolb |
| Stearic Acid | Foam adjuvant | Edenor ST1 | Cognis |
| Stearyl Alcohol | Foam adjuvant | Speziol C18 | Cognis |
| Terbinafine HCl | Active agent | Terbinafine HCl | Taro |
| Urea | Humectant | carbamide | Gadot |
| Xanthan Gum | Gelling agent | Xanthan Gum 11K | CP Kelco US |

Production Under Vacuum

Optionally, the foamable carrier may be produced under nitrogen and under vacuum. Whilst the whole process can be carried out under an oxygen free environment, it can be sufficient to apply a vacuum after heating and mixing all the ingredients to obtain an emulsion or homogenous liquid. Preferably the production chamber is equipped to apply a vacuum but if not the formulation can be for example placed in a desiccator to remove oxygen prior to filing and crimping.

Canisters Filling and Crimping

Each aerosol canister is filled with the pre-foam formulation ("PEE", i.e., foamable carrier) and crimped with valve using vacuum crimping machine. The process of applying a vacuum will cause most of the oxygen present to be eliminated. Addition of hydrocarbon propellant may without being bound by any theory further help to reduce the likelihood of any remaining oxygen reacting with the active ingredient. It may do so, without being bound by any theory, by one or more of dissolving in the oil or hydrophobic phase of the formulation, by dissolving to a very limited extent in the aqueous phase, by competing with some oxygen from the formulation, by diluting out any oxygen, by a tendency of oxygen to occupy the dead space, and by oxygen occupying part of the space created by the vacuum being the unfilled volume of the canister or that remaining oxygen is rendered substantially ineffective in the formulation.

Pressurizing

Pressurizing is carried out using a hydrocarbon gas or gas mixture. Canisters are filled and then warmed for 30 seconds in a warm bath at 50° C. and well shaken immediately thereafter.

Tests

By way of non-limiting example stability tests are briefly set out below as would be appreciated by a person of the art.

Collapse Time

Collapse time (CT) is examined by dispensing a given quantity of foam and photographing sequentially its appearance with time during incubation at 36° C. It is useful for evaluating foam products, which maintain structural stability at skin temperature for at least 1 minute. Foams which are structurally stable on the skin for at least one minute are termed "short term stable" carriers or foams.

Density

In this procedure, the foam product is dispensed into vessels (including dishes or tubes) of a known volume and weight. Replicate measurements of the mass of foam filling the vessels are made and the density is calculated. The canister and contents are allowed to reach room temperature. Shake the canister to mix the contents and dispense and discard 5-10 mL. Then dispense foam into a pre-weighed tube, filling it until excess is extruded. Immediately remove (level off) excess foam at both ends and weigh the filled tube on the weighing balance.

Viscosity

Viscosity is measured with Brookfield LVDV-II+PRO with spindle SC4-25 at ambient temperature and 10, 5 and 1 RPM. Viscosity is usually measured at 10 RPM. However, at about the apparent upper limit for the spindle of ~>50,000 CP, the viscosity at 1 RPM may be measured, although the figures are of a higher magnitude.

Chemical Stability

The amount of active agent present is analyzed in foam expelled from various pressurized canisters containing foam formulations using HPLC. Analysis is carried out at zero time and at appropriate time intervals thereafter. The canisters are stored in controlled temperature incubators at one or more of 5 C, at 25 C, at, 40 C and at 50 C. At appropriate time intervals canisters are removed and the amount of active agent in the foam sample is measured.

Bubble Size

Foams are made of gas bubbles entrapped in liquid. The bubble size and distribution reflects in the visual texture and smoothness of the foam. Foam bubbles size is determined by dispensing a foam sample on a glass slide, taking a picture of the foam surface with a digital camera equipped with a macro lens. The diameter of about 30 bubbles is measured manually relatively to calibration standard template. Statistical parameters such as mean bubble diameter, standard deviation and quartiles are then determined. Measuring diameter may also be undertaken with image analysis software. The camera used was a Nikon D40X Camera (resolution 10 MP) equipped with Sigma Macro Lens (ref: APO MACRO 150 mm F2.8 EX DG HSM). Pictures obtained are cropped to keep a squared region of 400 pixels×400 pixels.

Microscopic Observation

The light microscope enables observing and measuring particles from few millimeters down to one micron. Light microscope is limited by the visible light wavelength and therefore is useful to measuring size of particles above 800 nanometers and practically from 1 micron (1,000 nanometers).

Figure 3:
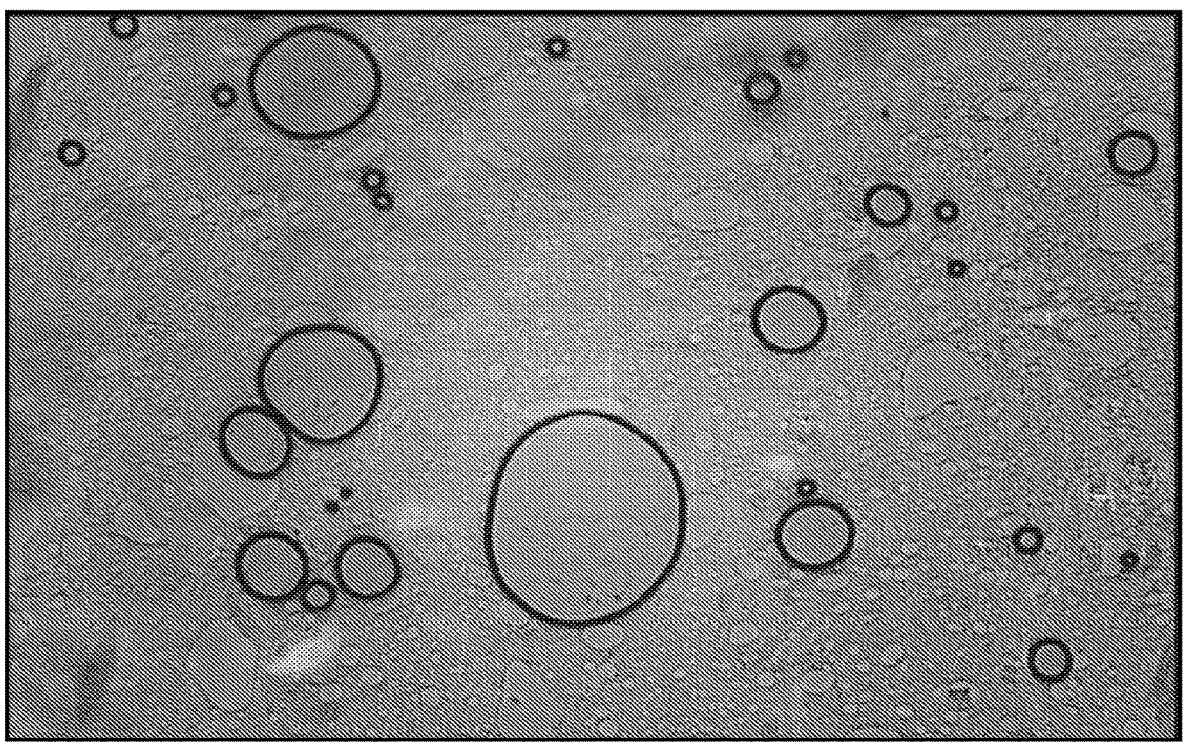
FIG. 3 is a color microscope picture of a foam produced from formulation D30 comprising DMSO and mineral oil.
Figure 4:
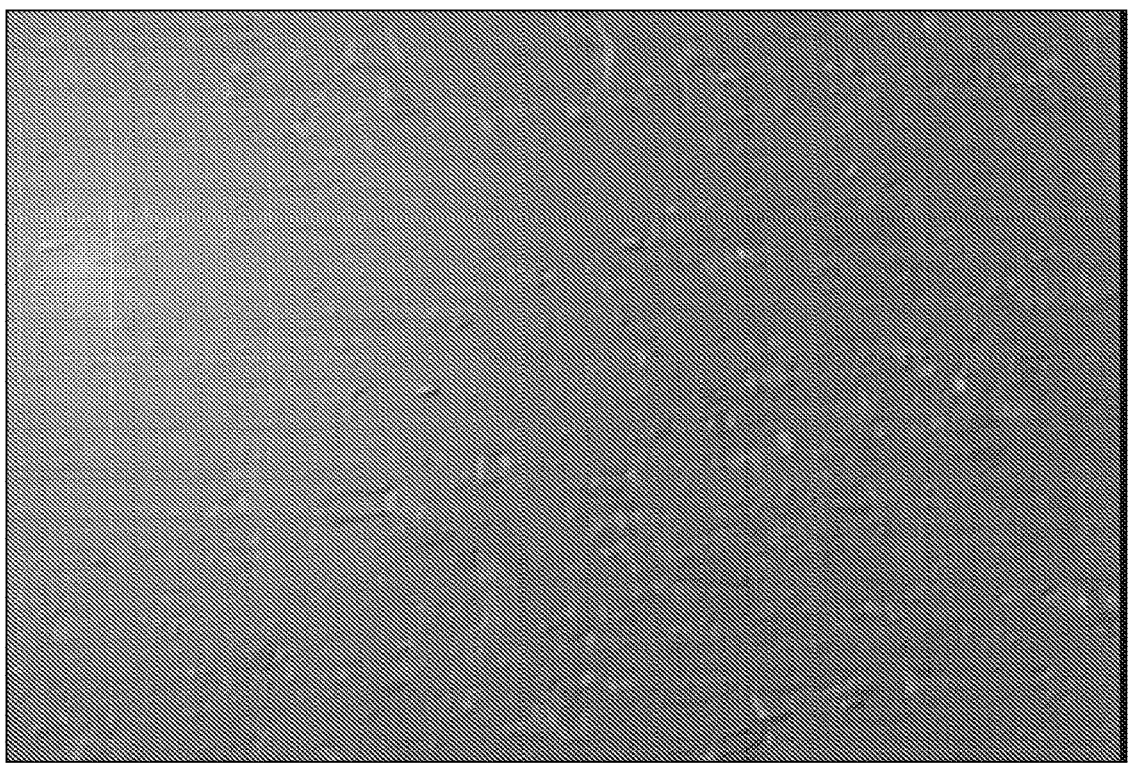
FIG. 4 is a microscope picture at ×200 of a waterless DMSO foam sample from formulation D24 showing a single-phase homogeneous preparation free of crystals or agglomerations.
Figure 5:
FIG. 5 is a Microscope picture at ×200 of an aqueous DMSO foam sample from formulation D33 showing a single-phase homogeneous preparation free of crystals or agglomerations.

When foam is examined under a microscope for the presence of particles, crystals or agglomerates, for example, a cover slide is carefully placed over a small foam sample and pressure is applied to the cover causing most of the bubbles to break. Some of the foam bubbles can sometimes still be observed in the formulations, as can be seen in FIG. 3. The fluid under the cover slide can then be viewed to identify whether or not there are any particles, crystals or agglomerates.

Shakability

Shakability represents the degree to which the user is able to feel/hear the presence of the liquid contents when the filled pressurized canister is shaken. Shaking is with normal mild force without vigorous shaking or excessive force. When the user cannot sense the motion of the contents during shaking the product may be considered to be non-shakable. This property may be of particular importance in cases where shaking is required for affecting proper dispersion of the contents.

Shakability Scoring:

| | |
|---|---|
| Good shakability (conforms to required quality specification) | 2 |
| Moderate shakability (conforms to required quality specification) | 1 |
| Not shakable (fails to meet required quality specification) but may still be flowable and allow foam formation of quality | 0 |
| Is substantially not able to pass through valve | Block |

EXAMPLES

The invention is described with reference to the following examples. This invention is not limited to these examples and experiments. Many variations will suggest themselves and are within the full intended scope.

Section A—Waterless Aprotic Foamable Vehicles

Example 1—Waterless Composition Containing Dimethyl Sulfoxide ("DMSO") Alone

| Formulation | % w/w D01 |
|---|---|
| Ingredients | |
| Dimethyl Sulfoxide (DMSO) | 100.0 |
| Total | 100.0 |
| Propellant AP-70 | 10.0 |
| Foam Properties | |
| Foam Quality | Poor |
| Collapse Time (sec) | 0 |

Comments: Formulation D01 did not give a foam, but a bubbly liquid. DMSO alone does not have self-foaming or foam-boosting properties. The results may also suggest a defoaming effect or role of aprotic solvents.

Example 2—Waterless Compositions Containing Dimethyl Sulfoxide and Various Polymeric (Gelling) Agents Part A

| Formulations | D02 | D03 | D04 | D05 | D06 |
|---|---|---|---|---|---|
| Ingredients | | | | | |
| Dimethyl Sulfoxide | 99.0 | 98.0 | 98.0 | 95.0 | 98.0 |
| Xanthan Gum | 1.0 | — | — | — | — |
| Hydroxypropyl cellulose | — | 2.0 | — | — | — |
| Pemulen TR-2 | — | — | 2.0 | — | — |
| Poloxamer 188 | — | — | — | 5.0 | — |
| Carbomer 934P | — | — | — | — | 2.0 |
| Total | 100.0 | 100.0 | 100.0 | 100.0 | 100.0 |
| Propellant AP-70 | 10.0 | 10.0 | 10.0 | 10.0 | 10.0 |
| Foam Properties | | | | | |
| Foam Quality | Poor | Fair | Fair | Fair | Fair |
| Collapse Time (sec) | 0 | 5 | 30 | 5 | 0 |

Comments: Various different gelling agents were mixed with DMSO. With the exception of xanthan gum, all the other polymers dissolved in DMSO to form liquid gels prior to the addition of propellant. Xanthan did not dissolve and remained as a powder. Compositions D02 to D06, merely produced either bubbly liquids or very watery foams that rapidly collapse and not of quality. The results may also indicate a defoaming effect or role of aprotic solvents.

Part B

| Formulations | D07 | D08 |
|---|---|---|
| Ingredients | | |
| Dimethyl Sulfoxide | 99.5 | 99.0 |
| Hydroxypropyl methylcellulose K100M | 0.5 | 1.0 |
| Total | 100.0 | 100.0 |
| Propellant AP-70 | 10.0 | 10.0 |
| Foam Properties | | |
| Foam Quality | Good | Good |
| Collapse Time (sec) | 30 | 45 |

Comments: Surprisingly, the addition of hydroxypropyl methylcellulose to DMSO improves the foam quality and gave good quality foams. In contrast hydroxypropyl cellulose without the methyl group even with 4 times the concentration does not produce a foam of quality with DMSO. Moreover, and increase in the hydroxypropyl methylcellulose concentration from 0.5% to 1% improved the foam collapse time from 30 sec to 45 sec. There is however still is a need for a longer collapse time to improve ease of application on the skin. In one or more embodiments the polymeric or gelling agent is hydroxypropyl methylcellulose.

Part C

| Formulations | D22B | D22C |
|---|---|---|
| Ingredients | | |
| Dimethyl Sulfoxide | 95.0 | 99.0 |
| Hydroxypropyl methylcellulose K100M | — | 0.5 |
| Parrafin 51-53 | 5.0 | 5.0 |
| Total | 100.0 | 100.0 |
| Propellant AP-70 | 10.0 | 10.0 |
| Foam Properties | | |
| Foam Quality | Poor | Poor |
| Collapse Time (sec) | Immediate | Immediate |

Comments: Whilst it was shown above in Part B that the addition of hydroxypropyl methylcellulose to DMSO can improve foam quality and generate good quality foam it can been seen here that in the presence of paraffin wax hydroxypropyl methylcellulose was ineffective and poor foam was produced.

Example 3—Waterless Compositions Containing Dimethyl Sulfoxide and Surface Active Agents

| Formulations | HLB | Physical state | % w/w |||||||| 
|---|---|---|---|---|---|---|---|---|---|---|
| | | | D09 | D10 | D11 | D12 | D13 | D14 | D15 | D16 |
| Ingredients | | | | | | | | | | |
| Dimethyl Sulfoxide | — | Liquid | 97.0 | 97.0 | 97.0 | 97.0 | 97.0 | 97.0 | 97.0 | 94.0 |
| Tween 80 | 15.0 | Liquid | 3.0 | — | — | — | — | — | — | — |
| Ceteth 20 | 15.7 | Solid | — | 3.0 | — | — | — | — | — | 3.0 |
| Polyglyceryl Oleate | 6.0 | Liquid | — | — | 3.0 | — | — | — | — | — |
| Sorbitan Monooleate | 4.3 | Liquid | — | — | — | 3.0 | — | — | — | — |
| Ceteth 2 | 5.3 | Solid | — | — | — | — | 3.0 | — | — | 3.0 |
| Sorbitan Monostearate | 4.7 | Solid | — | — | — | — | — | 3.0 | — | — |
| Glycerol Monostearate | 3.8 | Solid | — | — | — | — | — | — | 3.0 | — |
| Total | — | — | 100 | 100 | 100 | 100 | 100 | 100 | 100 | 100 |
| Propellant AP-70 | — | Gas | 10.0 | 10.0 | 10.0 | 10.0 | 10.0 | 10.0 | 10.0 | 10.0 |
| Foam Properties | | | | | | | | | | |
| Foam Quality | — | — | Poor | Fair | Poor | Poor | Good | Good | Excellent | Good |
| Collapse Time (sec) | — | — | 0 | 5 | 0 | 0 | 10 | >180 | >180 | 10 |

Comments: Various different non-ionic surfactants (surface active agents) were dissolved into DMSO. As shown in formulations D09 to D12, the addition of several surfactants of various HLB values and physical states (solid vs. liquid) merely produced either bubbly liquids or very watery foams that rapidly collapse and not of quality. Formulations D13 and D16 gave good quality foams, but they quickly collapsed and turned into bubbly liquids. Combining linear surfactants one with a high HLB and one with a low HLB (see D16) did not appear to result in any improvement. Therefore, it is not obvious how to create good quality breakable foams with random addition of surfactants.

However, very surprisingly, the addition of sorbitan monostearate or glycerol monostearate to DMSO dramatically improved the foam quality and good to excellent quality breakable foams were produced, which did not collapse after 180 sec of incubation at 36° C. Upon application to a target site and a simple rub of the foams with the hand, these quality foams broke, spread evenly over the skin and were readily absorbed into the skin. For waterless formulations a solid surfactant with a low HLB is preferred.

It can be noted that sorbitan monostearate and glycerol monostearate share some common properties: both of them are solids at room temperature; have a linear fatty acid chain; a polar head (glycerol/sorbitan) and have an HLB value smaller that 5.0. Each one of these properties taken alone is not sufficient to create a good quality breakable foam, as described in formulations D09 to D12 and D16. But without being bound by any theory it is thought that when the properties of solid at room temperature, low HLB, linear hydrophobic chain with a polar head are combined, they act synergistically to create good to excellent quality breakable foams as shown in formulations D14 and D15. In one or more embodiments the surface active agent is a solid with a low HLB. In further embodiments the surface active agent may include a linear hydrophobic chain and a polar head.

Example 4—Waterless Foamable Compositions Containing Dimethyl Sulfoxide, Surface Active Agents and Examples of Different Active Agents

| Formulations | % w/w |||
|---|---|---|---|
| | D17 | D18 | D19 |
| Ingredients | | | |
| Dimethyl Sulfoxide | 92.0 | 96.0 | 96.0 |
| Glycerol Monostearate | 3.0 | 3.0 | 3.0 |
| Diclofenac | 5.0 | — | — |
| Minocycline HCl | — | 1.0 | — |
| Terbinafine | — | — | 1.0 |
| Total | 100.0 | 100.0 | 100.0 |
| Propellant AP-70 | 10.0 | 10.0 | 10.0 |
| Foam Properties | | | |
| Foam Quality | Good | Good | Good |
| Collapse Time (sec) | >180 | >180 | >180 |
| Presence of drug crystals | None* | None* | None* |

*Whilst the API was dissolved some very few surfactant crystals were noted. In one or more embodiments crystals are eliminated or substantially eliminated. By way of non limiting example a co-solvent or a co-surfactant may be added to dissolve the crystals or the amount of agent may be reduced to an optimal level where the crystals dissolve.

Comments: Several active pharmaceutical agents ("API") were dissolved into stock formulation D15 described above, containing DMSO and glycerol monostearate. As shown in formulations D17 to D19, the addition of various drugs gave good quality breakable foams which did not collapse after 180 sec of incubation at 36° C. Moreover, microscopic observation of foam samples revealed the API's were dissolved in these formulations. It follows that the API bioavailability should be improved if dissolved since the DMSO can then aid penetration Example 5—Waterless Compositions Containing Dimethyl Sulfoxide and Combinations of Foam Adjuvants, Polymeric with and without Surface Active Agents

| Part A - With Surface Active Agents | | | | | | |
|---|---|---|---|---|---|---|
| | % w/w | | | | | |
| Formulations | D26 | D23 | D24 | D25 | D15 | D55 |
| Ingredients | | | | | | |
| Dimethyl Sulfoxide | 94.0 | 94.0 | 93.5 | 96.5 | 97 | — |
| Dimethyl Formamide | — | — | — | — | — | 97 |
| Stearyl Alcohol | 3.0 | 3.0 | 3.0 | — | — | — |
| Glycerol Monostearate | — | 3.0 | 3.0 | 3.0 | 3.0 | 3.0 |
| Tween 80 | 3.0 | — | — | — | — | — |
| Hydroxypropyl methylcellulose K100M | — | — | 0.5 | 0.5 | — | — |
| Total | 100.0 | 100.0 | 100.0 | 100.0 | 100.0 | 100.0 |
| Propellant AP-70 | 10.0 | 10.0 | 10.0 | 10.0 | 10.0 | 10.0 |
| Foam Properties | | | | | | |
| Foam Quality | Good | Good | Good | Good | Excellent | Poor |
| Collapse Time (sec) | 10 | >180 | >180 | >180 | >180 | 0 |

Comments: A foam adjuvant (stearyl alcohol) was dissolved into DMSO and used with a surfactant Tween. Although the formulation produced a good quality foam it collapsed almost immediately. As shown in Formulation D26, the random combination of a foam adjuvant and a surfactant does not achieve satisfactory results in terms of foam quality and stability, showing the need for an appropriate selection of the foam stabilizing components as taught in this disclosure. Replacing Tween with glycerol monostearate produced quality foam with a collapse time of more than three minutes. In the presence of glycerol monostearate the addition of a foam adjuvant or a gelling agent produced no significant change in the measured parameters. Thus, formulations D23, D24 and D25 describe combinations of two or more stabilizing components appropriately selected from the group consisting of a surfactant; a foam adjuvant and a gelling agent that gave good quality breakable foams that did not collapse after 180 sec at 36° C.

There are advantages to combine one or both of foam adjuvants and gelling agents with surfactants, as this can inter alia bring; a higher formulation viscosity and structure which is suitable for formulations which are to contain a suspension of non-dissolved active agents and thus provide a more homogeneous API suspension; an improved foaming; a more stable emulsion; greater stability when the propellant is added into the formulation, although adding an inappropriate combination or too high viscosity can lead to destabilization on addition of propellant such that successful combinations and the amounts are non obvious in order to achieve a foam of quality and a stable foamable formulation. Moreover, achieving a specific type of foam and foam properties is certainly non obvious. Nevertheless, in one or more embodiments the combination of foam adjuvants and gelling agents with surfactants may enable a decrease in the surfactant concentration without any degradation of the foam properties. Such a decrease in surfactant concentration can be desirable in topical applications, as lower levels can avoid or minimize potential irritation, particularly if the formulations are to be used on sensitive targets such as wounds or body cavities. Moreover, such combinations have been unexpectedly observed to produce surprising synergetic effects.

Formulation D55 containing Dimethylformamide in contrast to what was surprisingly observed with DMSO fails to give a foam of acceptable quality, showing that not all aprotic polar solvents are suitable to be used at high concentrations in combination with glyceryl monostearate.

| Part B - Without Surface Active Agents | | | | |
|---|---|---|---|---|
| | % w/w | | | |
| Formulations | D20 | D21 | D07 | D22 |
| Ingredients | | | | |
| Dimethyl Sulfoxide | 97.0 | 97.0 | 99.5 | 96.5 |
| Stearyl Alcohol | — | 3.0 | — | 3.0 |
| Stearic Acid | 3.0 | — | — | — |
| Hydroxypropyl methylcellulose K100M | — | — | 0.5 | 0.5 |
| Total | 100.0 | 100.0 | 100.0 | 100.0 |
| Propellant AP-70 | 10.0 | 10.0 | 10.0 | 10.0 |
| Foam Properties | | | | |
| Foam Quality | Poor | Good | Good | Good |
| Collapse Time (sec) | 0 | 10 | 30 | 120 |

A foam adjuvant was dissolved in DMSO instead of a surfactant. As seen from formulations D20 and D21, the addition of stearic acid to DMSO gave a bubbly liquid whereas the addition of stearyl alcohol gave a good quality foam but that collapsed almost immediately after 10 sec.

Interestingly, both stearyl alcohol and hydroxypropyl methylcellulose when used separately with DMSO give good quality foams that quickly collapse, after 10 and 30 sec respectively, as seen in formulations D21 and D07. But very surprisingly, when these two components are combined with DMSO, they act synergistically to produce a good quality foam with a substantially improved collapse time of 120 seconds as seen in formulation D22.

In one or more embodiments there is provided a surfactant-free foam formulation comprising DMSO, and fatty alcohols and polymeric agents. In one or more alternative embodiments there is provided a surfactant-free foam formulation comprising DMSO, and fatty alcohols essentially free of polymeric agents. In one or more other embodiments there is provided a surfactant-free foam formulation comprising DMSO and polymeric agents essentially free of fatty alcohols.

Example 6—Comparison of Waterless Foamable Vehicle Compositions Containing DMSO and Urea/Ethanol/Lipophilic Compound with a Control Formulation Containing Water and a Classic Emulsion Foam Formulation

| PART A - DMSO Formulations | | | | |
|---|---|---|---|---|
| Formulation | % w/w D27 | % w/w D50 | % w/w D52 | % w/w D51 |
| Ingredients | | | | |
| Dimethyl Sulfoxide | 45.0 | 45.0 | 45.0 | 45.0 |
| Glycerin (humectant) | 15.0 | 15.0 | 15.0 | 15.0 |

PART A - DMSO Formulations

| Formulation | % w/w D27 | % w/w D50 | % w/w D52 | % w/w D51 |
|---|---|---|---|---|
| Propylene glycol (humectant) | 15.0 | 15.0 | 15.0 | 15.0 |
| Ethanol | 20.0 | — | — | — |
| Urea | — | 20.0 | — | — |
| Petrolatum | — | — | 20.0 | — |
| Water | — | — | — | 20.0 |
| Cetostearyl alcohol | 1.5 | 1.5 | 1.5 | 1.5 |
| Steareth-2 | 2.0 | 2.0 | 2.0 | 2.0 |
| Hydroxypropyl cellulose EF | 1.5 | 1.5 | 1.5 | 1.5 |
| Total | 100.0 | 100.0 | 100.0 | 100.0 |
| Propellant AP-70 | 8.0 | 8.0 | 8.0 | 8.0 |
| Foam properties | | | | |
| Foam Quality | Good to Excellent | Good | Good | Good |
| Shakability | Good | Good | Good | Good |
| Density | NM | 0.034 | 0.097 | 0.063 |
| Collapse | NM | >180 | 180 | >180 |
| Any after taste | NM | No | Very Slight | Yes |
| Any Breath odour | NM | No | Very Slight | Yes |

NM = Not Measured

Comments: Formulations D27 is an example of a waterless foam of good to excellent quality containing 45% DMSO, Ethanol, humectants, a foam adjuvant, a low HLB solid surfactant and a gelling agent. It can be noted that the addition of about 20% of ethanol did not appear to affect the foam stability or quality.

A preliminary study was run with formulations D50, D51 and D52 to determine whether any formulations can prevent the known side effect of or after taste and breath odor after use of DMSO. These DMSO side effects were observed to be suppressed when urea is added to the formulation (see D50), are unexpectedly greatly reduced in case of petrolatum (see D52), but are still present when water is added to the formulation (see D51). Thus, in one or more embodiments, there are provided DMSO formulations that are useful in reducing after taste and breath odor side effects.

Comments: All the formulations D50, D51, D52, produced good to excellent quality foam with low density and good collapse time. To determine which formulations would be compatible and suitable for use with human skin and their hydration effect, if any, double blind corneometer studies were carried out to determine the skin-hydration effect of the formulations.

Part B—Manufacturing Procedure
Formulation D50:
1) Add Hydroxypropyl cellulose EF to water at room temperature while mixing to "Gel".
2) Heat to 50-60° C. and add Cetostearyl alcohol and Steareth-2 while mixing to dissolution.
3) Add slowly Glycerin anhydrous and Propylene glycol while mixing to homogeneity.
4) Cool to RT and add slowly Urea while mixing to homogeneity.
5) Complete water if necessary to 100%

Formulation D51:
1) 2) 3) and 5) as above; 4) Cool to room temperature and add slowly water while mixing to homogeneity.

Formulation D52:
1) 2) 3) and 5) as above; 4) Cool to room temperature and add slowly Petrolatum while mixing to homogeneity.

Formulation D27:
1) 2) 3) and 5) as above; 4) Cool to room temperature and add slowly Ethanol while mixing to homogeneity.

Part C—Corneometer Study
Comparison of Formulations D50, D51, D52 with DMSO and a Classic Emollient tested for skin hydration.

| Classic Emollient | % w/w |
|---|---|
| Isopropyl myristate | 6.00 |
| Glycerol monostearate | 0.50 |
| PEG-40 stearate | 3.00 |
| Stearyl alcohol | 1.00 |
| Xanthan gum | 0.30 |
| Methocel K100M | 0.30 |
| Polysorbate 80 | 1.00 |
| Water | 81.30 |
| Preservative | 0.60 |
| Total | 100.00 |
| Propellant AP70 | 8.00 |

Skin hydration is measured using a Corneometer® CM 825 instrument. (Courage+Khazaka, Koln, Germany). The measuring principle of the Corneometer® CM 825 is based on capacitance measurement of dielectric medium. Any change in the dielectric constant due to skin surface hydration alters the capacitance of a measuring capacitor. It is capable of detecting even slight changes in the skin hydration level.

Study Flow chart is shown below:

| STUDY ACTIVITY | Baseline* | 4 hours |
|---|---|---|
| Inclusion/exclusion criteria | X | |
| Application of the test preparations | X | |
| Assessment of skin hydration | | X |
| Assessment of tolerability parameters and Adverse Events | | X |

Skin hydration level is assessed at baseline with the Corneometer® CM 825. The formulations are applied in designated chambers under occlusion for 4 hours which are then removed and the skin cleaned. Hydration is then measured.

Study protocol: The study was performed in a temperature controlled room (20-24° C.). Subjects washed their arms with water (no soap) and dried their arms with dry paper towel. Formulations were applied using test chambers. The location of each chamber within the stripe was marked once applied (maximum of 6 stripes on each arm). Each stripe contained only one formulation. One stripe served as a control, non treated area. Formulations, control products and control non treated areas were randomly assigned to the treatment sites according to a randomization list, provided by the study statistician. The application array was unknown to the study operator and subjects. An amount of approximately 4 mg (40 ul) of each of the study formulations was applied on the treatment sites as described by the randomization list. Skin hydration level was assessed at baseline T=0 (minimum 15 minutes following rinse), using the Corneometer® CM 825, and tested based on study design.

Healthy subjects were applied with single dose of formulations D50, D51, and D52 as shown in Part A above and the emollient formulation herein. As shown in FIG. 1 and FIG. 2, quite unexpectedly the formulations with DMSO have a substantial moisturizing effect when compared with the control and with the Classic Emollient. No significant difference can be seen from the addition of Urea, Petrolatum and Water to the DMSO based formulations. It can be appreciated that the moisturizing effect does not come from urea, petrolatum or water since the effect is closely similar in all three cases. This is completely surprising since DMSO is known for its quick penetration. Also very surprisingly, is the discovery that waterless DMSO formulations D50 and D52 have a substantial moisturizing effect despite the lack of water and additionally they can ameliorate against after taste and breath odor side effects. Thus, in one or more embodiments there are provided DMSO formulations that are useful in improving skin hydration.

Part D - Aprotic-Alcoholic formulations with 0% 20% and 40% ethanol and Foam Properties

| Formulation | % w/w D50 | % w/w D27 | % w/w D101 |
|---|---|---|---|
| Ingredients | | | |
| Dimethyl Sulfoxide | 45.00 | 45.00 | 45.00 |
| Glycerin (humectant) | 15.00 | 15.00 | — |
| Propylene glycol (humectant) | 15.00 | 15.00 | 6.50 |
| Ethanol | 0.00 | 20.00 | 40.00 |
| Urea | 20.00 | — | — |
| Cetostearyl alcohol | 1.50 | 1.50 | 3.00 |
| Steareth-2 | 2.00 | 2.00 | 4.00 |
| Hydroxypropyl cellulose EF | 1.50 | 1.50 | 1.50 |
| Total | 100.00 | 100.00 | 100.00 |
| Propellant AP-70 | 8.00 | 8.00 | 8.00 |
| Foam properties | | | |
| Foam Quality | Good | Good to Excellent | Poor |
| Shakability | Good | Good | Good |
| Collapse Time at 36° C. (sec) | >180 | NM* | Immediate |

*NM: Not Measured

Comments: Formulations D27, D50 and D101 were prepared according to the General Manufacturing Procedures described in the Method/Test section. As can be seen from the above Table Formulations D27 D50, which are waterless formulations containing up to 20% ethanol provide good to excellent quality breakable foams. However, when the ethanol content reaches 40% of the formulation, a clear defoaming effect is observed and no quality foam was produced, unlike as in formulation D101. The aprotic alcoholic defoaming effect was observed in the presence of surfactant so it follows that in the absence of surfactant the defoaming effect may be of the same order or more pronounced. So in one or more embodiments the level of short chain alcohols, such as, ethanol, is about or less than about 35%, is about or less than about 30%; is about or less than about 25%, is about or is less than about 20%, is about or is less than about 15%, is about or less than about 10%, is about or is less than about 5%.

Example 7—Waterless Foamable Vehicle Compositions Containing DMSO and a Hydrophobic Solvent

| Formulations | % w/w | | |
|---|---|---|---|
| | D28 | D29 | D30 |
| Ingredients | | | |
| Dimethyl Sulfoxide | 77.0 | 73.5 | 69.0 |
| Stearyl Alcohol | — | 3.0 | 5.0 |
| Glycerol Monostearate | 3.0 | 3.0 | 5.0 |
| Hydroxypropyl methylcellulose K100M | — | 0.5 | 1.0 |
| Light Mineral Oil | 20.0 | 20.0 | 20.0 |
| Total | 100.0 | 100.0 | 100.0 |
| Propellant AP-70 | 10.0 | 10.0 | 10.0 |
| Foam Properties | | | |
| Foam Quality | Fairly Good | Good | Good |
| Collapse Time (sec) | 90 | 150 | >180 |

Comments: A hydrophobic solvent was added into a mixture of DMSO and glyceryl monostearate. As shown in formulation D28, the addition of mineral oil to DMSO gave a fairly good quality foam that collapsed after 90 sec. In comparison with example D15 (containing DMSO and glyceryl monostearate only), it can be seen that the addition of a hydrophobic solvent has a defoaming effect.

Formulations D29 and D30 show that, when sufficient amounts of a foam adjuvant and a gelling agent are further added to the components of formulation D28, good quality breakable foam that did not collapse after 180 sec can be produced. Thus, in the presence of a hydrophobic solvent the inclusion of additional foam stabilizers to the surfactant substantially improves collapse time.

FIG. 3 depicts a microscopic observation of formulation D30 where droplets can been seen, showing that mineral oil and dimethyl sulfoxide form an emulsion in the presence of a surface active agent. Dimethyl sulfoxide is immiscible with hydrophobic solvents. Thus, it will form a waterless emulsion with hydrophobic solvents with surfactant. Having a hydrophobic solvent present can add to the sensory feeling and help to maintain skin moisture and oil. Although DMSO can aid penetration of other ingredients into the skin and mucosal membrane because DMSO is not miscible per se with hydrophobic solvents it leads to another useful property and advantage; namely that for topical and mucosal body cavity use, where the formulations are to be repeatedly applied and left on the skin or within the body cavity DMSO should not lead to stripping of the skin or mucosal membrane of oils.

Section B—Aqueous or Water Containing Aprotic Formulations

Example 8—Compositions Containing 45% Dimethyl Sulfoxide, Water and Surface Active Agents

| Formulations | HLB | Physical state | % w/w | | | | |
|---|---|---|---|---|---|---|---|
| | | | D32 | D33 | D34 | D35 | D36 |
| Ingredients | | | | | | | |
| Dimethyl Sulfoxide | — | Liquid | 45.0 | 45.0 | 45.0 | 45.0 | 75.0 |
| Water | — | Liquid | 52.0 | 52.0 | 52.0 | 52.0 | 20.0 |
| Tween 80 | 15.0 | Liquid | 3.0 | — | — | — | — |
| Ceteth 20 | 15.7 | Solid | — | 3.0 | — | — | — |
| PEG-100 Stearate | 18.8 | Solid | — | — | — | — | 5.0 |
| Sorbitan Monooleate | 4.3 | Liquid | — | — | 3.0 | — | — |
| Glycerol Monostearate | 3.8 | Solid | — | — | — | 3.0 | — |
| Total | — | — | 100.0 | 100.0 | 100.0 | 100.0 | 100.0 |
| Propellant AP-70 | — | Gas | 10.0 | 10.0 | 10.0 | 10.0 | 8.0 |
| Foam Properties | | | | | | | |
| Foam Quality | — | — | Excellent | Excellent | Fairly Good | Fair | Fairly Good |
| Collapse Time (sec) | — | — | 90 | 75 | 45 | 20 | not measured |

Comments: Various different surfactants were dissolved into a mixture of DMSO and water. As shown in formulation D34 and D35, the addition of solid or liquid surfactants of HLB value smaller than 5 does not give satisfying foams, but either bubbly liquids or very watery foams that rapidly collapse. This is in contrast to what was observed with waterless formulations where low HLB solid surfactants with a linear fatty acid and a more polar head were preferred. Glycerol monostearate which produces excellent waterless quality foams with DMSO is rendered ineffective here by the addition of water. Further, as seen in formulation D36, the addition of PEG-100 Stearate, a solid surfactant with a high HLB value of 18.8 produced a very watery foam. Thus, making quality foams containing both water and dimethyl sulfoxide is not obvious considering was has been learned above in the production of waterless DMSO foams.

However, surprisingly, the addition of liquid or solid surfactants of HLB value close to 15 such as Tween 80 and Ceteth 20 to the water/DMSO mixture dramatically improves the foam quality. Moreover, this was achieved without the addition of polymer to stabilize the foam. As shown in formulations D32 and D33, excellent quality breakable foams were produced, that did not collapse after 75 to 90 seconds of incubation at 36° C. Upon application to a target site and a simple rub of the foams with the hand, the foams broke, spread evenly over the skin and were readily absorbed into the skin. Without being bound by any theory it may be that the range of surfactants which can be applied successfully in aqueous or water containing DMSO formulations is much wider than available for waterless formulations.

Example 9—Compositions Containing from 25% to 75% DMSO

| PART A - Formulation containing surfactants | | | | |
|---|---|---|---|---|
| | % w/w | | | |
| Formulations | D36 | D38 | D37 | D39 |
| Ingredients | | | | |
| Dimethyl Sulfoxide | 75.0 | 75.0 | 25.0 | 75.0 |
| Water | 20.0 | 20.0 | 70.0 | 20.0 |
| Poloxamer 188 | — | 5.0 | 3.0 | 3.0 |
| PEG-100 Stearate | 5.0 | — | 2.0 | 2.0 |
| Total | 100.0 | 100.0 | 100.0 | 100.0 |
| Propellant AP-70 | 8.0 | 8.0 | 8.0 | 8.0 |
| Foam Properties | | | | |
| Foam Quality | Fairly Good | Fairly Good | Good | Good |

Comments: Formulations D36 and D38 each of which contained only one foam stabilizing component (PEG-100 Stearate and Poloxamer respectively) provided only fairly good foam quality. However, formulations D37 and D39, which contain at least two foam stabilizing components (Cetostearyl alcohol+Poloxamer 407+Methocel K100M; or Poloxamer 188+PEG 100-Stearate) provided good to excellent foam quality. It is interesting to note that PEG-100 Stearate alone and Poloxamer alone fail to produce foams of good quality even at 5% by weight (see formulations D36 and D38). However, when these two components are combined, they surprisingly act synergistically to provide stable and breakable foams of good quality. Thus in one or more embodiments the aprotic foamable compositions comprise a synergistic combination of surface active agent and a polamer with surface active agent like properties, such as PEG 100 Stearate and Poloxamer.

| PART B - Formulations without surfactant | |
|---|---|
| Formulation | % w/w D103 |
| Ingredients | |
| Dimethyl Sulfoxide | 76.60 |
| Water | 20.00 |
| Stearyl alcohol | 3.00 |
| Methocel K100M | 0.40 |
| Total | 100.00 |
| Propellant AP-70 | 8.00 |
| Foam properties | |
| Foam Quality | Good |
| Shakability | Good |
| Collapse Time at 36° C. (sec) | 90 |

Comments: Formulation D103 was prepared according to the General Manufacturing Procedures described in the Method/Test section. This formulation is an example of an aqueous vehicle containing very high amounts of DMSO, some water, a fatty alcohol, a polymeric agent but no surfactant. Surprisingly, and despite the absence of surfactant and the high aprotic solvent level, a breakable foam of good quality was obtained which did not collapse for 90 seconds at 36° C.

In one or more embodiments, there is provided a surfactant-free foam formulation comprising DMSO, water, fatty alcohols and polymeric agents which provides a breakable foam of good quality. In one or more alternative embodiments there is provided a surfactant-free foam formulation comprising DMSO, water, and fatty alcohols essentially free of polymeric agents. In one or more other embodiments there is provided a surfactant-free foam formulation comprising DMSO, water, and polymeric agents essentially free of fatty alcohols.

Example 10—Compositions Containing from 19% to 45% DMSO with and without Diclofenac as an Active Agent ("API")

| | Part A - With and Without API | | | | | |
|---|---|---|---|---|---|---|
| | % w/w | | | | | |
| Formulations | D40 (Placebo) | D40 | D41 | D42 (Placebo) | D42 | D43 |
| Ingredients | | | | | | |
| DMSO | 45.00 | 45.00 | 45.50 | 45.50 | 45.50 | 45.50 |
| Water | 30.50 | 29.00 | 17.90 | 18.10 | 19.60 | 17.90 |
| Glycerin | 7.00 | 7.00 | 10.70 | 10.80 | 10.80 | 10.70 |
| Propylene glycol | 5.00 | 5.00 | 10.70 | 10.80 | 10.80 | 10.70 |
| Ethanol | 10.00 | 10.00 | 11.20 | 11.30 | 11.30 | 11.20 |
| Cetostearyl alcohol | 1.00 | 1.00 | 1.00 | 0.80 | 0.80 | 1.10 |
| Poloxamer 407 | 1.00 | 1.00 | 1.00 | — | — | — |
| Hydroxypropyl methylcellulose K100M | 0.50 | 0.50 | 0.50 | 0.40 | 0.40 | 0.50 |
| PEG 100-Stearate | — | — | — | 0.80 | 0.80 | 0.90 |
| Diclofenac - sodium | — | 1.50 | 1.50 | — | 1.50 | 1.50 |
| Total | 100.00 | 100.00 | 100.00 | 100.00 | 100.00 | 100.00 |
| Propellant AP-70 | 8.00 | 8.00 | 8.00 | 8.00 | 8.00 | 8.00 |
| Foam Properties | | | | | | |
| Foam Quality | Excellent | Excellent | Good to Excellent | Good | Good | Good to Excellent |
| Collapse Time (sec) | >180 | >180 | >180 | >180 | >180 | >180 |
| Presence of drug crystals | Placebo | No | No | Placebo | No | No |

Comments: Formulations D40 to D43 are examples of foam vehicles with and without an active agent, containing 45% of DMSO, water, humectants, gelling agents, a foam adjuvant and/or surfactants. Formulations which contain at least two foam stabilizing components provided breakable foams of good to excellent quality that did not collapse after 180 sec at 36° C.

It can be noted that the addition of about 10% of ethanol did not appear to affect the foam stability or quality. It can also be noted that the addition of an active agent did not appear to affect foam quality and stability, and that all these compositions fully dissolve diclofenac sodium. Accordingly, the penetration of the dissolved API should be facilitated by the aprotic solvent DMSO to provide good bioavailability.

| Part B - DMSO Carrier Formulation without polymer | |
|---|---|
| Formulations | w/w % D100 |
| Ingredients | |
| DMSO | 45.00 |
| Water | 20.00 |
| Ethanol | 10.00 |
| Glycerin | 10.00 |
| Propylene Glycol | 10.00 |
| Cetostearyl alcohol | 1.25 |
| Polysorbate 80 | 1.25 |
| Ceteth-2 | 1.25 |
| PEG-100 Stearate | 1.25 |
| Total | 100.00 |
| Propellant AP-70 | 10.00 |
| Foam Properties | |
| Foam Quality | Excellent |
| Shakability | Good |
| Collapse Time (sec) | >180 |

Comments: Formulation D100 was prepared according to the General Manufacturing Procedures described in the Method/Test section. This formulation is an example of a foam vehicle without polymer containing 45% of DMSO, water, humectant, a foam adjuvant and surfactants that can generate excellent quality foam that did not collapse after 180 sec at 36° C. The presence of about 10% of ethanol did not appear to affect the foam quality or the collapse time.

| Part C | |
|---|---|
| A sample of formulation D40 above was tested for additional physical parameters and the results are provided below: | |
| Viscosity of the pre-foam formulation (cPs) | 146 |
| Density of the foam (g/ml) | 0.066 |
| Foam pH (diluted 1:5 with water) | 6.01 |
| Mean Bubble Size (micrometers) | 69 |

Comments: Formulation D44 is an example of a foam vehicle containing 19% of DMSO, 50% of water, a hydrophobic solvent, a gelling agent, a foam adjuvant and a surfactant. It can be seen that formulations containing a protic polar solvent, an aprotic polar solvent, an apolar solvent and a suitable combination of foam stabilizing agents, can provide breakable foams of good to excellent quality that do not collapse after 180 sec.

| PART D - Emulsion with Hydrophobic Solvent | | | |
|---|---|---|---|
| | w/w % | w/w % Formulations | w/w % |
| | D44 (Placebo) | D53 (Placebo) | D54 (Placebo) |
| Ingredients | | | |
| DMSO | 19.00 | 45.00 | 45.00 |
| Water | 50.00 | 29.00 | 35.00 |
| Light Mineral Oil | 20.00 | 15.00 | 15.00 |
| Stearyl Alcohol | 5.00 | 5.00 | — |
| Hydroxypropyl methylcellulose K100M | 1.00 | 1.00 | — |
| Glycerol monostearate | 5.00 | 5.00 | 5.00 |
| Total | 100.00 | 100.00 | 100.00 |
| Propellant AP-70 | 10.00 | 10.00 | 10.00 |
| Foam Properties | | | |
| Foam Quality | Good | Good | Good |
| Collapse Time (sec) | >180 | >180 | >180 |
| Foam Density | — | 0.166 | 0.213 |

Comments: All the formulations provide quality foams with satisfactory collapse times. Surprisingly, there is no apparent change in quality or collapse on removal of the foam adjuvant and polymer but the density is unexpectedly less when they are present. Without being bound to any theory, it may be that foam adjuvants and/or polymeric agents can enable a better propellant dissolution within the pressurized formulation, and so an improved expansion upon foam dispensing.

Part E—without Surfactant

See Example 9, Part B from which it was unexpectedly observed that a surfactant-free foam formulation comprising DMSO, water, fatty alcohols and polymeric agents provides a breakable foam of good quality.

Part F—Manufacture:

Formulation D53:
1) Mix DMSO and water, Add Methocel K100M at room temperature and mix until gel formation.
2) Heat to 50-60° C., add stearyl alcohol and glycerol monostearate and mix until dissolution.
3) Add slowly light mineral oil and mix until homogeneity is obtained.
4) Cool to room temperature and complete water if necessary to 100%

Formulation D54:
1) Mix DMSO and Water.
2) Heat to 50-60° C. and add glycerol monostearate while mixing to dissolution.
3) & 4) As above.

Example 11—Foamable Vehicle Compositions Containing 45% of Aprotic Solvent

| Part A - Various other examples of aprotic solvents | | | |
|---|---|---|---|
| | % w/w | | |
| Formulations | D45 | D46 | D47 |
| Ingredients | | | |
| Acetone | 45.00 | — | — |
| Acetonitrile | — | 45.00 | — |

-continued

Part A - Various other examples of aprotic solvents

| Formulations | % w/w | | |
|---|---|---|---|
| | D45 | D46 | D47 |
| DMF | — | — | 45.00 |
| Water | 30.50 | 30.50 | 30.50 |
| Glycerin | 7.00 | 7.00 | 7.00 |
| Propylene glycol | 5.00 | 5.00 | 5.00 |
| Ethanol | 10.00 | 10.00 | 10.00 |
| Cetostearyl alcohol | 1.00 | 1.00 | 1.00 |
| Poloxamer 407 | 1.00 | 1.00 | 1.00 |
| Hydroxypropyl methylcellulose K100M | 0.50 | 0.50 | 0.50 |
| Total | 100.00 | 100.00 | 100.00 |
| Propellant AP-70 | 8.00 | 8.00 | 8.00 |
| Foam Properties | | | |
| Foam Quality | Good | Good | Excellent |
| Collapse Time (sec) | >180 | 120 | >180 |

Comments: Formulations D45 to D47 are examples of foam vehicles containing 45% of a polar aprotic solvent, ethanol, water, humectants, gelling agents and a foam adjuvant. The polar aprotic solvents used comprise acetone, acetonitrile and dimethyl formamide. The three formulations provided breakable foams of good to excellent quality that did not collapse after 120 to 180 sec at 36° C., showing that the present invention includes a range of polar aprotic solvents. It can be noted that the addition of about 10% of ethanol did not appear to affect the foam stability or quality.

Part B - Aprotic-hydroalcoholic formulations with 10%; 11.3% and 40% Alcohol

| | % w/w | % w/w | % w/w |
|---|---|---|---|
| | Formulations | | |
| | D40 (Placebo) | D42 (Placebo) | D102 (Placebo) |
| DMSO | 45.00 | 45.50 | 30.00 |
| Water | 30.50 | 18.10 | 15.00 |
| Glycerin | 7.00 | 10.80 | — |
| Propylene glycol | 5.00 | 10.80 | 6.50 |
| Ethanol | 10.00 | 11.30 | 40.00 |
| Cetostearyl alcohol | 1.00 | 0.80 | 3.00 |
| Poloxamer 407 | 1.00 | — | — |
| Hydroxypropyl methylcellulose K100M | 0.50 | 0.40 | — |
| PEG 100-Stearate | — | 0.80 | — |
| Steareth-2 | — | — | 4.00 |
| Hydroxypropyl cellulose EF | — | — | 1.50 |
| Total | 100.00 | 100.00 | 100.00 |
| Propellant AP-70 | 8.00 | 8.00 | 8.00 |
| Foam Properties | | | |
| Foam Quality | Excellent | Good | Excellent |
| Collapse Time (sec) | >180 | >180 | 60 |

Comments: Formulations D40, D42 and D102 were prepared according to the General Manufacturing Procedures described in the Method/Test section. All these aprotic-aqueous formulations produced a foam of quality. Formulation D102 is an example of aqueous foam containing 30% DMSO, a humectant, a fatty alcohol, a polymer and a surfactant, with a high ethanol content of 40% which surprisingly generated a foam of excellent quality. Due to the high ethanol content of D102, the collapse time is shorter than in formulations D40 and D42, but remains essentially satisfactory. In complete contrast, as can be seen in Example 6 Part D, a similar non-aqueous formulation with 40% alcohol did not produce a foam. Thus, it follows that Aprotic—hydroalcoholic formulations are more resilient than their non-aqueous counterparts and that the presence of a relatively small amount of water aids in the quality and or stabilization of the resultant foam.

Section C—Usability Testing

Example 12—Comparative Tolerability and Acceptability Study of a Waterless Foam DMSO Composition Vs. Aqueous Foam DMSO Composition A panel of three testers was asked to apply on their hand an aqueous DMSO foam preparation and a waterless DMSO foam preparation. The waterless formulation was D15 (see Example 3 above) and the aqueous formulation was D33 (see Example 8 above).

Each was asked to describe their feelings about the ease of application, skin feeling and penetrability of each of the products.

Both formulations were described as having a good appearance and an excellent ease of application and penetration speed into the skin upon slight rubbing. Testers added that the aqueous formulation has a very slight greasy feeling on skin, and the waterless formulation has a slight greasy feeling on skin. In both cases, the greasy feeling disappeared after 10 to 20 seconds. Testers did not report any after-taste or bad breath after application. It may be a further unexpected advantage of DMSO foams that such side effects are absent or ameliorated due to the low density of the foam—allowing small amounts to be spread over a target area—and or due to the composition of formulation.

Section D—Packaging Compatibility

Part A—Background

Aprotic solvents, such as, DMSO have outstanding solvent properties, being able to dissolve a wide range of organic and inorganic compounds, including plastics, resins and alloys used in fabrication of canisters and valve parts. Therefore, packaging components for holding and delivering such solvents can readily corrode and/or deteriorate especially when high concentrations are present in the compositions, as disclosed in the present foam formulations.

Aerosol packaging is primarily composed of a coated canister, a valve, an actuator and optionally a dip-tube. The components being in prolonged contact with the formulations are mainly the canister internal coating and valve parts (cup and housing). In the following study the compatibility of various packaging components with highly concentrated DMSO solution was assessed in the absence of propellant.

Part B—Procedure

The tested packaging components are incubated in contact with a solution of DMSO in water (50:50 w/w) during up to six months at 50° C. At the desired time-points, the packaging components are removed from the incubators, canisters are opened and a visual observation is performed to determine the presence deterioration, corrosion, peeling, scratches, etc that may result from the prolonged contact with the DMSO solution.

Part C—Compatibility Results

An aluminum canister with a polyimide amide (PAM) internal coating was filled with a solution of DMSO in water (50:50 w/w), crimped with an epoxy coated valve having a dip-tube and incubated at 50° C.

| Incubation conditions | Canister coating | Valve cup | Valve housing | Dip-tube |
|---|---|---|---|---|
| 1M 50° C. | no change | no change | slight change in color | no change |
| 2M 50° C. | no change | no change | color became pale yellow | no change |
| 3M 50° C. | no change | no change | color became pale yellow | no change |
| 6M 50° C. | no change | no change | color became yellow | no change |

Surprisingly, no canister deterioration was observed, even after 6 months at 50° C. No corrosion or deterioration was observed in the valve cup and in the dip-tube. Only a minor change in color of the valve housing was observed, which is acceptable and not considered as deterioration.

However, a canister with an internal coating made of phenol epoxy and containing formulation D22 showed signs of corrosion after 6 months at room temperature. The valve cup and housing though was of epoxy type and did not show any sign of corrosion. There was no diptube in this canister. So over time during storage canisters, for example, with phenol epoxy coatings can display corrosion and deterioration.

In one or more embodiments, there is provided a kit comprising an aerosol canister, a valve, an actuator, optionally a dip-tube, and a DMSO foam formulation, wherein the packaging components are compatible with a formulation containing DMSO, and wherein essentially no corrosion or deterioration is observed. In one or more embodiments the canisters are essentially free of corrosion and or deterioration for 1 month, or 2 months or for 3 months or for 6 months or for 12 months or for 18 months or for 24 months at room temperature. In one or more further embodiments the canisters are essentially free of corrosion and or deterioration for 1 month, or for 2 months, or for 3 months, or for 6 months, or for 12 months, or for 18 months, or for 24 months at 40° C. In one or more further embodiments the canisters are essentially free of corrosion and or deterioration for 1 month, or 2 months or for 3 months, or for 6 months, or for 12 months, or for 18 months, or for 24 months at 50° C. In one or more other embodiments any corrosion and or deterioration observed was not of significance. In one or more embodiments any corrosion and or deterioration observed in the canisters was not of significance for 1 month, or for 2 months, or for 3 months, or for 6 months, or for 12 months, or for 18 months, or for 24 months at room temperature. In one or more further embodiments any corrosion and or deterioration observed in the canisters was not of significance for 1 month, or for 2 months, or for 3 months, or for 6 months, or for 12 months, or for 18 months, or for 24 months at 40° C. In one or more further embodiments any corrosion and or deterioration observed in the canisters was not of significance for 1 month, or for 2 months, or for 3 months, or for 6 months, or for 12 months, or for 18 months, or for 24 months at 50° C.

Part D—Can in Can

Background: A bag in can can be used in three basic ways with propellant, namely, a) with the propellant not in the bag and being separate from the formulation in the bag; b) with propellant present in the formulation in the bag only; c) with propellant both in the bag and outside of the bag. In case a) without surfactant the formulation is likely to exit as a gel or fluid. In cases b) and c) the formulation can foam. The propellant outside the bag is to expel the contents of the bag. The propellant within the formulation in the bag is to generate foam. When the formulation is primarily expelled by propellant outside the bag then the amount of propellant in the formulation can influence foam properties, such as, density.

An aluminum can-in-can canister with a phenol epoxy internal coating was filled with a solution of DMSO in water (50:50 w/w), crimped with an epoxy coated valve without dip-tube and incubated for one month at 50° C.

After opening of the canister, no corrosion or deterioration was observed neither on the canister internal coating, nor on the different valve parts.

In one or more embodiments, there is provided a kit comprising a can-in-can aerosol canister, a valve, an actuator, optionally a dip-tube, and a DMSO foam formulation, wherein the packaging components are compatible with a formulation containing DMSO, and wherein no corrosion or deterioration is observed. In one or more embodiments the canisters are essentially free of corrosion and or deterioration for 1 month, or 2 months or for 3 months or for 6 months or for 12 months or for 18 months or for 24 months at room temperature. In one or more further embodiments the canisters are essentially free of corrosion and or deterioration for 1 month, or for 2 months, or for 3 months, or for 6 months, or for 12 months, or for 18 months, or for 24 months at 40° C. In one or more further embodiments the canisters are essentially free of corrosion and or deterioration for 1 month, or 2 months or for 3 months, or for 6 months, or for 12 months, or for 18 months, or for 24 months at 50° C. In one or more other embodiments any corrosion and or deterioration observed was not of significance. In one or more embodiments any corrosion and or deterioration observed in the canisters was not of significance for 1 month, or for 2 months, or for 3 months, or for 6 months, or for 12 months, or for 18 months, or for 24 months at room temperature. In one or more further embodiments any corrosion and or deterioration observed in the canisters was not of significance for 1 month, or for 2 months, or for 3 months, or for 6 months, or for 12 months, or for 18 months, or for 24 months at 40° C. In one or more further embodiments any corrosion and or deterioration observed in the canisters was not of significance for 1 month, or for 2 months, or for 3 months, or for 6 months, or for 12 months, or for 18 months, or for 24 months at 50° C.

What is claimed is:

1. A foam able composition formulated for administration to the skin comprising a carrier composition comprising:
   a) a short chain alcohol comprising ethanol present at a concentration of at least 55% by weight of the carrier;
   b) about 2% to about 50% by weight of the carrier of a protic polar solvent comprising propylene glycol;
   c) a polymeric agent comprising a cellulose ether, wherein the cellulose ether is a hydroxypropyl cellulose present at a concentration of about 0.5% to about 1% by weight of the carrier;
   d) a modulating agent comprising an antioxidizing agent present at a concentration of about 0.1% to about 10% by weight of the carrier;
   e) a metal;
   f) an essential oil; and
   g) tetracycline in a therapeutically effective amount of about 1% to about 5% by weight of the carrier,
   wherein the composition is surfactant free, nonaqueous, and tree or essentially free of fatty alcohol.

2. The foamable composition of claim 1, wherein the protic polar solvent is at a concentration of about 12% to about 30% by weight of the carrier.

3. The foamable composition of claim 1, further comprising a liquefied or compressed gas propellant present at a concentration of about 3% to about 25% by weight of the foamable composition.

4. A foamable composition formulated for administration to the skin comprising a carrier composition comprising:
   a) a short chain alcohol comprising ethanol;
   b) about 12% to about 30% by weight of the carrier of a protic polar solvent comprising propylene glycol;
   c) a polymeric agent comprising a cellulose ether;
   d) a modulating agent comprising an antioxidizing agent;
   e) a metal;
   f) an essential oil; and
   g) tetracycline in a therapeutically effective amount of about 1% to about 5% by weight of the carrier,
   wherein the composition is surfactant free, nonaqueous, and free or essentially free of fatty alcohol.

5. The foamable composition of claim 4, wherein the short chain alcohol is present at a concentration of at least 55% by weight of the carrier.

6. The foamable composition of claim 4, wherein the cellulose ether is a hydroxypropyl cellulose.

7. The foamable composition of claim 4, wherein the cellulose ether is present in a concentration of about 0.5% to about 1% by weight of the carrier.

8. The foamable composition of claim 4, wherein the modulating agent is present at a concentration of about 0.1% to about 10% by weight of the carrier.

9. The foamable composition of claim 4, further comprising a liquefied or compressed propellant at a concentration of about 3% to about 25% by weight of the foamable composition.

* * * * *

UNITED STATES PATENT AND TRADEMARK OFFICE
CERTIFICATE OF CORRECTION

Page 1 of 1

PATENT NO. : 10,588,858 B2
APPLICATION NO. : 16/443649
DATED : March 17, 2020
INVENTOR(S) : Dov Tamarkin et al.

It is certified that error appears in the above-identified patent and that said Letters Patent is hereby corrected as shown below:

On the Title Page

Item (72), Lines 2-3 of Inventors, "Tal Berman, Rishon le Ziyyon (IL)" should read --Tal Berman, Rishon LeZiyyon (IL)--.

In the Claims

Claim 1, Column 54, Line 46, "A foam able composition" should read --a foamable composition--.

Claim 1, Column 54, Line 64, "and tree or essentially free" should read --and free or essentially free--.

Signed and Sealed this
Eleventh Day of August, 2020

Andrei Iancu
*Director of the United States Patent and Trademark Office*